(12) United States Patent
Sidduri et al.

(10) Patent No.: US 6,380,387 B1
(45) Date of Patent: Apr. 30, 2002

(54) 4-PYRIMIDINYL-N-ACYL-L PHENYLALANINES

(75) Inventors: Achyutharao Sidduri, Livingston; Jefferson Wright Tilley, North Caldwell, both of NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 09/717,912

(22) Filed: Nov. 21, 2000

Related U.S. Application Data

(60) Provisional application No. 60/245,601, filed on Nov. 3, 2000, and provisional application No. 60/169,089, filed on Dec. 6, 1999.

(51) Int. Cl.[7] .................................. C07D 239/54
(52) U.S. Cl. .................. 544/311; 544/309; 544/310; 544/295; 544/296; 544/123; 544/58.6; 540/601
(58) Field of Search ................. 544/309, 310, 544/311, 295, 296, 123, 58.6; 540/601

(56) References Cited

FOREIGN PATENT DOCUMENTS

| WO | 98 53814 | 12/1998 |
|---|---|---|
| WO | 98 53817 | 12/1998 |
| WO | 99 10312 | 3/1999 |
| WO | 99 10313 | 3/1999 |
| WO | 99 26921 | 6/1999 |
| WO | 99 36393 | 7/1999 |
| WO | 99 37618 | 7/1999 |
| WO | 99 43642 | 9/1999 |
| WO | 99 64395 | 12/1999 |
| WO | 00 43354 | 7/2000 |
| WO | 00 48988 | 8/2000 |
| WO | 00 48994 | 8/2000 |

*Primary Examiner*—John M. Ford
(74) *Attorney, Agent, or Firm*—George W. Johnston; Dennis P. Tramaloni

(57) ABSTRACT

Compounds of Formula I are disclosed,

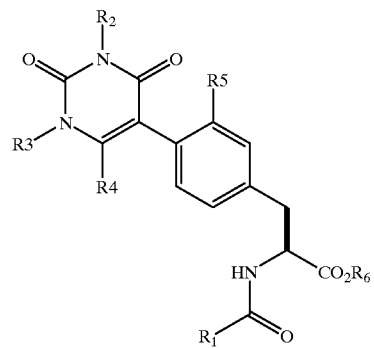

having activity as inhibitors of binding between VCAM-1 and cells expressing VLA-4, and accordingly useful for treating diseases whose symptoms and or damage are related to the binding of VCAM-1 to cells expressing VLA-4.

61 Claims, No Drawings

4-PYRIMIDINYL-N-ACYL-L PHENYLALANINES

This application claims priority under 35 U.S.C. § 119(e) of provisional applications Ser. No. 60/169,089 filed on Dec. 6, 1999, and Ser. No. 60/245,601, filed Nov. 3, 2000.

BACKGROUND OF THE INVENTION

Vascular cell adhesion molecule-1 (VCAM-1), a member of the immunoglobulin (Ig) supergene family, is expressed on activated, but not resting, endothelium. The integrin VLA-4($\alpha_4\beta_1$), which is expressed on many cell types including circulating lymphocytes, eosinophils, basophils, and monocytes, but not neutrophils, is the principal receptor for VCAM-1. Antibodies to VCAM-1 or VLA-4 can block the adhesion of these mononuclear leukocytes, as well as melanoma cells, to activated endothelium in vitro. Antibodies to either protein have been effective at inhibiting leukocyte infiltration and preventing tissue damage in several animal models of inflammation. Anti-VLA-4 monoclonal antibodies have been shown to block T-cell emigration in adjuvant-induced arthritis, prevent eosinophil accumulation and bronchoconstriction in models of asthma, and reduce paralysis and inhibit monocyte and lymphocyte infiltration in experimental autoimmune encephalitis (EAE). Anti-VCAM-1 monoclonal antibodies have been shown to prolong the survival time of cardiac allografts. Recent studies have demonstrated that anti-VLA-4 mAbs can prevent insulitis and diabetes in non-obese diabetic mice, and significantly attenuate inflammation in the cotton-top tamarin model of colitis. It has further been shown that VCAM is expressed on endothelial cells of inflamed colonic tissue in a TNB/ethanol rat model of inflammatory bowel disease (*Gastroenterology* 1999, 116, 874–883).

Thus, compounds which inhibit the interaction between α4-containing integrins and VCAM-1 will be useful as therapeutic agents for the treatment of chronic inflammatory diseases such as rheumatoid arthritis (RA), multiple sclerosis (MS), asthma, and inflammatory bowel disease (IBD).

SUMMARY OF THE INVENTION

It has been discovered that compounds of the formula I

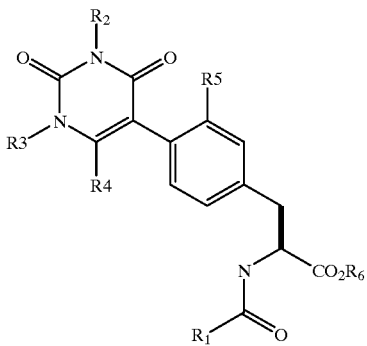

I and the pharmaceutically acceptable salts thereof wherein $R_1$, $R_2$, $R_3$, $R_5$, and $R_6$ are as defined below, inhibit the binding of VCAM-1 to VLA-4 and so would be useful in treating inflammatory diseases in which such binding contributes to the disease process.

DETAILED DESCRIPTION OF THE INVENTION

As used in this specification, the term "halogen" means any of the four halogens, bromine, chlorine, fluorine, and iodine unless indicated otherwise. Preferred halogens are bromine, fluorine, and chlorine.

The term "lower alkyl", alone or in combination, means a straight-chain or branched-chain alkyl group containing a maximum of six carbon atoms, such as methyl, ethyl, n-propyl, isopropyl, n-butyl, sec.butyl, isobutyl, tert.butyl, n-pentyl, n-hexyl and the like. Also, as used herein "lower alkyl" may be groups which are unsubstituted or substituted by one or more groups selected independently from cycloalkyl, nitro, aryloxy, aryl, hydroxy, halogen, cyano, lower alkoxy, lower alkanoyl, lower alkylthio, lower alkyl sulfinyl, lower alkyl sulfonyl, and amino or mono- or di-lower alkyl amino. Examples of substituted lower alkyl groups include 2-hydroxylethyl, 3-oxobutyl, cyanomethyl, and 2-nitropropyl. The term "perfluoro lower alkyl" for purposes of $R^4$, $R^{22}$, or $R^{23}$ means a substituted lower alkyl group as defined above which is a methyl or ethyl group where all of the hydrogens are substituted by fluoro, i.e. trifluoromethyl and pentafluoroethyl.

The term "lower alkenyl" means an alkylene group having from 2 to 10 carbon atoms with a double bond located between any two adjacent carbon atoms.

The term "cycloalkyl" means an unsubstituted or substituted 3- to 7-membered carbacyclic ring. Substituents useful in accordance with the present invention are hydroxy, halogen, cyano, lower alkoxy, lower alkanoyl, lower alkyl, aroyl, lower alkylthio, lower alkyl sulfinyl, lower alkyl sulfonyl, aryl, heteroaryl and substituted amino.

The term "lower alkoxy" means a straight-chain or branched-chain alkoxy group containing a maximum of six carbon atoms, such as methoxy, ethoxy, n-propoxy, isopropoxy, n-butoxy, tert-butoxy and the like.

The term "lower alkylthio" means a lower alkyl group bonded to the rest of the molecule through a divalent sulfur atom, for example, a methyl mercapto or a isopropyl mercapto group. The term "lower alkylsulfinyl" means a lower alkyl group as defined above bound to the rest of the molecule through the sulfur atom in the sulfinyl group. The term "lower alkyl sulfonyl" means a lower alkyl group as defined above bound to the rest of the molecule through the sulfur atom in the sulfonyl group.

The term "aryl" means a mono- or bicylic aromatic group, such as phenyl or naphthyl, which is unsubstituted or substituted by conventional substituent groups. Preferred substituents are lower alkyl, lower alkoxy, hydroxy lower alkyl, hydroxy, hydroxyalkoxy, halogen, lower alkylthio, lower alkylsulfinyl, lower alkylsulfonyl, cyano, nitro, perfluoroalkyl, alkanoyl, aroyl, aryl alkynyl, lower alkynyl and lower alkanoylamino. Examples of aryl groups that may be used in accordance with this invention are phenyl, p-tolyl, p-methoxyphenyl, p-chlorophenyl, m-hydroxy phenyl, m-methylthiophenyl, 2-methyl-5-nitrophenyl, 2,6-dichlorophenyl, 1-naphthyl and the like.

The term "arylalkyl" means a lower alkyl group as hereinbefore defined in which one or more hydrogen atoms is/are replaced by an aryl or heteroaryl group as herein defined. Any conventional aralkyl may be used in accordance with this invention, such as benzyl and the like.

The term "heteroaryl" means an unsubstituted or substituted 5- or 6-membered monocyclic hetereoaromatic ring or a 9- or 10-membered bicyclic hetereoaromatic ring containing 1, 2, 3 or 4 hetereoatoms which are independently N, S or O. Examples of hetereoaryl rings are pyridine, benzimidazole, indole, imidazole, thiophene, isoquinoline, quinzoline and the like. Substituents as defined above for "aryl" are included in the definition of heteroaryl.

The term "lower alkoxycarbonyl" means a lower alkoxy group bonded to the rest of the molecule via a carbonyl group. Examples of alkoxycarbonyl groups are ethoxycarbonyl and the like.

The term "lower alkylcarbonyloxy" means lower alkylcarbonyloxy groups bonded to the rest of the molecule via an oxygen atom, for example an acetoxy group. The term "acyloxy" has the same meaning.

The term "lower alkanoyl" means lower alkyl groups bonded to the rest of the molecule via a carbonyl group and embraces in the sense of the foregoing definition groups such as acetyl, propionyl and the like. The term "perfluoro lower alkanoyl" means a perfluoro lower alkyl group (a substituted lower alkyl group where all of the hydrogens are substituted by fluoro, preferably trifluoromethyl or pentafluoroethyl bonded to the rest of the molecule via a carbonyl group. The term perfluoro lower alkanoylamino" means a perfluoro lower alkanoyl group bonded to the rest of the molecule via an amino group.

The term "lower alkylcarbonylamino" means lower alkylcarbonyl groups bonded to the rest of the molecule via a nitrogen atom, such as acetylamino. The term lower alkylaminocarbonyl" means lower alkyl amino groups bonded to the rest of the molecule via a carbonyl group. The term "arylaminocarbonyl" means aryl groups bonded to an amino group further bonded to the rest of the molecule via a carbonyl group.

The term "aroyl" means a mono- or bicyclic aryl or heteroaryl group bonded to the rest of the molecule via a carbonyl group. Examples of aroyl groups are benzoyl, 3-cyanobenzoyl, 2-naphthoyl, nicotinoyl, and the like.

Pharmaceutically acceptable salts are well known in the art and can be made by conventional methods taking into account the chemical nature of the compound. Examples of pharmaceutically acceptable salts for acidic compounds are alkali metal or alkaline earth metals such as sodium, potassium, calcium, magnesium, basic amines or basic amino acids, ammonium or alkyl ammonium salts. Particularly desirable salts for compounds of this invention are sodium salts. The sodium salt of any acid of this invention is easily obtained from the acid by treatment with sodium hydroxide. For basic compounds, examples are salts of inorganic or organic acids such as hydrochloric, hydrobromic, sulphuric, nitric, phosphoric, citric, formic, fumaric, maleic, acetic, succinic, tartaric, methanesulfonic, and p-toluenesulfonic acid.

The present invention comprises a compound of the formula I:

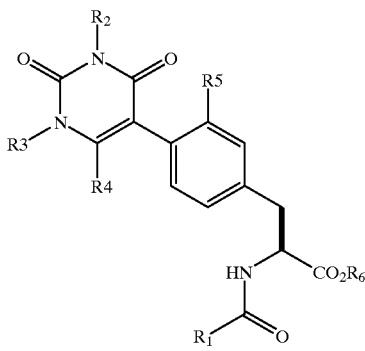

and the pharmaceutically acceptable salts thereof. In accordance with the invention, $R_1$ is a group Y-1, Y-2 or Y-3 as described below:

$R^1$ is Y-1, a group of the formula:

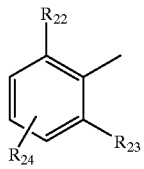

Y-1 wherein: $R_{22}$ and $R_{23}$ are independently hydrogen, lower alkyl, lower alkoxy, cycloalkyl, aryl, arylalkyl, nitro, cyano, lower alkylthio, lower alkylsulfinyl, lower alkyl sulfonyl, lower alkanoyl, halogen, or perfluorolower alkyl and at least one of $R_{22}$ and $R_{23}$ is other than hydrogen, and $R_{24}$ is hydrogen, lower alkyl, lower alkoxy, aryl, nitro, cyano, lower alkyl sulfonyl, or halogen, $R^1$ is Y-2, a five or six membered heteroaromatic ring bonded via a carbon atom to the amide carbonyl wherein said ring contains one, two or three heteroatoms selected from the group consisting of N, O and S and one or two atoms of said ring are independently substituted by lower alkyl, cycloalkyl, halogen, cyano, perfluoroalkyl, or aryl and at least one of said substituted atoms is adjacent to the carbon atom bonded to the amide carbonyl, $R^1$ is Y-3, a 3–7 membered ring of the formula:

Y-3 wherein: $R_{25}$ is lower alkyl, unsubstituted or fluorine substituted lower alkenyl, or a group of formula $R_{26}$—$(CH_2)_e$—, $R_{26}$ is aryl, heteroaryl, azido, cyano, hydroxy, lower alkoxy, lower alkoxycarbonyl, lower alkanoyl, lower alkylthio, lower alkyl sulfonyl, lower alkyl sulfinyl, perfluoro lower alkanoyl, nitro, or $R_{26}$ is a group of formula —$NR_{28}R_{29}$, wherein $R_{28}$ is hydrogen or lower alkyl, $R_{29}$ is hydrogen, lower alkyl, lower alkoxycarbonyl, lower alkanoyl, aroyl, perfluoro lower alkanoylamino, lower alkyl sulfonyl, lower alkylaminocarbonyl, arylaminocarbonyl, or $R_{28}$ and $R_{29}$, taken together with the attached nitrogen atom, form a 4, 5 or 6-membered saturated heterocyclic ring optionally containing one additional heteroatom selected from O, S, and N—$R_{40}$, Q is —$(CH_2)_f$O—, —$(CH_2)_f$S—, —$(CH_2)_f$N($R_{27}$)—, —$(CH_2)_f$—, $R_{27}$ is H, lower alkyl, aryl, lower alkanoyl, aroyl or lower alkoxycarbonyl, $R_{40}$ is H, lower alkyl, aryl, lower alkanoyl, aroyl or lower alkoxycarbonyl, the carbon atoms in the ring are unsubstituted or substituted by lower alkyl or halogen, e is an integer from 0 to 4, and f is an integer from 0 to 3; $R_2$ is hydrogen or lower alkyl substituted lower alkyl arylalkyl, or aryl; $R_3$ is hydrogen or lower alkyl, substituted lower alkyl, arylalkyl, or aryl; $R_4$ is hydrogen, lower alkyl, substituted lower alkyl (such as perfluoro lower alkyl), or aryl; $R_5$ is hydrogen, lower alkyl, chloro, or lower alkoxy; $R_6$ is hydrogen, lower alkyl, lower alkyl carbonyloxy lower alkyl, substituted lower alkyl, or $R_6$ is a group of formula P-3:

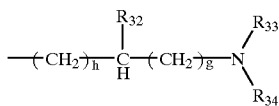

P-3 wherein: $R_{32}$ is hydrogen or lower alky, $R_{33}$ is hydrogen, lower alkyl, aryl, $R_{34}$ is hydrogen or lower alkyl, h is an integer from 0 to 2, g is an integer from 0 to 2, the sum of h and g is 1 to 3; or $R_6$ is a group of formula P-4:

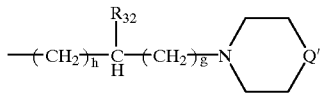

P-4 wherein: $R_{32}$, g, and h are as previously defined, Q' is O, S, —$(CH_2)_j$—, or a group of the formula N—$R_{35}$ $R_{35}$ is hydrogen, lower alkyl, lower alkanoyl, lower alkoxycarbonyl, j is 0, 1 or 2

The compounds of the invention can exist as stereoisomers and diastereomers, all of which are encompassed within the scope of the present invention.

The compounds of the invention inhibit the binding of VCAM-1 and fibronectin to VLA-4 on circulating lymphocytes, eosinophils, basophils, and monocytes ("VLA-4-expressing cells"). The binding of VCAM-1 and fibronectin to VLA-4 on such cells is known to be implicated in certain disease states, such as rheumatoid arthritis, multiple sclerosis, inflammatory bowel disease, and particularly in the binding of eosinophils to airway endothelium which contributes to the cause of the lung inflammation which occurs in asthma. Thus, the compounds of the present invention are useful for the treatment of asthma.

On the basis of their capability of inhibiting binding of VCAM-1 and fibronectin to VLA-4 on circulating lymphocytes, eosinophils, basophils, and monocytes, the compounds of the invention can be used as medicament for the treatment of disorders which are known to be associated with such binding. Examples of such disorders are rheumatoid arthritis, multiple sclerosis, asthma, and inflammatory bowel disease. The compounds of the invention are preferably used in the treatment of diseases which involve pulmonary inflammation, such as asthma. The pulmonary inflammation which occurs in asthma is related to the activation and lung infiltration of eosinophils, monocytes and lymphocytes which have been activated by some asthma-triggering event or substance.

Furthermore, compounds of the invention also inhibit the binding of MadCAM to the cellular receptor alpha4-beta7, also known as LPAM, which is expressed on lymphocytes, eosinophiles and T-cells. While the precise role of alpha4-beta7 interaction with various ligands in inflammatory conditions such as asthma is not completely understood, compounds of the invention which inhibit both alpha4-beta1 and alpha4-beta7 receptor binding are particularly effective in animal models of asthma. Furthermore work with monoclonal antibodies to alpha4-beta7 indicate that compounds which inhibit alpha4-beta7 binding to MadCAM are useful for the treatment of inflammatory bowel disease. They would also be useful in the treatment of other diseases in which such binding is implicated as a cause of disease damage or symptoms.

The compounds of the invention can be administered orally, rectally, or parentally, e.g., intravenously, intramuscularly, subcutaneously, intrathecally or transdermally; or sublingually, or as opthalmalogical preparations, or as an aerosol in the case of pulmonary inflammation. Capsules, tablets, suspensions or solutions for oral administration, suppositories, injection solutions, eye drops, salves or spray solutions are examples of administration forms.

Intravenous, intramuscular, oral or inhalation administration is a preferred form of use. The dosages in which the compounds of the invention are administered in effective amounts depending on the nature of the specific active ingredient, the age and the requirements of the patient and the mode of administration. Dosages may be determined by any conventional means, e.g., by dose-limiting clinical trials. Thus, the invention further comprises a method of treating a host suffering from a disease in which VCAM-1 or fibronectin binding to VLA-4-expressing cells is a causative factor in the disease symptoms or damage by administering an amount of a compound of the invention sufficient to inhibit VCAM-1 or fibronectin binding to VLA-4-expressing cells so that said symptoms or said damage is reduced. In general, dosages of about 0.1–100 mg/kg body weight per day are preferred, with dosages of 1–25 mg/kg per day being particularly preferred, and dosages of 1–10 mg/kg body weight per day being espeically preferred.

The invention further comprises pharmaceutical compositions which contain a pharmaceutically effective amount of a compound of the invention and a pharmaceutically acceptable carrier. Such compositions may be formulated by any conventional means. Tablets or granulates can contain a series of binders, fillers, carriers or diluents. Liquid compositions can be, for example, in the form of a sterile water-miscible solution. Capsules can contain a filler or thickener in addition to the active ingredient. Furthermore, flavour-improving additives as well as substances usually used as preserving, stabilizing, moisture-retaining and emulsifying agents as well as salts for varying the osmotic pressure, buffers and other additives can also be present.

The previously mentioned carrier materials and diluents can comprise any conventional pharmaceutically acceptable organic or inorganic substances, e.g., water, gelatine, lactose, starch, magnesium stearate, talc, gum arabic, polyalkylene glycols and the like.

Oral unit dosage forms, such as tablets and capsules, preferably contain from 25 mg to 1000 mg of a compound of the invention.

Generally the compounds of the present invention can be prepared from suitable phenylalanine derivatives via a palladium catalyzed reaction with a 5-halo-2,4-dioxopyrimidone.

As shown in Reaction Scheme 1, a 4-iodo- or 4-bromophenylalanine derivative such as 1, is converted into a protected phenylalanine derivative 2 in which $R_5'$ is hydrogen, chloro, lower alkyl or lower alkoxy, $P_1$ is a standard nitrogen protecting group such as a Boc, or carbobenzyloxy group and $P_2$ is lower alkyl or substituted lower alkyl selected appropriately to serve as a protecting group or an element of a prodrug. The group $P_2$ can be introduced by conventional means familiar to those who practice peptide chemistry. The order of the addition of $P_1$ and $P_2$ is not critical and will depend on the particular choice of reagents. A discussion of the use and introduction of protecting groups is provided in Theodora W. Greene and Peter G. M. Wuts., *Protecting Groups in Organic Synthesis*, Wiley Interscience, New York, 1991. Alternatively, a compound of formula 1 may be converted to a compound of formula 4, in which $R_1'$ represents a component of an acyl group of the invention. A convenient method is to introduce the ester group $P_2$ first, followed by a coupling reaction of the free amine using conventional peptide coupling reagents, for example HBTU in the presence of a tertiary amine base such as diethylisopropylamine. Again, the particular choice of reagents may dictate altering the sequence of the introduction of $R_1'$ and $P_2$. Conversion of compounds of formula 2 or 4 to derivatives 3 or 5, in which M represents a substituted tin or boron atom, can be effected by treatment with a suitable species, for example hexamethylditin, hexabutylditin or a tetraalkoxydiboron in the presence of a source of palladium zero. The methodology is outlined and referenced in F. Diederich and P. J. Stang, ed, *Metal Catalyzed Cross Coupling Reactions*, Wiley-VCH, Weinheim, Germany, 1998.

Reaction Scheme 1

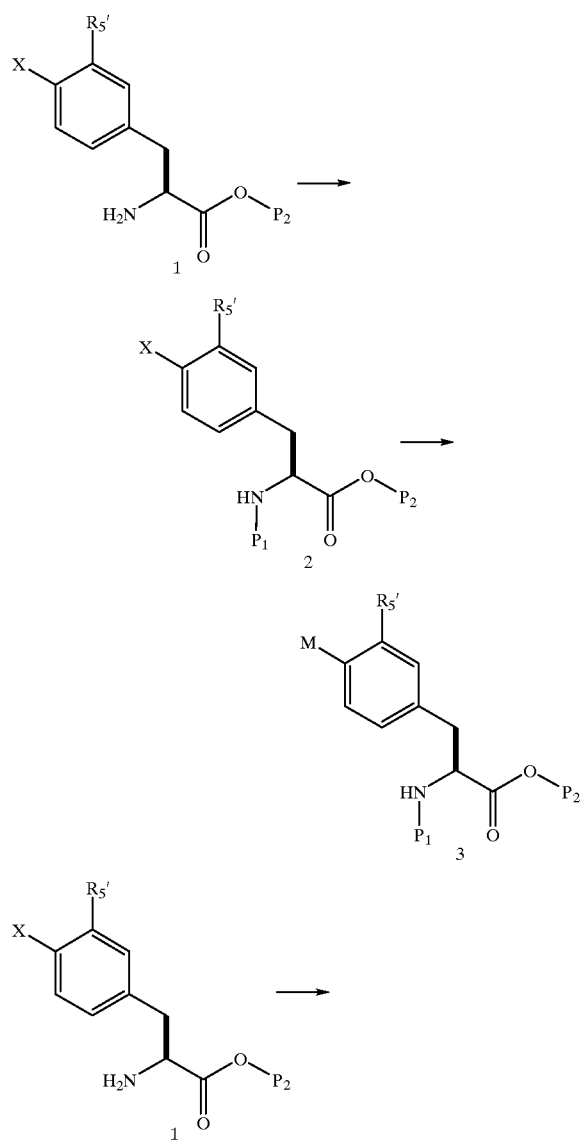

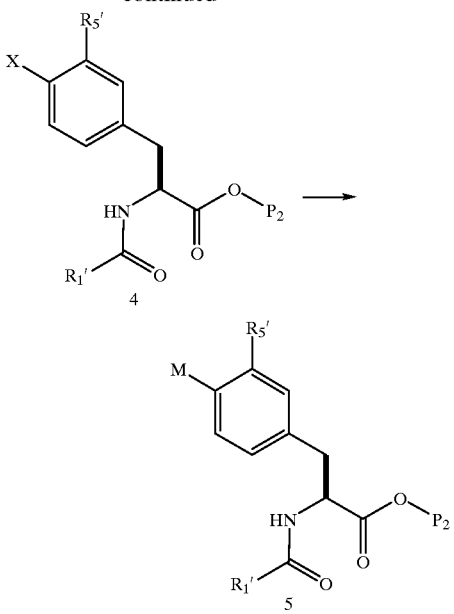

Pyrimidine-2,4-diones (uracil derivatives) of formula 6 wherein $R_4'$ is hydrogen, lower alkyl or perfluorolower alkyl are well known in the literature or can be made by known methods. 1,3-Disubstituted pyrimidin-2,4-diones of formula 7 wherein $R_2'$ and $R_3'$ are lower alkyl, aryl lower alkyl or aryl are also known compounds or can be prepared by standard procedures. Papers reporting synthetic methods for their construction include: Shigeo Senda, et al. Chem. Pharm. Bull. 1974, 22, 189–195, Chem Pharm Bull 1972, 20, 1389–1396, and Yasuo Morita, et al., Chem Comm. 1997 359–360. For the case where R2' and R3' are lower alkyl or aryl lower alkyl, compounds of formula 7 are available by alkylation of compounds of formula 6 by treatment with an alkylating agents such as iodomethane, benzylbromide, allyl bromide in the presence of a base such as potassium carbonate and optionally, a phase transfer catalyst. For less reactive alkylating agents, it may be necessary to use a stronger base such as an alkali metal hydroxide and to heat the reaction mixture. Compounds of formula 6 or 7 as defined above may be halogenated in the 5-position by treatment with conventional halogenating reagents such as bromine, N-iodosuccinimide or N-bromosuccinimide in a suitable solvent such as glacial acetic acid or aqueous acetic acid to give halopyrimidines of formula 8, X=Br or I, $R_2'$, and $R_3'$, are independently hydrogen, lower alkyl, aryl lower alkyl or aryl, $R_4'$=hydrogen, lower alkyl or perfluorolower alkyl.

Reaction Scheme 2

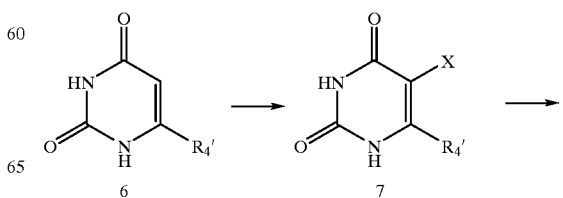

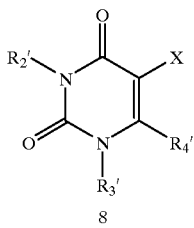

8

As shown in Reaction Scheme 3, the compound of formula 8 can be used in a palladium catalyzed coupling reaction with a phenylalanine derivative of formula 3 or 5. For example, when M is a substituted tin, treatment of a mixture of 8 and the phenylalanine of formula 3 or 5 with a source of palladium zero such as tetraakis(triphenylphosphine)palladium or bis(triphenylphosphine)palladium dichloride in the presence of an inert solvent such as DMF at a temperature of between room temperature and 100° C. gives a compound of formula 9 or 10. Compounds of structure 9 may be converted into compounds of structure 10 by removal of the protecting group $P_1$, which may be accomplished by conventional means depending on the selection of $P_1$. For example, if $P_1$ is a Boc group, it may be removed by treatment with a strong acid, such as trifluoroacetic acid, optionally in the presence of a solvent such as dichloromethane and a scavenging agent. The resulting free amine may then be acylated with an acid of the formula $R_1'CO_2H$ using conventional peptide coupling techniques. For example, by treatment with HBTU in the presence of a tertiary amine base such as diethylisopropylamine in the presence of an aprotic solvent such as DMF to give the compound of structure 10.

If the free acid 11 is the desired end product, the ester group, $P_2$ may be removed by conventional means. For example, in the case that $P_2$ is lower alkyl, for example methyl, it may be removed by treatment with an alkali metal hydroxide, for example lithium hydroxide, in a suitable solvent, for example aqueous THF optionally containing methanol to assist with solubility. If $P_2$ were a benzyl or substituted benzyl group, it could also be removed by catalytic hydrogenation over a noble metal catalyst, for example palladium on carbon.

Reaction Scheme 3

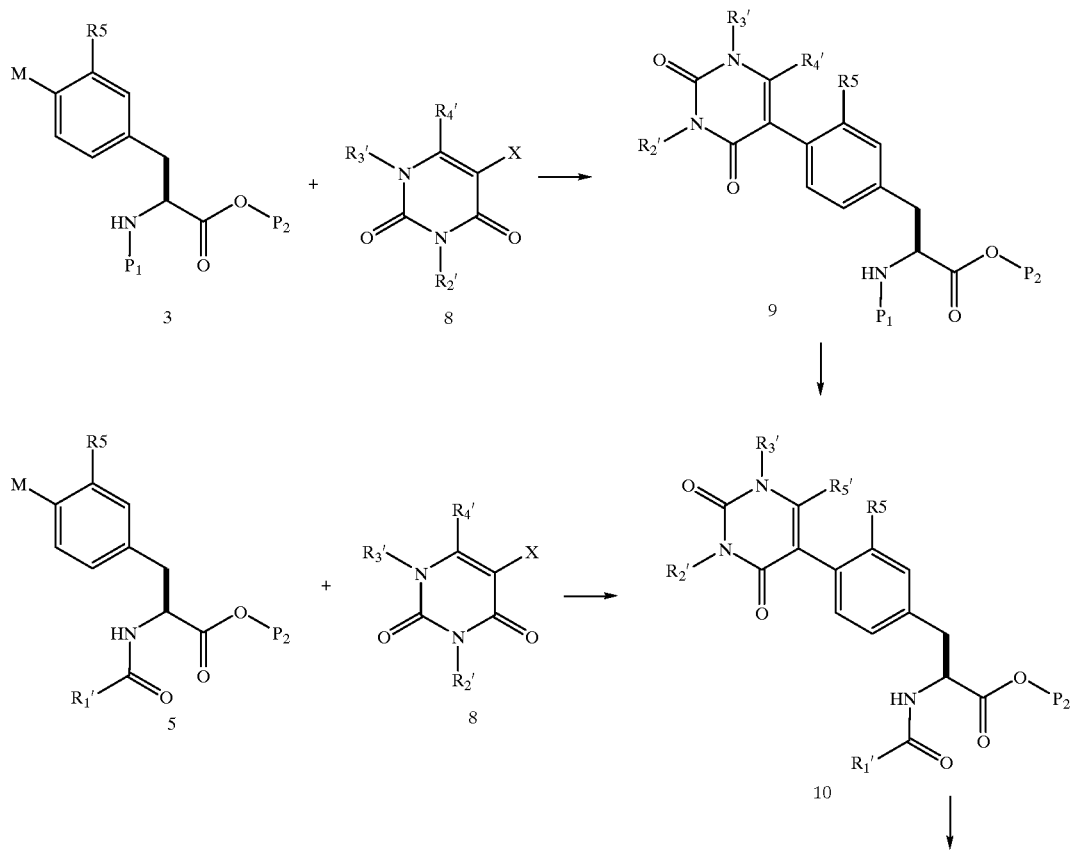

-continued

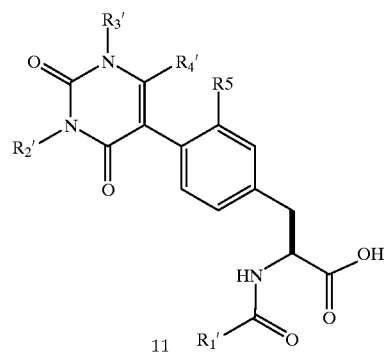

Alternatively, as shown in Reaction Scheme 4, a compound of structure 8, wherein X is bromide or iodide, may be converted to a species of formula 12, in which M' represents a substituted tin, boron or zinc atom. In the case of the tin or boron derivatives, in which M' represents a substituted tin or boron atom, the conversion can be effected by treatment with a suitable species, for Reaction Scheme 4

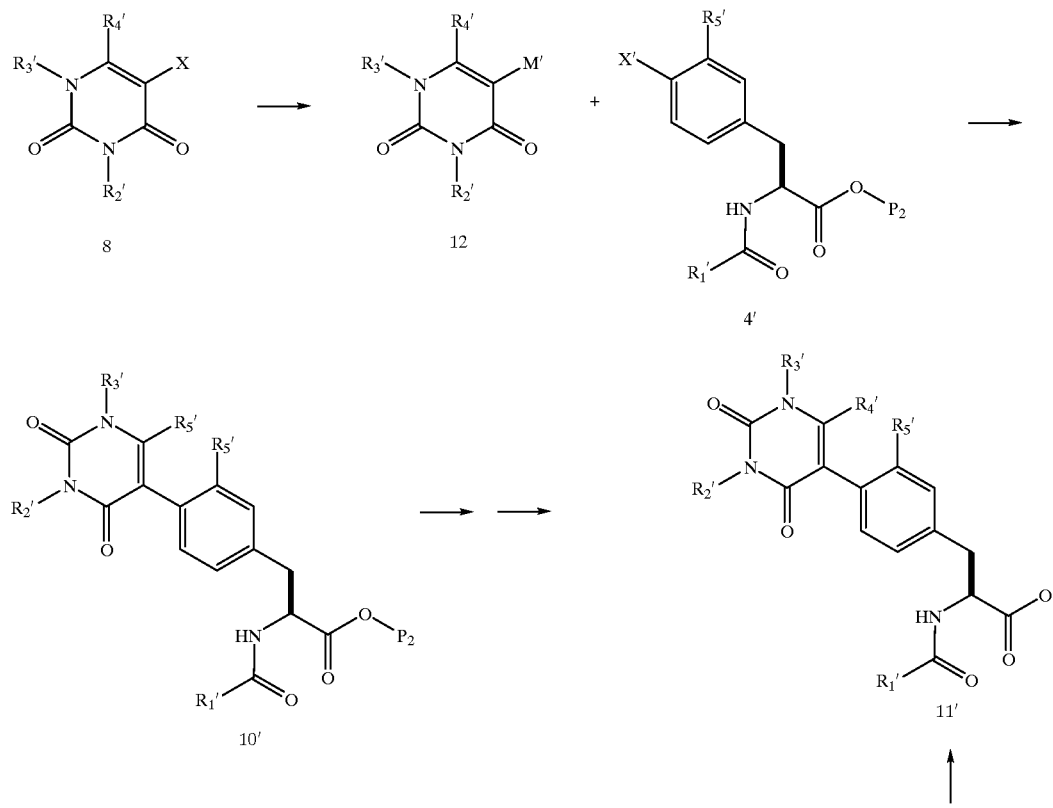

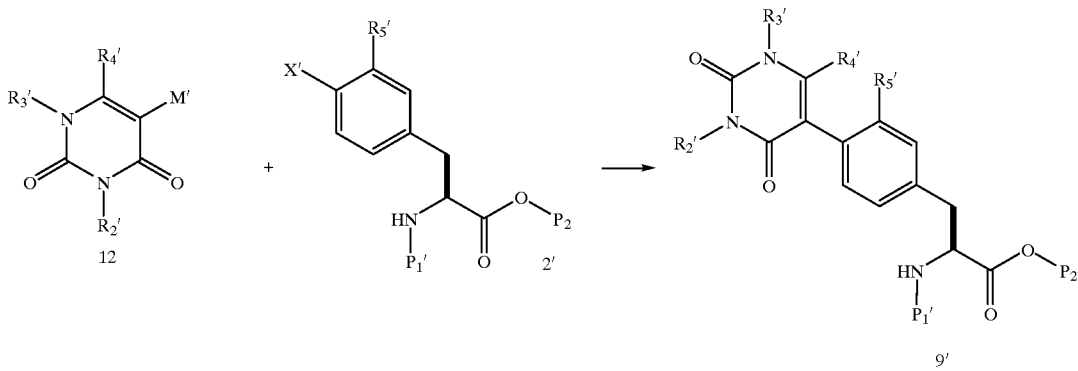

example hexamethylditin, hexabutylditin or a tetaalkoxydiboron in the presence of a source of palladium zero. For the formation of the zinc derivative, 12, M'=Zn(halogen), conversion may be effected by treatment of the compound of formula 8, X=I with a source of activated zinc metal in a suitable inert solvent, for example dimethylacetamide at a temperature of from room temperature to 100° C. until conversion is complete to give a compound of formula 12, M'=Zn(halogen). These compounds of formula 12 can be reacted with a 4-substituted phenylalanine derivative of formula 4' in which X' is iodo, bromo, or trifluoromethylsulfonyloxy in the presence of a source of palladium zero to give a compound of formula 10'. In the case where the ester group represented by $P_2$ is not part of the targeted compound, it can be removed using ester hydrolysis procedures appropriate to the particular $P_2$. For example, where $P_2$ is lower alkyl, for example methyl, it can be removed by standard base hydrolysis using an alkali metal hydroxide, for example, lithium hydroxide. In a variation on this procedure, it may be desirable to carry a protecting group through the coupling reaction and substitute it at a later time. In this case, a compound of formula 2', in which $P_1'$ is lower alkoxycarbonyl or benzyloxycarbonyl and X' is as defined above, may be coupled with a pyrimidinedione of structure 12 to give a compound of structure 9' which in turn may be converted to a compound of the invention using the general procedures noted above in reaction scheme 3.

An alternative route to compounds of this invention, as shown in Reaction Scheme 5, which is particularly applicable to compounds in which $R_5'$ is other than hydrogen, is to build an aldedyde of formula 14. This can be accomplished by reacting a compound of formula 12 with a compound of formula 13, in which $R_5'$ represents lower alkyl or lower alkoxy, and X" represents an iodide, bromide, of trifluoromethylsulfonyloxy moiety and $R_8$ represents a protected alcohol or aldehyde. For alcohols, suitable protecting groups include silyl ethers, benzyl ethers. Aldehydes, may be protected as their acetal derivatives. The compound of formula 12 can be converted to an aldehyde of formula 15 by convertional steps which, when $R_8$ is an alcohol, would involve protecting group removal, if necessary, followed by oxidation. Any of the common reagents for the selective oxidation of primary benzyl alcohols to aldehydes may be employed, for example, treatment with activated manganese dioxide in an inert solvent. In the case where $R_8$ represents a protected aldehyde, conversion to an aldehyde of formula 15 can be carried out by a suitable protecting group removal, for example hydrolysis of an acetal with dilute acid. Reaction of 15 to give a dehydroamino acid of formula 16 can be effected by treatment with a Wittig reagent of formula 17 in which $P_1'$ is lower alkoxycarbonyl or benzyloxycarbonyl and $P_2$ is as defined above. For example treatment of 15 with (±)-N-(benzyloxycarbonyl)-α-phosphonoglycine trimethyl ester in the presence of a suitable base for example tetramethylguanidine leads directly to a dehydroamino acid of formula 16, $P_2$=methyl and $P_1'$=benzyloxycarbonyl. Enantioselective reduction of 16 to the L-amino acid 18 can be effected by use of a number of reducing agents suitable for the purpose, for example, the recently described ethyl-DuPHOS rhodium reagent (Burk, M. J., Feaster, J. E.; Nugent, W. A.; Harlow, R. L. *J. Am. Chem. Soc.* 1993, 115, 10125) using essentially the literature procedure. Further conversion of 18 to the compounds of the invention can be carried out using the general procedures discussed above.

Reaction Scheme 5

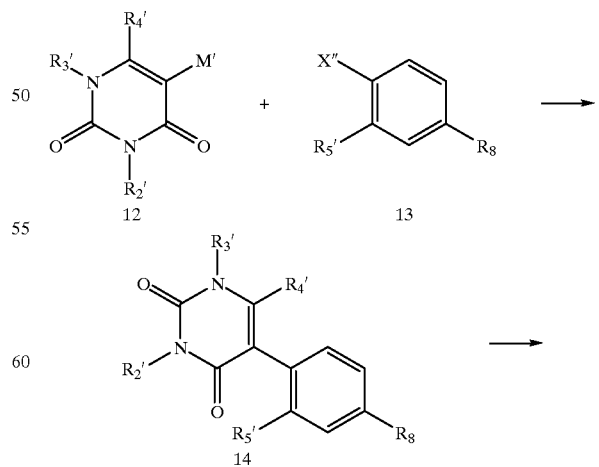

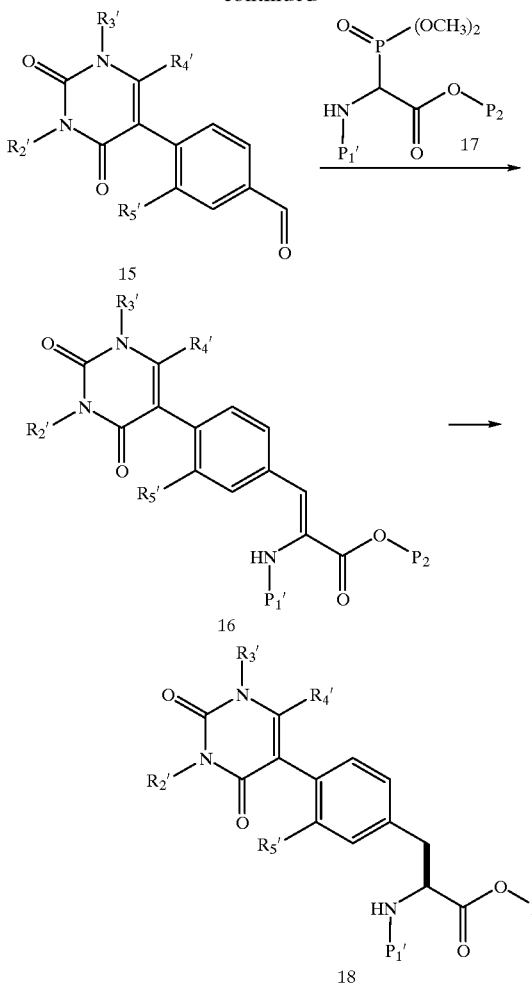

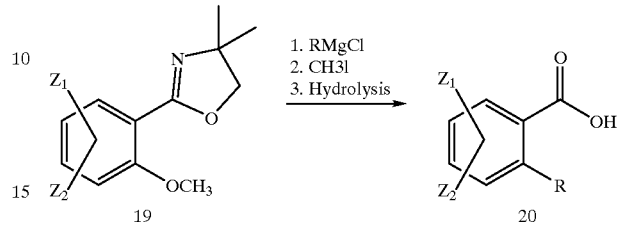

Reaction Scheme 6

In one embodiment, the N-acyl group, $R_1'$ of structure 11, is derived from a 2-subsituted benzoic acid. Appropriate 2-substituted benzoic acids are either commercially available or can be prepared by conventional means. For example ortho-substituted aryl iodides or triflates may be carbonylated in the presence of carbon monoxide and a suitable palladium catalyst. The preparation of such iodide or triflate intermediates is dependent on the particular substitution pattern desired and they may be obtained by direct iodination or diazotization of an aniline followed by treatment with a source of iodide for example, potassium iodide. Triflates may be derived from the corresponding phenols by conventional means such as by treatment with trifluoromethane sulfonic anhydride in the presence of a base such as triethylamine or diisopropylethylamine in an inert solvent. As shown in Reaction Scheme 6, one other means of obtaining ortho-substituted benzoic acids involves treatment of an 2-methoxyphenyloxazoline derivative such as compound 19, $Z_1$ and $Z_2$=hydrogen, alkyl, chloro, perfluoroalkyl, lower alkoxy with an alkyl Grignard reagent followed by hydrolysis of the oxazoline ring following the general procedure described by Meyers, A. I., Gabel, R., Mihelick, E. D, *J. Org. Chem.* 1978, 43, 1372–1379, to give an acid of formula 20. 2- or 2,6-Disubstituted benzonitriles also serve as convenient precursors to the corresponding benzoic acids. In the case of highly hindered nitrites, for example 2-chloro-6-methylbenzonitrile, conventional hydrolysis under acidic or basic conditions is difficult and better results are obtained by DIBAL reduction to the corresponding benzaldehyde followed by oxidation using a chromium based oxidizing reagent. Other methods are exemplified in Chen, et al., WO 9910312.

Referring now to Reaction Scheme 7, cyclic acids of formula 23 are known compounds or can be prepared using standard methodologies. For the preparation of substituted alkyl- or cycloalkylcarboxylic acids, alkylation reactions can be employed using an alkali metal dianion of the acid or monoanion of the corresponding ester. For example, a cycloalkyl carboxylic acid ester of formula 21 can be treated with a strong base, for example, lithium diisopropylamide in an inert solvent, for example THF followed by addition of group $R_{41}$-Lv wherein $R_{41}$, represents a desired side chain, such as a substituted benzyl, lower alkyl, lower alkoxy alkyl, azidolower alkyl and the like and Lv represents a leaving group such as a bromide, iodide, mesylate or similar group known to participate in ester enolate alkylation reactions. The product ester 22 may be hydrolyzed to the acid 23 using alkali metal hydroxide in a suitable solvent, for example aqueous alcohol. Depending on the nature of $R_{41}$, and the eventual target, the compound 23 may be coupled to an amine such as compound 1 and converted to the target directly or $R_{41}$, may be subject to further manipulation at a suitable point in the synthesis. For example, if $R_{41}$ is an azido lower alkyl moiety, the azide may be reduced using for example a trialkyl phosphine reagent followed by functionalization of the product amine by alkylation, acylation, sulfonylation and related procedures well known to those skilled in the art. If $R_{41}$ incorporates a leaving group, for example, a termninal bromine atom, this group may be displaced by an appropriate nucleophile, for example, sodium methyl mercaptide to give in this case, a thioether which may be the desired product or can be itself further manipulated, for example by oxidation to a sulfoxide or sulfone using standard reaction conditions. Other nucleophiles which may be employed to produce intermediates leading to compounds of this invention include: sodium cyanide, sodium methoxide, sodium azide, morpholine and others. When $R_{41}$, incorporates a ketal group, this group may be hydrolzyed at a convenient point in the synthesis to provide a keto group. This group in turn may be further manipulated, for example by reduction to an alcohol or conversion to derivative such as an oxime.

Examples of the application of these methods to the synthesis of compounds of formula 23 are provided in Chen, et al. WO 9910313.

Reaction Scheme 7

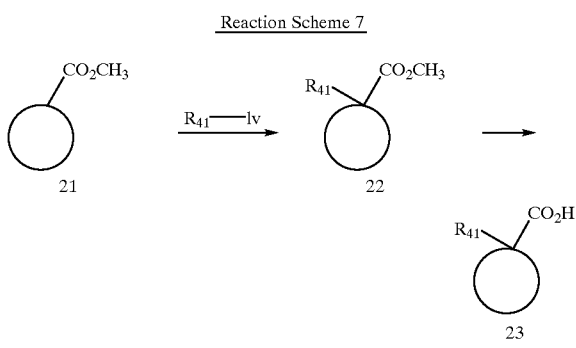

In general, ortho-substituted aromatic acids needed for the preparation of compounds in which $R^1$=Y-1 can be prepared as exemplified in Chen, et al., WO9910312.

For the synthesis of 2-chloro-6-alkylbenzoic acids of formula 28, wherein R43 is lower alkyl, the procedure described in Reaction Scheme 8 is particularly suitable. Thus, a commercially available aldehyde of formula 24 is converted to the imine 25 wherein R42 is lower alkyl, preferably butyl, by treatment with butylamine in an inert, hydrophobic organic solvent, for example heptane. The resulting compound of formula 25 is treated with an excess of a Grignard derivative 26 in an inert solvent, for example THF, followed by acid treatment during the workup to give an aldehyde of formula 27. Oxidation of 27 to an acid of formula 28 can be carried out by conventional means, for example by treatment of a solution of 27 in a suitable solvent such as aqueous acetonitrile with sodium chlorite and 30% hydrogen peroxide at or below room temperature.

Reaction Scheme 8

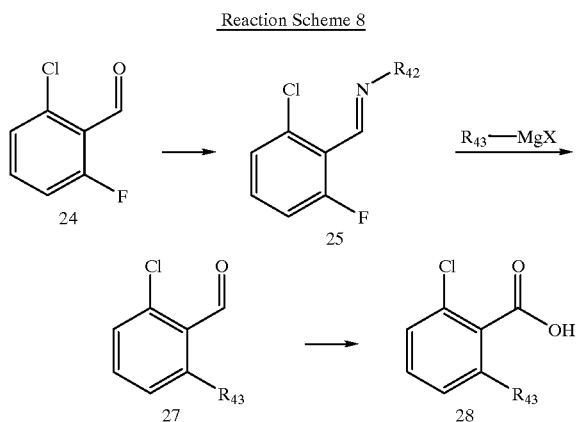

It may be desirable to prepare prodrug esters of the compounds of this invention for which it would be more convenient to introduce the ester moiety at the end of the synthesis. For this purpose, a variety of common techniques for the formation of esters from carboxylic acids may be employed. Typical methods which may be useful would include, coupling of an alcohol to the carboxylic acid in the presence of acid, for example hydrochloric acid, a procedure commonly known as a Fisher esterification. Alternatively, a diimide mediated coupling between the carboxylic acid and an alcohol may be employed with the optional use of a promoter such as 4,4-dimethylaminopyridine. A typical diimide is dicyclohexylcarbodiimide. Another alternative is to treat the carboxylic acid with a reactive alkyl halide, for example, an alkyl iodide or an acyloxymethyl chloride in the presence of a base, for example sodium bicarbonate and an inert solvent, for example DMF. The particular choice of method will be determined by the nature of the particular combination of carboxylic acid and desired ester moiety and will be apparent to one skilled in the art. Ester groups which may constitute prodrugs may be introduced at any convenient point in the synthesis. For example the group $P_2$ in formula 1 may represent a desirable prodrug ester and be retained in the final product.

The preferred compounds of this invention are compounds of formula Ia. Formula Ia is the same as Formula I as follows:

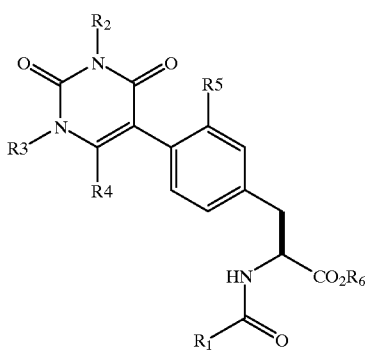

wherein $R_1$ is a group of the formula Y-1

Y-1

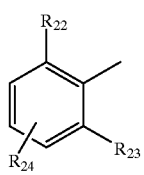

wherein $R_{22}$ and $R_{23}$ are independently hydrogen, lower alkyl, lower alkoxy, cycloalkyl, aryl, arylalkyl, nitro, cyano, lower alkylthio, lower alkylsulfinyl, lower alkyl sulfonyl, lower alkanoyl, halogen, or perfluorolower alkyl and at least one of $R_{22}$ and $R_{23}$ is other than hydrogen; and $R_{24}$ is hydrogen, lower alkyl, lower alkoxy, aryl, nitro, cyano, lower alkyl sulfonyl, or halogen; or $R_1$ is a five or six membered heteroaromatic ring bonded via a carbon atom to the amide carbonyl wherein said ring contains one, two or three heteroatoms selected from the group consisting of N, O and S and one or two atoms of said ring are independently substituted by lower alkyl, cycloalkyl, halogen, cyano, perfluoroalkyl, or aryl and at least one of said substituted atoms is adjacent to the carbon atom bonded to the amide carbonyl; or $R_1$ is a group of formula Y-3 which is a 3–7 membered ring of the formula:

Y-3

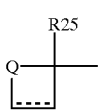

wherein $R_{25}$ is lower alkyl, unsubstituted or fluorine substituted lower alkenyl, or a group of formula $R_{26}$—$(CH_2)_e$—, $R_{26}$ is aryl, heteroaryl, azido, cyano, hydroxy, lower alkoxy, lower alkoxycarbonyl, lower alkanoyl, lower alkylthio, lower alkyl sulfonyl, lower alkyl sulfinyl, perfluoro lower alkanoyl, nitro, or $R_{26}$ is a group of formula —NR$_{28}$R$_{29}$, wherein R$_{28}$ is hydrogen or lower alkyl, R$_{29}$ is hydrogen, lower alkyl, lower alkoxycarbonyl, lower alkanoyl, aroyl, perfluoro lower alkanoylamino, lower alkyl sulfonyl, lower alkylamninocarbonyl, arylaminocarbonyl; or R$_{28}$ and R$_{29}$, taken together with the attached nitrogen atom, form a 4, 5 or 6-membered saturated heterocyclic ring optionally containing one additional heteroatom selected from O, S, and N—R$_{40}$, Q is —(CH$_2$)$_f$O—, —(CH$_2$)$_f$S—, —(CH$_2$)$_f$N(R$_{27}$)—, —(CH$_2$)$_f$—, R$_{27}$ is H, lower alkyl, aryl, lower alkanoyl, aroyl or lower alkoxycarbonyl, R40 is H, lower alkyl, aryl, lower alkanoyl, aroyl or lower alkoxycarbonyl, the carbon atoms in the ring are unsubstituted or substituted by lower alkyl or halogen, e is an integer from 0 to 4, and f is an integer from 0 to 3. In Formula Ia, R$_2$ is hydrogen or lower alkyl, substituted lower alkyl, or aryl, R$_3$ is hydrogen or lower alkyl, substituted lower alkyl, or aryl, R$_4$ is hydrogen, lower alkyl, perfluoro lower alkyl, or aryl, R$_5$ is hydrogen, lower alkyl, chloro, or lower alkoxy. As in Formula I, R$_6$ is hydrogen, lower alkyl, lower alkyl carbonyloxy lower alkyl, substituted lower alkyl,or R$_6$ is a group of formula P-3. Preferably, R$_4$ is hydrogen, lower alkyl, or perfluoro lower alkyl.

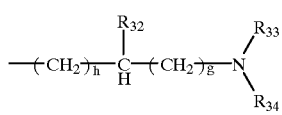

P-3 wherein R$_{32}$ is hydrogen or lower alkyl; R$_{33}$ is hydrogen, lower alkyl, aryl; R$_{34}$ is hydrogen or lower alkyl; h is an integer from 0 to 2; g is an integer from 0 to 2; the sum of h and g is 1 to 3;or or R$_6$ is a group of formula P-4:

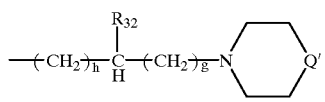

P-4 wherein R$_{32}$, g, and h are as previously defined; Q' is O, S, —(CH$_2$)$_f$—, or a group of the formula N—R$_{35}$; wherein R$_{35}$ is hydrogen, lower alkyl, lower alkanoyl, lower alkoxycarbonyl; j is 0, 1 or 2, or its pharmaceutically acceptable salts.

Each of the compounds of this invention is also contemplated in its pharmaceutically acceptable salt form.

In a preferred embodiment of Formula I or Formula Ia, R$_1$ is a group of the formula Y-1 as defined in formula I and R$_{22}$ and R$_{23}$ are independently lower alkyl or halogen; and R$_{24}$ is hydrogen. In another preferred embodiment, R$_1$ is a group of the formula Y-1 as defined in formula I and R$_{22}$ and R$_{23}$ are independently hydrogen or halogen; and R$_{24}$ is lower alkoxy.

Another preferred embodiment of Formula I or Formula Ia features R$_1$ as a group of formula Y-3 as defined in formula I where R$_{25}$ is a group of formula R$_{26}$—(CH$_2$)$_e$—, wherein R$_{26}$ is lower alkoxy, Q is —(CH$_2$)$_f$—, e is an integer from 0 to 4, and f is an integer from 0 to 3.

Also part of this invention is a compound of the formula Ib:

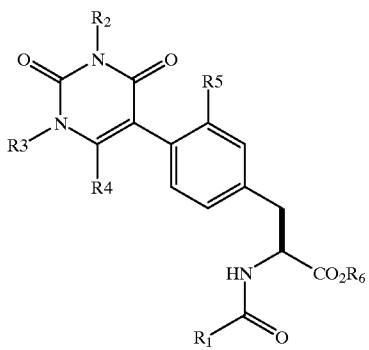

where R$_1$ is as defined in formula I, R$_2$ is lower alkyl; R$_3$ is lower alkyl; R$_4$ is hydrogen, perfluoro lower alkyl, or lower alkyl, R$_5$ is hydrogen or lower alkyl; and R$_6$ is hydrogen, lower alkyl, lower alkyl carbonyloxylower alkyl, a group of formula P-3 as defined in formula I or a group of formula P-4 as defined in formula I. It is preferred that R$_1$ is a group of the formula Y-1 as defined in formula I where R$_{22}$ and R$_{23}$ are independently perfluoro lower alkyl, lower alkyl, or halogen; and R$_{24}$ is hydrogen.

When R$_1$ is a group of the formula Y-1 as defined in the preceding paragraph, it is preferred that i) R$^2$ and R$^3$ are lower alkyl; R$^4$ is hydrogen or lower alkyl, and R$_5$ and R$_6$ are hydrogen, or ii) R$^2$ and R$^3$ are lower alkyl; R$^4$ is hydrogen or lower alkyl, R$_5$ is hydrogen, and R$_6$ is hydrogen, lower alkyl, lower alkyl carbonyloxy lower alkyl, or R$_6$ is a group of formula P-3 as defined in formula I or R$_6$ is a group of formula P-4 as defined in formula I(preferably R$_{35}$ is hydrogen), especially where R$_6$ is lower alkyl, lower alkyl carbonyloxy lower alkyl, a group of the formula P-3 wherein R$^{32}$ is hydrogen; R$^{33}$ and R$^{34}$ are lower alkyl; h is 1; and g is 0, or a group of the formula P-4 wherein R$^{32}$ is hydrogen; h is 1; g is 0; and Q' is O, or iii) R$^2$ and R$^3$ are lower alkyl; R$^4$ is perfluoro lower alkyl, and R$_5$ and R$^6$ are hydrogen. or iv) R$^2$ and R$^3$ are lower alkyl; R$^4$ is hydrogen; R$^5$ is lower alkyl, and R$^6$ is hydrogen.

In compounds of this invention of the formula Ib,

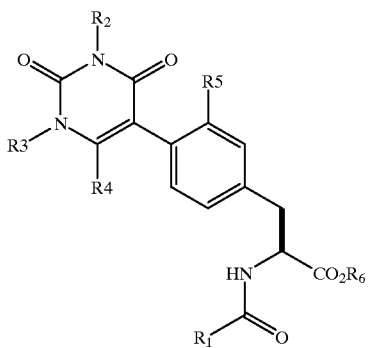

where R$_1$ is as defined in formula I, R$_2$ is lower alkyl; R$_3$ is lower alkyl; R$_4$ is hydrogen, perfluoro lower alkyl, or lower alkyl, R$_5$ is hydrogen or lower alkyl; and R$_6$ is hydrogen, lower alkyl, lower alkyl carbonyloxy lower alkyl, a group of formula P-3 as defined in formula I or a group of formula P-4 as defined in formula I (preferably R$_{35}$ is hydrogen), it is also preferred that R$_1$ is a group of formula Y-3 as defined in formula I, where R$_{25}$ is a group of formula R$_{26}$—(CH$_2$)$_e$—, wherein R$_{26}$ is lower alkoxy, Q is —(CH$_2$)$_f$—, e is an integer from 0 to 4, and f is an integer from 0 to 3. In such compounds, it is preferred that $R^2$ and $R^3$ are lower alkyl, $R^4$ is hydrogen or lower alkyl; and $R^5$ and $R^6$ are hydrogen.

In compounds of this invention of the formula Ib:

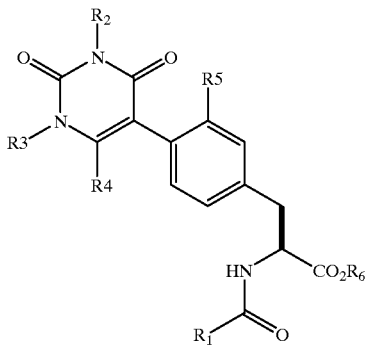

where $R_1$ is as defined in formula I, $R_2$ is lower alkyl; $R_3$ is lower alkyl; $R_4$ is hydrogen, perfluoro lower alkyl, or lower alkyl, $R_5$ is hydrogen or lower alkyl; and $R_6$ is hydrogen, lower alkyl, lower alkyl carbonyloxy lower alkyl, a group of formula P-3 as defined in formula I or a group of formula P-4 as defined in formula I, it is particularly preferred that $R_2$ and $R_3$ are lower alkyl; and $R_4$, $R_5$ and $R_6$ are hydrogen, especially where $R_1$ is a group of the formula Y-1 as defined in formula I, preferably where $R_{22}$ and $R_{23}$ are independently lower alkyl or halogen; and $R_{24}$ is hydrogen or where $R_{22}$ and $R_{23}$ are independently hydrogen or halogen; and $R_{24}$ is lower alkoxy.

In the compound of the preceding paragraph where $R_2$ and $R_3$ are lower alkyl; and $R_4$, $R_5$ and $R_6$ are hydrogen it is also preferred that $R_1$ is a five or six membered heteroaromatic ring bonded via a carbon atom to the amide carbonyl wherein said ring contains one, two or three heteroatoms selected from the group consisting of N, O and S and one or two atoms of said ring are independently substituted by lower alkyl, cycloalkyl, halogen, cyano, perfluoroalkyl, or aryl and at least one of said substituted atoms is adjacent to the carbon atom bonded to the amide carbonyl.

In the compound of the above paragraph where $R_2$ and $R_3$ are lower alkyl; and $R_4$, $R_5$ and $R_6$ are hydrogen it is also preferred that $R_1$ is a group of formula the Y-3 as defined in formula I, preferably where $R_{25}$ is a group of formula $R_{26}-(CH_2)_e-$, wherein $R_{26}$ is lower alkoxy, Q is $-(CH_2)_f-$, e is an integer from 0 to 4, and f is an integer from 0 to 3.

A preferred embodiment of the present invention is a compound of the formula I:

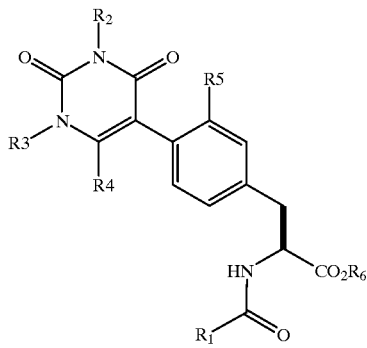

wherein $R_1$ is a group of the formula Y-1

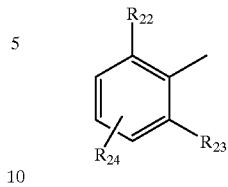

wherein $R_{22}$ and $R_{23}$ are independently hydrogen, lower alkyl, lower alkoxy, cycloalkyl, aryl, arylalkyl, nitro, cyano, lower alkylthio, lower alkylsulfinyl, lower alkyl sulfonyl, lower alkanoyl, halogen, or perfluorolower alkyl and at least one of $R_{22}$ and $R_{23}$ is other than hydrogen; and $R_{24}$ is hydrogen, lower alkyl, lower alkoxy, aryl, nitro, cyano, lower alkyl sulfonyl, or halogen; $R_2$ is lower alkyl; $R_3$ is lower alkyl; $R_4$ is hydrogen, or lower alkyl; $R_5$ is hydrogen; and $R_6$ is hydrogen.

A more preferred embodiment of the present invention is a compound of formula I above wherein $R_1$ is a group of the formula Y-1

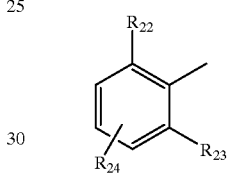

wherein $R_{22}$ and $R_{23}$ are independently hydrogen, lower alkyl or halogen, $R_{24}$ is hydrogen or lower alkoxy; $R_2$ is lower alkyl; $R_3$ is lower alkyl; $R_4$ is hydrogen, or lower alkyl; $R_5$ is hydrogen; and $R_6$ is lower alkyl, lower alkyl carbonyloxy lower alkyl, or preferably hydrogen.

Another preferred embodiment of the present invention is a compound of Formula I above wherein $R_1$ is a five or six membered heteroaromatic ring bonded via a carbon atom to the amide carbonyl wherein said ring contains one, two or three heteroatoms selected from the group consisting of N, O and S and one or two atoms of said ring are independently substituted by lower alkyl, cycloalkyl, halogen, cyano, perfluoroalkyl, or aryl and at least one of said substituted atoms is adjacent to the carbon atom bonded to the amide carbonyl; $R_2$ is lower alkyl; $R_3$ is lower alkyl; $R_4$ is hydrogen, perfluoro lower alkyl, or lower alkyl; $R_5$ is hydrogen; and $R_6$ is hydrogen.

Another preferred embodiment of the present invention is a compound of Formula I above wherein $R_1$ is a group of formula Y-3 which is a 3–7 membered ring of the formula:

wherein $R_{25}$ is lower alkyl, unsubstituted or fluorine substituted lower alkenyl, or a group of formula $R_{26}-(CH_2)_e-$, $R_{26}$ is aryl, heteroaryl, azido, cyano, hydroxy, lower alkoxy, lower alkoxycarbonyl, lower alkanoyl, lower alkylthio, lower alkyl sulfonyl, lower alkyl sulfinyl, perfluoro lower alkanoyl, nitro, or $R_{26}$ is a group of formula $-NR_{28}R_{29}$, wherein $R_{28}$ is hydrogen or lower alkyl, $R_{29}$ is hydrogen, lower alkyl, lower alkoxycarbonyl, lower alkanoyl, aroyl, perfluoro lower alkanoylamino, lower alkyl sulfonyl, lower alkylaminocarbonyl, arylaminocarbonyl; or $R_{28}$ and $R_{29}$, taken together with the attached nitrogen atom, form a 4, 5 or 6-membered saturated heterocyclic ring optionally containing one additional heteroatom selected from O, S, and N—$R_{40}$,Q is —(CH$_2$)$_e$O—, —(CH$_2$)$_e$S—, —(CH$_2$)$_e$N(R$_{27}$)—, —(CH$_2$)$_f$—, $R_{27}$ is H, lower alkyl, aryl, lower alkanoyl, aroyl or lower alkoxycarbonyl, $R_{40}$ is H, lower alkyl, aryl, lower alkanoyl, aroyl or lower alkoxycarbonyl the carbon atoms in the ring are unsubstituted or substituted by lower alkyl or halogen,e is an integer from 0 to 4, and f is an integer from 0 to 3; $R_2$ is lower alkyl; $R_3$ is lower alkyl; $R_4$ is hydrogen, perfluoro lower alkyl, or lower alkyl; $R_5$ is hydrogen; and R is hydrogen.

A more preferred embodiment of the present invention is a compound of formula I above wherein $R_1$ is a group of formula Y-3 which is a 3–7 membered ring of the formula:

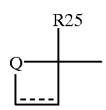

Y-3 wherein $R_{25}$ is a group of formula $R_{26}$—(CH$_2$)$_e$—, wherein $R_{26}$ is lower alkoxy, Q is —(CH$_2$)$_f$—, e is an integer from 0 to 4, and f is an integer from 0 to 3; $R_2$ is lower alkyl; $R_3$ is lower alkyl; $R_4$ is hydrogen, perfluoro lower alkyl, or lower alkyl; $R_5$ is hydrogen; and $R_6$ is hydrogen.

EXAMPLES

The Examples which follow are for purposes of illustration and are not intended to limit the invention in any way. General Methods: Melting points were taken on a Thomas-Hoover apparatus and are uncorrected. Optical rotations were determined with a Perkin-Elmer model 241 polarimeter. $^1$H-NMR spectra were recorded with Varian XL-200, Mecury-300 or Unityplus 400 MHz spectrometers, using tetramethylsilane (TMS) as internal standard. Electron impact (EI, 70 ev) and fast atom bombardment (FAB) mass spectra were taken on VG Autospec or VG 70E-HF mass spectrometers. Silica gel used for column chromatography was Mallinkrodt SiliCar 230–400 mesh silica gel for flash chromatography; columns were run under a 0–5 psi head of nitrogen to assist flow. Thin layer chromatograms were run on glass thin layer plates coated with silica gel as supplied by E. Merck (E. Merck # 1.05719) and were visualized by viewing under 254 nm UV light in a view box, by exposure to I2 vapor, or by spraying with either phosphomolybdic acid (PMA) in aqueous ethanol, or after exposure to Cl$_2$, with a 4,4'-tetramethyldiaminodiphenylmethane reagent prepared according to E. Von Arx, M. Faupel and M Brugger, *J. Chromatography*, 1976, 120, 224–228.

Reversed phase high pressure liquid chromatography (RP-HPLC)was carried out using a Rainin HPLC employing a 41.4×300 mm, 8 μM, Dynamax™ C-18 column at a flow of 49 mL/min employing a gradient of acetonitrile: water (each containing 0.75% TFA) typically from 5 to 95% acetonitrile over 35–40 min. HPLC conditions are typically described in the format (5-95-35-214); this refers to a linear gradient of from 5% to 95% acetonitrile in water over 35 min while monitoring the effluent with a UV detector at a wavelength of 214 nM.

Methylene chloride (dichloromethane), 2-propanol, DMF, THF, toluene, hexane, ether, and methanol, were Fisher or Baker reagent grade and were used without additional purification except as noted, acetonitrile was Fisher or Baker hplc grade and was used as is.

Definitions as used herein:

THF is tetrahydrofuran,

DMF is N,N-dimethylformamide,

DMA is N,N-dimethylacetamide

HOBT is 1-hydroxybenzotriazole,

BOP is [(benzotriazole-1-yl)oxy]tris-(dimethylamino) phosphonium hexafluorophosphate, HATU is O-(7-azabenzotriazol-1-yl)-1,1,3,3-tetramethyluronium hexafluorophosphate HBTU is O-benzotriazole-N,N,N',N',-tetramethyluronium hexafluorophosphate, DIPEA is diisopropylethylamine, DMAP is 4-(N,N-dimethylamino)pyridine DPPA is diphenylphosphoryl azide DPPP is 1,3-bis(diphenylphosphino)propane DBU is 1,8-diazabicyclo[5.4.0]undec-7-ene NaH is sodium hydride brine is saturated aqueous sodium chloride solution TLC is thin layer chromatography LDA is lithium diisopropylamide BOP-Cl is bis(2-oxo-3-oxazolidinyl)phosphinic chloride NMP is N-methylpyrrolidinone Lawesson's reagent is [2,4-bis(4-methoxyphenyl)-1,3-dithia-2,4-diphosphetane-2,4-disulfide]

NIS is N-iodosuccinic anhydride.

Silica gel chromatography on Biotage columns refers to use of a flash chromatography system supplied by the Biotage Division of the Dyax Corporation employing prepacked 40 g (40s columns), 90 g (40m columns) or 800 g (75 m columns). Elution is carried out with hexane-ethyl acetate mixtures under 10–15 psi nitrogen pressure.

Example 1

N-[(1,1-dimethylethoxy)carbonyl]-4-[(tributyl) stannyl]-L-phenylalanine methyl ester

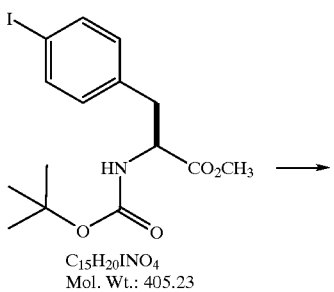

C$_{15}$H$_{20}$INO$_4$
Mol. Wt.: 405.23

-continued

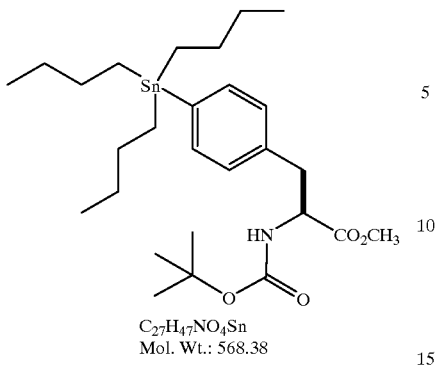

C27H47NO4Sn
Mol. Wt.: 568.38

A solution of N-[(1,1-dimethylethoxy)carbonyl]-4-iodo-L-phenylalanine methyl ester (5.3 g, 13 mmol) and hexabutylditin (27.5 mL, 54 mmol) in toluene (50 mL) was deoxygenated by alternately freezing the mixture in a liquid nitrogen bath under vacuum and thawing under argon (3 x). Tetrakis(triphenylphosphine)palladium was added (280 mg, 0.22 mmol) and the reaction mixture was heated to reflux for 45 min as the color changed from yellow to black. TLC (1:6 ethyl acetate:hexane) indicated the presence of some starting iodide and an additional portion (140 mg, 0.11 mmol) of the catalyst was added. Reflux was continued for 1 hr. The mixture was allowed to cool and was concentrated. The residue was taken up in hexane (200 mL) and triethylamine (30 mL), stirred for 30 min and was filtered. The filtrate was concentrated and was chromatographed over a dry silica gel column containing 150 g of silica gel and eluting with hexane followed by 1:6 ethyl acetate:hexanes to give N-[(1,1-dimethylethoxy)carbonyl]-4-[(tributyl)stannyl]-L-phenylalanine methyl ester (5.7 g, 77%) as a clear oil. LR(+)LSIMS (C27H47NO4Sn): m/z 1081 (2M-C4H9) 570 (M+H).

Example 2

N-[(2-chloro-6-methylphenyl)carbonyl]-4-(1,3-dimethyl-2,4-dioxo-5-pyrimidinyl)-L-phenylalanine a) Preparation of 5-iodo uracil

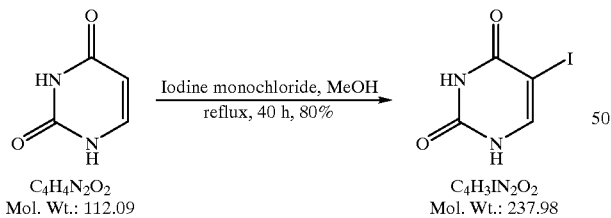

C4H4N2O2
Mol. Wt.: 112.09

C4H3IN2O2
Mol. Wt.: 237.98

A mixture of uracil (28.6 mmol, 3.2 g) and iodine monochloride (49.2 mmol, 7.988 g) in methanol (120 mL) was refluxed for 40 hr. The solvent was removed under vacuum and the residue was crystallized from ethanol:water (1:1, 150 mL) and stored in the refrigerator for 3 h. The resulting needles were collected by filtration and were washed with ethanol:water (1:1 mixture, 50 mL), water (30 mL), hexane (30 mL) and then dried in air to obtain 5.47 g (80%) of 5-iodo uracil as a white needles (mp 278–282° C., Lit. 274–276° C., *Synthetic communication* 1988, 18, 855–867). EI-HRMS m/e calcd for C4H3IN2O2 (M+) 237.9239, found 237.9244.

b) Preparation of 1,3-dimethyl-5-iodo uracil

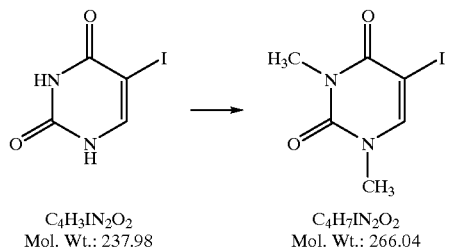

C4H3IN2O2
Mol. Wt.: 237.98

C4H7IN2O2
Mol. Wt.: 266.04

A mixture of 5-iodo uracil (22.2 mmol, 5.28 g) and powdered potassium carbonate (60 mmol, 10.3 g) in DMF (188 mL) was stirred for 24 h at room temperature and then methyl iodide (53.5 mmol, 3.33 mL) was added. Then, the reaction mixture was stirred for another 72 h at room temperature and was poured into water (150 mL) and ethyl acetate (150 mL). The layers were separated and the aqueous layer was extracted with ethyl acetate (2×100 mL). The combined extracts were washed with brine solution and dried over anhydrous magnesium sulfate. Filtration of the drying agent and concentration of the solvent gave crude solid which was crystallized from ethanol:water (3:1, 150:50 mL) and stored in the refrigerator overnight. The solids were collected by filtration and washed with ethanol:water mixture (3:1, 120 mL), water (30 mL), hexane (30 mL) and dried under vacuum to obtain 4.61 g (78%) of 1,3-dimethyl 5-iodo uracil as white needles (mp 226–228° C., Lit. 225–227° C., *Synthetic communication* 1988, 18, 855–867). EI-HRMS m/e calcd for C6H7IN2O2 (M+) 266.0021, found 266.0023.

c) Preparation of N-[(1,1-dimethylethoxy)carbonyl]-4-[1,3-dimethyl-2,4-dioxo-5-pyrimidinyl)]-L-phenylalanine methyl ester

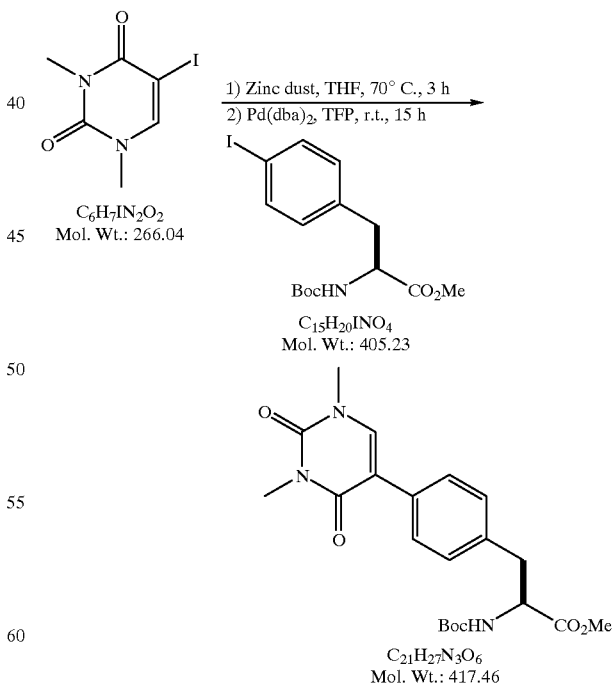

To a suspension of zinc dust (30 mmol, 2.0 g) in THF (3.0 mL) was added 1,2-dibromoethane (2.0 mmol, 0.174 mL) at room temperature. This suspension was heated to 60–65° C. with a heat gun until evolution of ethylene gas ceased (observed). This process was repeated three times. Then, the suspension was cooled to r.t. and trimethylchlorosilane (1.0 mmol, 0.15 mL) was added and the mixture was stirred for 10 min. A hot (the iodo compound was not very soluble in either solvent and it precipitated upon cooling to room temperature) solution of 5-iodo-1,3-dimethyluracil (11.0 mmol, 2.92 g) in THF (3.0 mL) and DMA (10 mL) was added to the zinc suspension. After addition, the mixture was heated to 73° C. The internal temperature of the reaction mixture rose to 77–78° C., due to the exothermic reaction. The reaction mixture was stirred at a bath temperature of 73° C. for 1.5 h and then was cooled to room temperature and stirred another 1.5 h. $^1$H-NMR of a hydrolysate of a 0.25 mL aliquot of the mixture indicated the presence of traces of starting material and iodolysis of a 0.25 mL aliquot of the mixture gave the iodide back. The reaction mixture was heated to 70° C. and stirred for another 30 min. The reaction mixture was diluted with THF (5 mL) after cooling to room temperature and the excess zinc was allowed to settle for 30–60 min. The above prepared zinc compound (5.5 mmol) was added to a suspension of Pd(dba)$_2$ (0.07 mmol, 40 mg), trifurylphosphine (TFP) (0.26 mmol, 66.6 mg) and Boc-4-iodo-L-phenylalanine methyl ester (4.5 mmol, 1.823 g) in THF (10 mL) at room temperature and the light yellow mixture was stirred for 15 h. The mixture was poured into a saturated ammonium chloride solution and was extracted with ethyl acetate (3×50 mL). The combined extracts were washed with brine solution and dried over anhydrous magnesium sulfate. Filtration of the drying agent and concentration of the solution gave the crude product which was purified by column chromatography to obtain 0.80 g (43%) of N-[(1,1-dimethylethoxy)carbonyl]-4-[1,3-dimethyl-2,4-dioxo-5-pyrimidinyl)]-L-phenylalanine methyl ester as a white solid: mp 65–69° C. EI-HRMS m/e calcd for $C_{21}H_{27}N_3O_6$ (M$^+$) 418.1978, found 418.1965.

d) Preparation of 4-(1,3-dimethyl-2,4-dioxo-5-pyrimidinyl)-L-phenylalanine methyl ester.

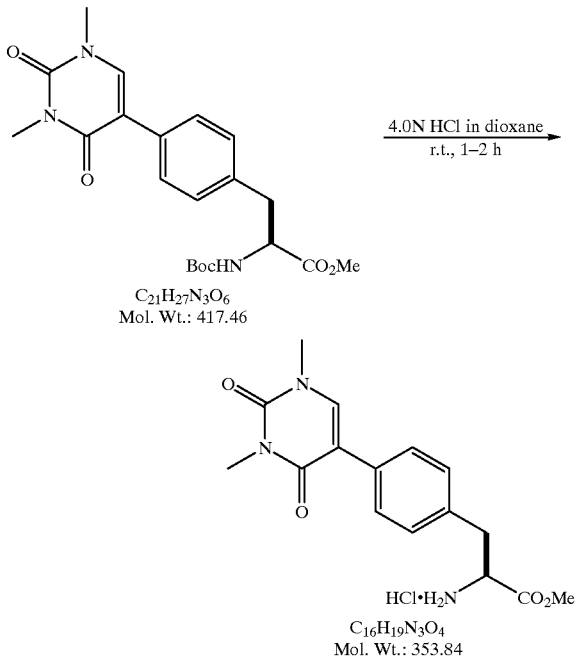

A solution of N-[(1,1-dimethylethoxy)carbonyl]-4-(1,3-dimethyl-2,4-dioxo-5-pyrimidinyl)-L-phenylalanine methyl ester (1.94 mmol, 0.811 g) in dioxane (5 mL) was treated with 4.0 N (5 mL, 20 mmol) hydrochloric acid in dioxane at room temperature and the solution was stirred for 0.5 h. By this time, a light yellow precipitate slowly formed. The solids were collected by filtration and were washed with hexane to afford 412 mg (60% yield), mp 187–193° C. The mother liquour was concentrated under vacuum and the residue was triturated with dichloromethane. The combined solids, which contained some starting material, were combined and dissolved in methanol. The major portion of the methanol was evaporated and dichloromethane was added to form a precipitate. The solids were collected and dried to obtain 330 mg (48%) of 4-(1,3-dimethyl-2,4-dioxo-5-pyrimidinyl)-L-phenylalanine methyl ester hydrochloride salt (mp 187–193° C.). EI-HRMS m/e calcd for $C_{16}H_{19}N_3O_4$ (M+H) 318.1454, found 318.1447.

e) Preparation of N-[(2-chloro-6-methylphenyl)carbonyl]-4-(1,3-dimethyl-2,4-dioxo-5-pyrimidinyl)-L-phenylalanine methyl ester

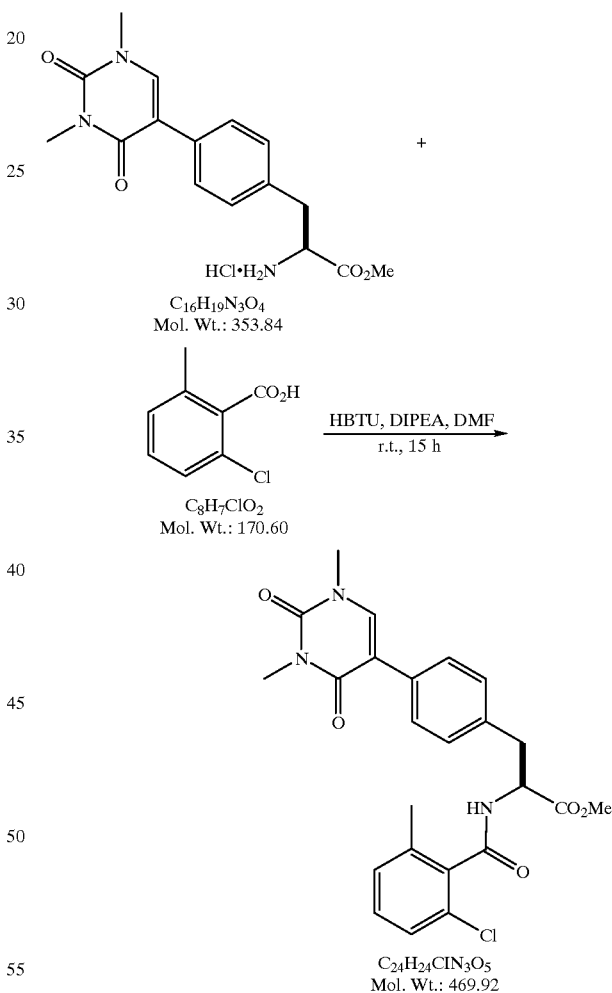

To a suspension 4-(1,3-dimethyl-2,4-dioxo-5-pyrimidinyl)-L-phenylalanine methyl ester hydrochloride salt (0.5 mmol, 0.180 g), 2-chloro-6-methylbenzoic acid (0.55 mmol, 0.084 g) and HBTU (0.6 mmol, 0.227 g) in DMF (4 mL) was added diisopropylethylamine (3.0 mmol, 0.52 mL) at room temperature. After 1 min, everything went into solution and the yellow clear solution was stirred 15 h at room temperature. By this time, it turned to a brown solution was diluted with ethyl acetate (25 mL). The ethyl acetate layer was washed successively with water (2×20 mL), saturated sodium bicarbonate solution (25 mL), and brine solution (25 mL) and was dried over anhydrous magnesium sulfate. Filtration of the drying agent and concentration of the solvent gave the crude product which was purified by silica gel column chromatography to afford 151.5 mg (72% yield) of N-[(2-chloro-6-methylphenyl)carbonyl]-4-(1,3-dimethyl-2,4-dioxo-5-pyrimidinyl)-L-phenylalanine methyl ester as a white solid: mp 155–157° C. EI-HRMS m/e calcd for $C_{24}H_{24}N_3O_5Cl$ ($M^+$) 470.1483, found 470.1484.

f) Preparation of N-[(2-chloro-6-methylphenyl)carbonyl]-4-(1,3-dimethyl-2,4-dioxo-5-pyrimidinyl)-L-phenylalanine

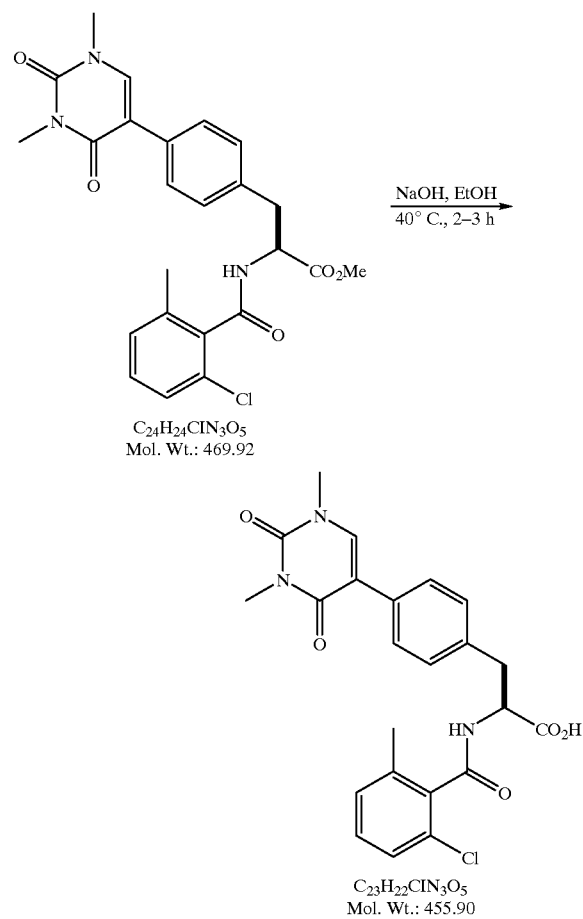

To a suspension of N-[(2-chloro-6-methylphenyl) carbonyl]-4-(1,3-dimethyl-2,4-dioxo-5-pyrimidinyl)-L-phenylalanine methyl ester (0.278 mmol, 131 mg) in ethanol (4 mL) was added aqueous 1.0 N sodium hydroxide (3 mL) at room temperature. The mixture was heated to 40–45° C. and the resulting clear solution was stirred for 2–3 h. The ethanol was removed under reduced pressure and the residue was diluted with water (20 mL) and NaOH (3 mL, 1.0N) to dissolve the sodium salt. The aqueous solution was washed with ether (50 mL) to remove any neutral impurities. The aqueous layer was acidified with 1.0 N HCl and the product was extracted into ethyl acetate (2×50 mL). The combined organic extracts were washed with brine solution and were dried over anhydrous magnesium sulfate. Filtration of the drying agent and concentration of the filtrate afforded 107 mg (85%) of N-[(2-chloro-6-methylphenyl)carbonyl]-4-(1,3-dimethyl-2,4-dioxo-5-pyrimidinyl)-L-phenylalanine as a white solid: mp 234–236° C. EI-HRMS m/e calcd for $C_{23}H_{22}N_3O_5Cl$ (M+H) 456.1326, found 456.1326.

Example 3

Preparation of 4-[(1,3-dimethyl-2,4-dioxo-5-pyrimidinyl)]-N-[[1-(2-methoxyethyl)cyclopentyl]carbonyl]-L-phenylalanine

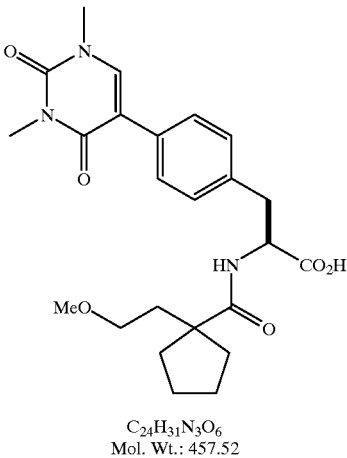

$C_{24}H_{31}N_3O_6$
Mol. Wt.: 457.52

4-(1,3-dimethyl-2,4-dioxo-5-pyrimidinyl)]-N-[[1-(2-methoxyethyl)cyclopentyl]carbonyl]-L-phenylalanine was prepared from 4-(1,3-dimethyl-2,4-dioxo-5-pyrimidinyl)]-L-phenylalanine methyl ester and 1-(2-methoxyethyl) cyclopentane carboxylic acid (see WO 9910312) using the general procedures described in example 2. EI-HRMS m/e calcd for $C_{24}H_{31}N_3O_5$ (M+H) 458.2292, found 458.2279.

Example 4

Preparation of N-[(2-bromo-6-methylphenyl) carbonyl]-4-(1,3-dimethyl-2,4-dioxo-5-pyrimidinyl)-L-phenylalanine

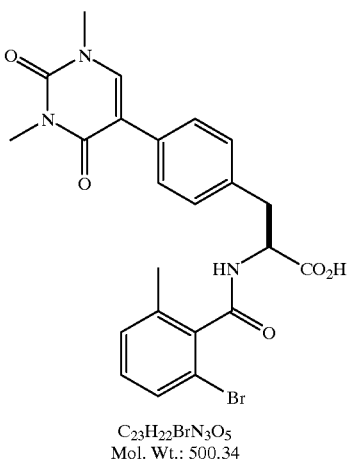

$C_{23}H_{22}BrN_3O_5$
Mol. Wt.: 500.34

N-[(2-bromo-6-methylphenyl)carbonyl]-4-(1,3-dimethyl-2,4-dioxo-5-pyrimidinyl)-L-phenylalanine was prepared from 4-(1,3-dimethyl-2,4-dioxo-5-pyrimidinyl)]-L-phenylalanine and 2-bromo-6-methylbenzoic acid using the general procedures described in example 2. EI-HRMS m/e calcd for $C_{23}H_{22}N_3O_5Br$ (M+H) 500.0822, found 500.0825.

Example 5

Preparation of N-[(2-bromo-5-methoxyphenyl)carbonyl]-4-[1,3-dimethyl-2,4-dioxo-5-pyrimidinyl]-L-phenylalanine

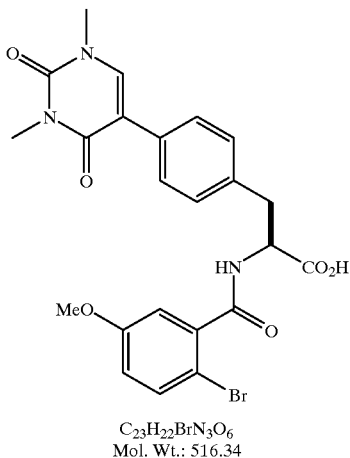

C$_{23}$H$_{22}$BrN$_3$O$_6$
Mol. Wt.: 516.34

N-[(2-bromo-5-methoxyphenyl)carbonyl]-4-[1,3-dimethyl-2,4-dioxo-5-pyrimidinyl]-L-phenylalanine was prepared from 4-[1,3-dimethyl-2,4-dioxo-5-pyrimidinyl]-L-phenylalanine methyl ester and 2-bromo-5-methoxybenzoic acid using the general procedures described in example 2. EI-HRMS m/e calcd for C$_{23}$H$_{22}$N$_3$O$_6$Br (M+H) 516.0770, found 516.0780.

Example 6

N-[(2,6-dichlorophenyl)carbonyl]-4-(1,3,6-trimethyl-2,4-dioxo-5-pyrimidinyl)-L-phenylalanine a) Preparation of 5-iodo-1,3,6-trimethyl uracil

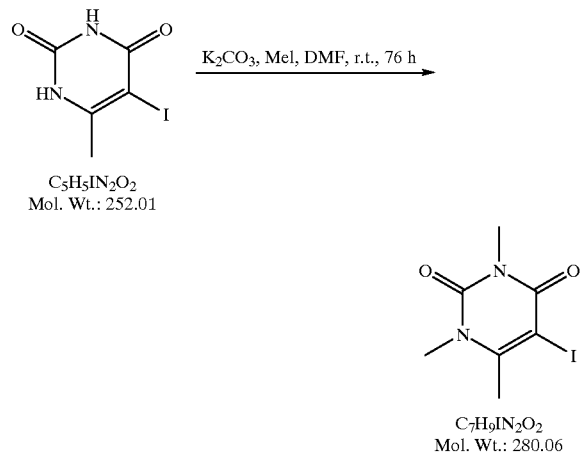

A mixture of 5-iodo-6-methyl uracil (22.18 mmol, 5.58 g) and powdered potassium carbonate (60 mmol, 8.29 g) in DMF (188 mL) was stirred for 24 h at room temperature and then methyl iodide (90.6 mmol, 3.33 mL) was added. The reaction mixture was stirred for another 76 h at room temperature and was poured into water (150 mL) and ethyl acetate (150 mL). The layers were separated and the aqueous layer was extracted with ethyl acetate (2×100 mL). The combined extracts were washed with brine solution (150 mL) and dried over anhydrous magnesium sulfate. Filtration of the drying agent and concentration of the solvent gave crude solid which was crystallized from ethanol:water (3:1, 150:50 mL) and stored in the refrigerator overnight. The solids were collected by filtration and washed with ethanol:water (3:1, 120 mL), water (30 mL), hexanes (30 ML) and dried under high vacuum to obtain 5.8 g (93% yield) of 5-iodo-1,3,6-trimethyl uracil as a white solid: mp 155–157° C. EI-HRMS m/e calcd for C$_7$H$_9$IN$_2$O$_2$ (M$^+$) 279.9709, found 279.9709.

b) Preparation of N-[(1,1-dimethylethoxy)carbonyl]-4-(1,3,6-trimethyl-2,4-dioxo-5-pyrimidinyl)-L-phenylalanine methyl ester

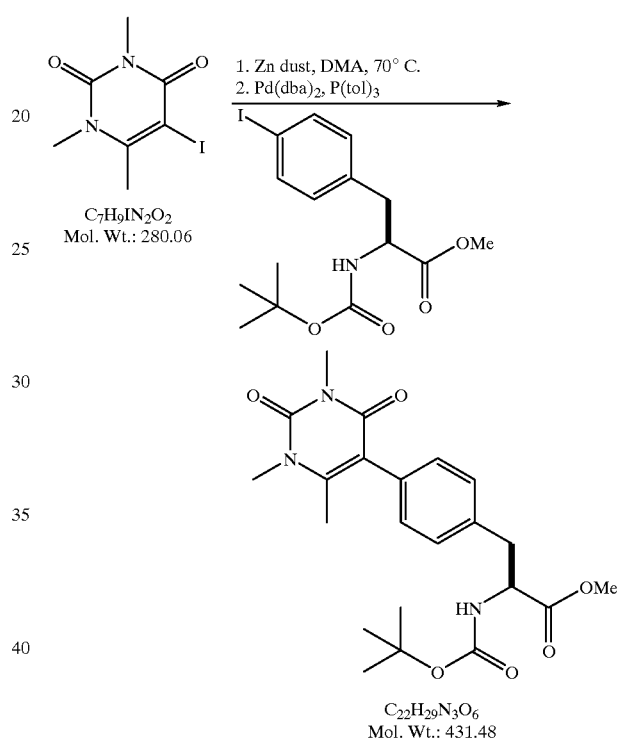

To a suspension of zinc dust (800 mmol, 52.29 g) in THF (26.0 mL) was added 1,2-dibromoethane (53.2 mmol, 4.58 mL) at room temperature. This suspension was heated to 60–65° C. with a heat gun until evolution of ethylene gas ceased (observed). The suspension was cooled to room temperature, trimethylchlorosilane (26.6 mmol, 3.38 mL) was added and the mixture was stirred for 15 min. A suspension of 5-iodo-1,3,6-trimethyl uracil (266 mmol, 74.6 g) in DMA (225 mL) was warmed to obtain a clear solution and was added in one portion to the reaction mixture. After addition, the mixture was heated to 70° C. The internal temperature of the reaction mixture rose to 80–85° C. due to the exothermic reaction. The reaction mixture was stirred at 70° C. for 3–4 h at which time TLC of an aliquot which had been quenched with saturated ammonium chloride indicated the absence of starting material. The reaction mixture was diluted with THF (140 mL), was cooled to room temperature and the excess zinc dust was allowed to settle over 2–3 h. This solution containing the zinc compound (266 mmol) was added to a solution of Pd(dba)$_2$ (8 mmol, 4.6 g), tri-o-tolylphosphine [P(Tol)$_3$] (29.6 mmol, 9.0 g) and N-[(1,1- dimethylethoxy)carbonyl]-4-iodo-L-phenylalanine methyl ester (186 mmol, 75.56 g) in THF (280 mL) at room temperature and the light yellow mixture was stirred for 48 h at 50–55° C. The reaction mixture was poured into a saturated ammonium chloride solution and was extracted with ethyl acetate (3×750 mL). The combined extracts were washed with brine solution (1.5 L) and dried over anhydrous magnesium sulfate. Filtration of the drying agent and concentration gave the crude product which was purified by silica gel column chromatography using a Biotage (75m) column to obtain 57.88 g (72% yield) of N-[(1,1-dimethylethoxy)carbonyl]-4-(1,3,6-trimethyl-2,4-dioxo-5-pyrimidinyl)-L-phenylalanine methyl ester as an amorphous white solid. EI-HRMS m/e calcd for $C_{22}H_{29}N_3O_6$ (M+) 431.2056, found 431.2054.

c) Preparation of 4-(1,3,6-trimethyl-2,4-dioxo-5-pyrimidinyl)-L-phenylalanine methyl ester hydrochloride salt

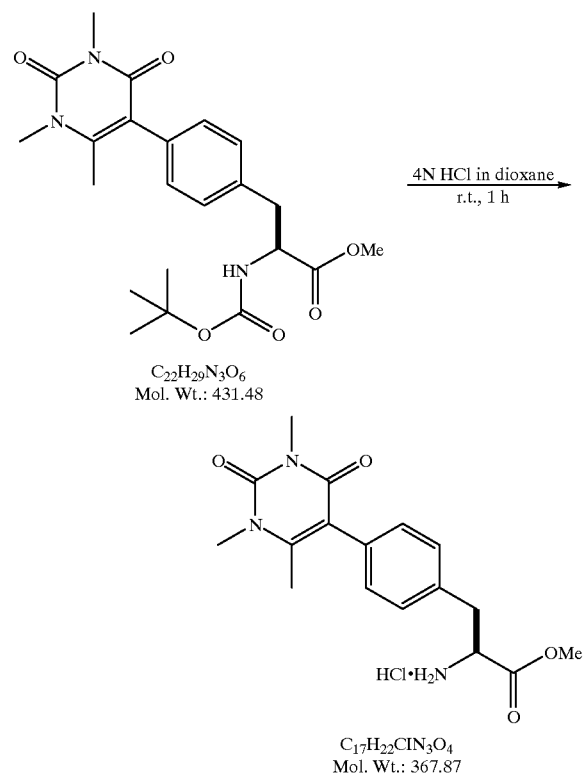

A portion of the solid N-[(1,1-dimethylethoxy)carbonyl]-4-(1,3,6-trimethyl-2,4-dioxo-5-pyrimidinyl)-L-phenylalanine methyl ester (17.15 mmol, 7.4 g) obtained above was treated with 4N hydrochloric acid in dioxane (68 mmol, 17 mL) at room temperature and the solution was stirred for 1 h as a white precipitate formed. The mixture was diluted with diethyl ether and the supernatant was decanted and the residue was dried first on the rotary evaporator and then under high vacuum to afford 6.28 g (99% yield) of 4-(1,3,6-trimethyl-2,4-dioxo-5-pyrimidinyl)-L-phenylalanine methyl ester hydrochloride salt as an amorphous yellow solid. FAB-HRMS m/e calcd for $C_{17}H_{21}N_3O_4$ (M+H) 332.1610, found 332.1617.

d) Preparation of N-[(2,6-dichlorophenyl)carbonyl]-4-(1,3,6-trimethyl-2,4-dioxo-5-pyrimidinyl)-L-phenylalanine methyl ester

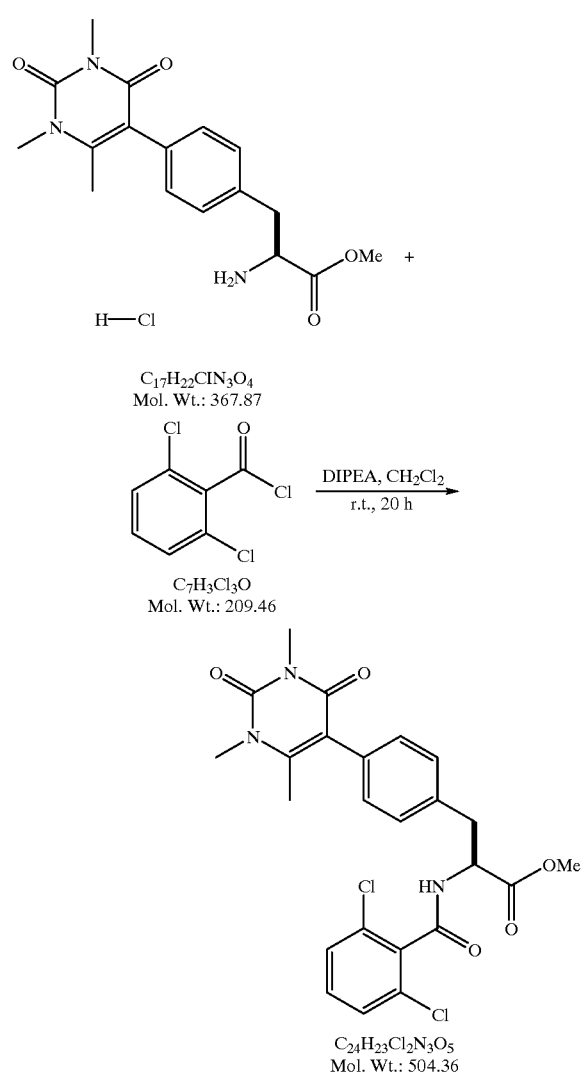

To a suspension of 4-(1,3,6-trimethyl-2,4-dioxo-5-pyrirnidinyl)-L-phenylalanine methyl ester hydrochloride salt (3.12 mmol, 1.15 g) and 2,6-dichlorobenzoyl chloride (3.51 mmol, 0.735 g) in dichloromethane (40 mL) was added diisopropylethylamine (9.36 mmol, 1.63 mL) at room temperature. After 1 min, everything went into solution and the clear yellow solution was stirred for 20 h at room temperature. The resulting brown solution was diluted with dichloromethane (50 mL). The dichloromethane layer was washed successively with 1N hydrochloric acid (2×50 mL), saturated sodium bicarbonate solution (50 mL), and brine solution (50 mL) and was dried over anhydrous magnesium sulfate. Filtration of the drying agent and concentration of the solvent gave the crude product which was purified by silica gel chromatography using a Biotage (40m) column to afford 1.46 g (93% yield) of N-[(2,6-dichlorophenyl)carbonyl]-4-(1,3,6-trimethyl-2,4-dioxo-5-pyrimidinyl)-L-phenylalanine methyl ester as an amorphous white solid.

FAB-HRMS m/e calcd for $C_{24}H_{23}Cl_2N_3O_5$ (M+H) 504.1093, found 504.1083.

e) Preparation of N-[(2,6-dichlorophenyl)carbonyl]-4-(1,3,6-trimethyl-2,4-dioxo-5-pyrimidinyl)-L-phenylalanine

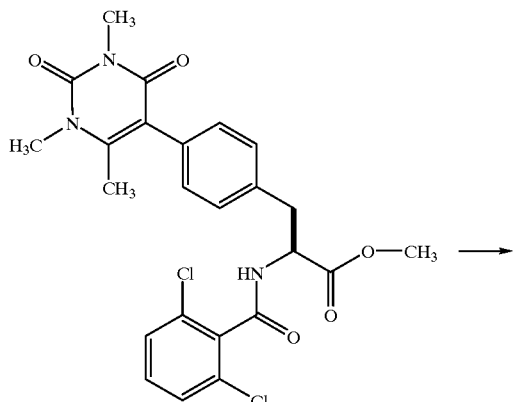

C$_{24}$H$_{23}$Cl$_2$N$_3$O$_5$
Mol. Wt.: 504.36

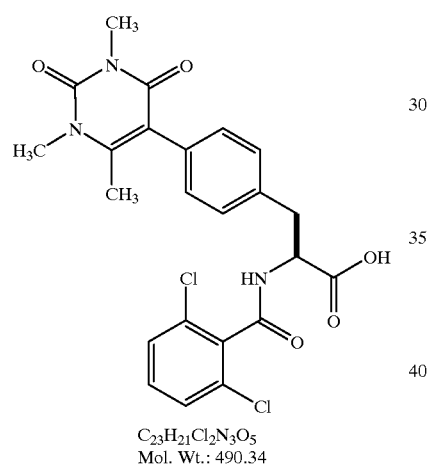

C$_{23}$H$_{21}$Cl$_2$N$_3$O$_5$
Mol. Wt.: 490.34

To a suspension of N-[(2,6-dichlorophenyl)carbonyl]-4-(1,3,6-trimethyl-2,4-dioxo-5-pyrimidinyl)-L-phenylalanine methyl ester (2.2 mmol, 1.11 g) in ethanol (12 mL) was added aqueous 1.0 N sodium hydroxide (8.8 mL) at room temperature. The mixture was heated to 45–50° C. and the resulting clear solution was stirred for approximately 2 h. The ethanol was removed under reduced pressure and the residue was diluted with water (50 mL) and NaOH (5 mL, 1.0N) to dissolve the sodium salt. The aqueous solution was washed with diethyl ether (50 mL) to remove any neutral impurities. The aqueous layer was acidified with 1.0 N HCl and the product was extracted into ethyl acetate (2×75 mL). The combined organic extracts were washed with brine solution (100 mL) and were dried over anhydrous magnesium sulfate. Filtration of the drying agent and concentration of the filtrate afforded 970 mg (90% yield) of N-[(2,6-dichlorophenyl)carbonyl]-4-(1,3,6-trimethyl-2,4-dioxo-5-pyrimidinyl)-L-phenylalanine as a white solid: mp 225–227° C. FAB-HRMS m/e calcd for $C_{23}H_{21}Cl_2N_3O_5$ (M+H) 490.0937, found 490.0940.

Example 7

Preparation of N-[[1-(2-methoxyethyl)cyclopentyl]carbonyl]-4-(1,3,6-trimethyl-2,4-dioxo-5-pyrimidinyl)-L-phenylalanine a) Preparation of N-[[1-(2-methoxyethyl)cyclopentyl]carbonyl]-$^4$-(1,3,6-trimethyl-2,4-dioxo-5-pyrimidinyl)-L-phenylalanine methyl ester

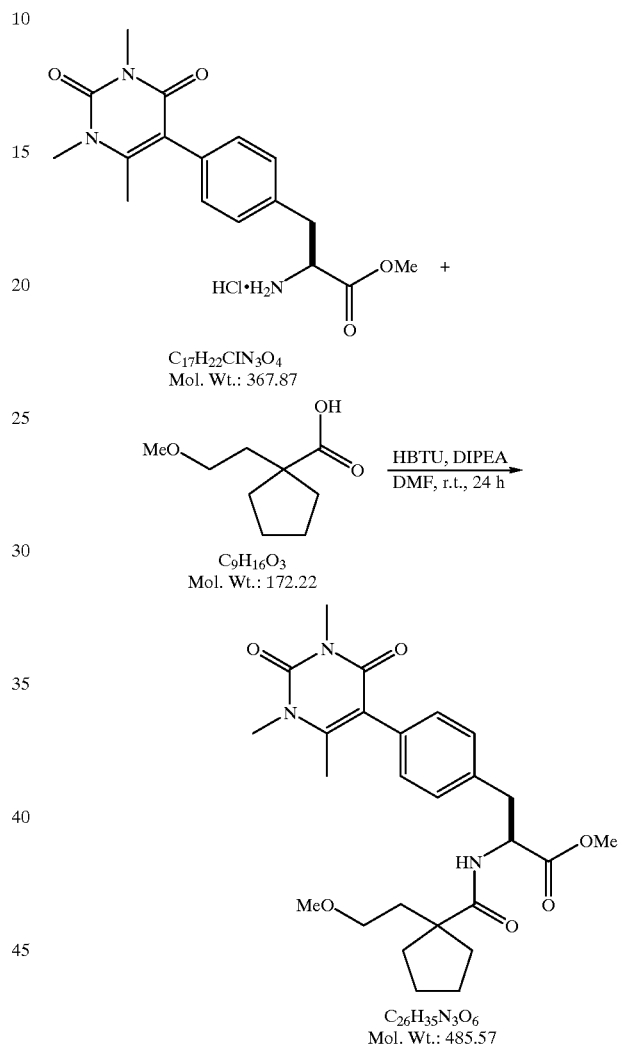

To a suspension of 4-(1,3,6-trimethyl-2,4-dioxo-5-pyrimidinyl)-L-phenylalanine methyl ester hydrochloride salt (0.4 mmol, 173 mg), HBTU (0.5 mmol, 189 mg) and 1-(2-methoxyethyl)cyclopentane carboxylic acid (0.5 mmol, 86 mg) in DMF (2 mL) was added diisopropylethylamine (1.2 mmol, 0.29 mL) at room temperature. After 5 min, everything went into solution and the clear yellow solution was stirred for 24 h at room temperature. The resulting dark-brown solution was diluted with ethyl acetate (30 mL). The ethyl acetate layer was washed successively with 1N hydrochloric acid (2×30 mL), saturated sodium bicarbonate solution (30 mL), and brine solution (30 mL) and was dried over anhydrous magnesium sulfate. Filtration of the drying agent and concentration of the solvent gave the crude product which was purified by silica gel column chromatography using a Biotage (40m) column to afford 139 mg (72% yield) of N-[[1-(2-methoxyethyl)cyclopentyl]

carbonyl]-4-(1,3,6-trimethyl-2,4-dioxo-5-pyrimidinyl)-L-phenylalanine methyl ester as an amorphous white solid. FAB-HRMS m/e calcd for $C_{26}H_{35}N_3O_6$ (M+H) 486.2604, found 486.2602.

b) Preparation of N-[[1-(2-methoxyethyl)cyclopentyl]carbonyl]-4-(1,3,6-trimethyl-2,4-dioxo-5-pyrimidinyl)-L-phenylalanine

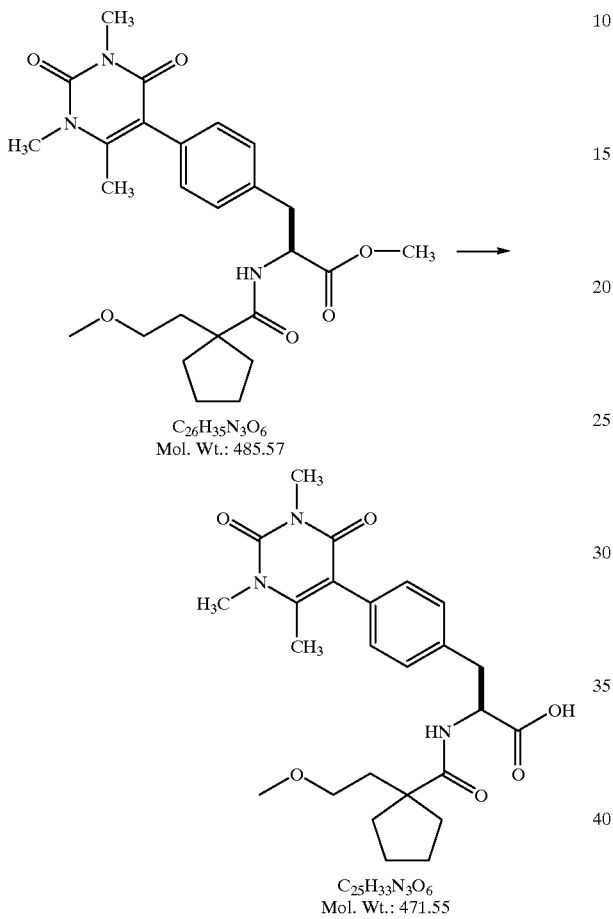

To a suspension of N-[[1-(2-methoxyethyl)cyclopentyl]carbonyl]-4-(1,3,6-trimethyl-2,4-dioxo-5-pyrimidinyl)-L-phenylalanine methyl ester (0.273 mmol, 133 mg) in ethanol (3 mL) was added aqueous 1.0 N sodium hydroxide (1.5 mL) at room temperature. The mixture was heated to 40–45° C. and the resulting clear solution was stirred for 15 h. The ethanol was removed under reduced pressure and the residue was diluted with water (25 mL) and NaOH (3 mL, 1.0N) to dissolve the sodium salt. The aqueous solution was washed with diethyl ether (50 mL) to remove any neutral impurities. The aqueous layer was acidified with 1.0 N HCl and the product was extracted into ethyl acetate (2×25 mL). The combined organic extracts were washed with brine solution (50 mL) and were dried over anhydrous magnesium sulfate. Filtration of the drying agent and concentration of the filtrate afforded 121 mg (94% yield) of N-[[1-(2-methoxyethyl)cyclopentyl]carbonyl]-4-(1,3,6-trimethyl-2,4-dioxo-5-pyrimidinyl)-L-phenylalanine as an amorphous white solid. FAB-HRMS m/e calcd for $C_{25}H_{33}N_3O_6$ (M+H) 472.2448, found 472.2467.

Example 8

Preparation of N-[(2-bromo-6-methylphenyl)carbonyl]-4-(1,3,6-trimethyl-2,4-dioxo-5-pyrimidinyl)-L-phenylalanine

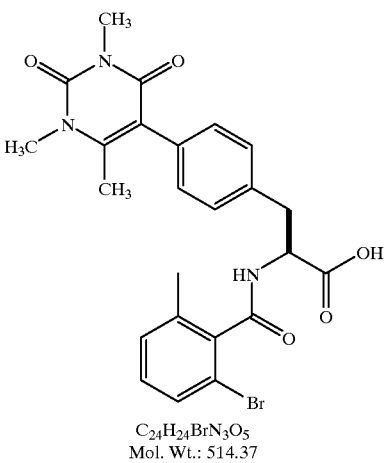

N-[(2-bromo-6-methylphenyl)carbonyl]-4-(1,3,6-trimethyl-2,4-dioxo-5-pyrimidinyl)-L-phenylalanine was prepared from 4-(1,3,6-trimethyl-2,4-dioxo-5-pyrimidinyl)-L-phenylalanine methyl ester and 2-bromo-6-methylbenzoic acid using the general procedures described in example 7 and was obtained as a white solid: mp 240–242° C. FAB-HRMS m/e calcd for $C_{24}H_{24}BrN_3O_5$ (M+H) 514.0978, found 514.0965.

Example 9

Preparation of N-[(2-chloro-6-methylphenyl)carbonyl]-4-(1,3,6-trimethyl-2,4-dioxo-5-pyrimidinyl)-L-phenylalanine

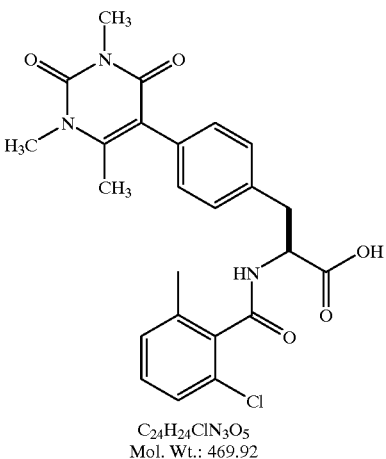

N-[(2-chloro-6-methylphenyl)carbonyl]-4-(1,3,6-trimethyl-2,4-dioxo-5-pyrimidinyl)-L-phenylalanine was prepared from 4-(1,3,6-trimethyl-2,4-dioxo-5-pyrimidinyl)-L-phenylalanine methyl ester and 2-chloro-6-methylbenzoic acid using the general procedures described in example 7 and was obtained as a white solid: mp 238–240° C. FAB- HRMS m/e calcd for $C_{24}H_{24}ClN_3O_5$ (M+H) 470.1483, found 470.1489.

Example 10

Preparation of N-[(2-ethyl-6-methylphenyl) carbonyl]-4-(1,3,6-trimethyl-2,4-dioxo-5-pyrimidinyl)-L-phenylalanine

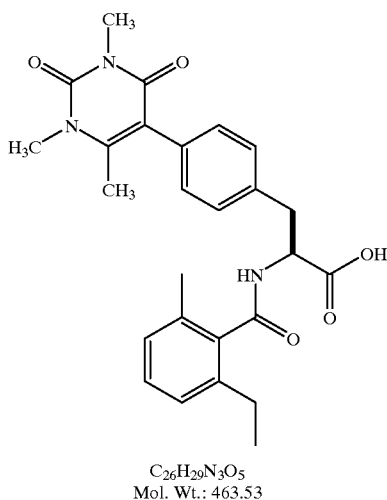

$C_{26}H_{29}N_3O_5$
Mol. Wt.: 463.53

N-[(2-ethyl-6-methylphenyl)carbonyl]-4-(1,3,6-trimethyl-2,4-dioxo-5-pyrimidinyl)-L-phenylalanine was prepared from 4-(1,3,6-trimethyl-2,4-dioxo-5-pyrimidinyl)-L-phenylalanine methyl ester and 2-ethyl-6-methylbenzoic acid using the general procedures described in example 7 and was obtained as a white solid: mp 127–133° C. ES-HRMS m/e calcd for $C_{26}H_{29}N_3O_5$ (M+Na) 494.1498, found 494.1501.

Example 11

Preparation of N-[[2-(2-methylethyl)-6-methylphenyl]carbonyl]-4-(1,3,6-trimethyl-2,4-dioxo-5-pyrimidinyl)-L-phenylalanine

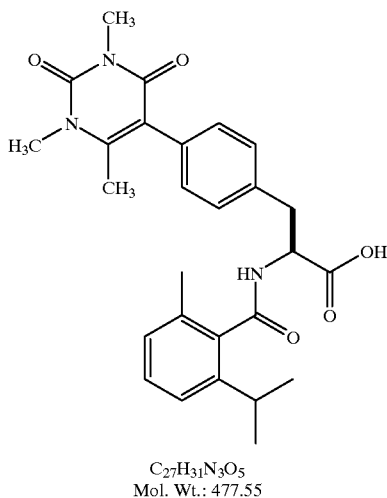

$C_{27}H_{31}N_3O_5$
Mol. Wt.: 477.55

N-[[2-(2-methylethyl)-6-methylphenyl]carbonyl]-4-(1,3,6-trimethyl-2,4-dioxo-5-pyrimidinyl)-L-phenylalanine was prepared from 4-(1,3,6-trimethyl-2,4-dioxo-5-pyrimidinyl)-L-phenylalanine methyl ester and 2-(2-methylethyl)-6-methylbenzoic acid using the general procedures described in example 7 and was obtained as an amorphous white solid. ES-HRMS m/e calcd for $C_{27}H31N_3O_5$ (M+Na) 500.2156, found 500.2160.

Example 12

Preparation of N-[(2,6-difluorophenyl)carbonyl]-4-(1,3,6-trimethyl-2,4-dioxo-5-pyrimidinyl)-L-phenylalanine

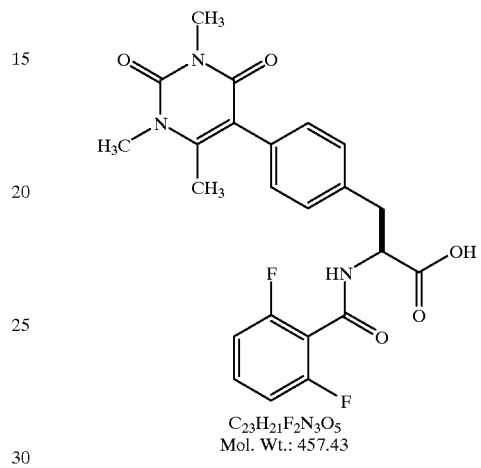

$C_{23}H_{21}F_2N_3O_5$
Mol. Wt.: 457.43

N-[(2,6-difluorophenyl)carbonyl]-4-(1,3,6-trimethyl-2,4-dioxo-5-pyrimidinyl)-L-phenylalanine was prepared from 4-(1,3,6-trimethyl-2,4-dioxo-5-pyrimidinyl)-L-phenylalanine methyl ester and 2,6-difluorobenzoic acid using the general procedures described in example 7 and was obtained as an amorphous white solid. ES-HRMS m/e calcd for $C_{23}H_{21}F_2N_3O_5$ (M+Na) 480.1483, found 480.1489.

Example 13

Preparation of N-[[2-fluoro-6-(trifluoromethyl) phenyl]carbonyl]-4-(1,3,6-trimethyl-2,4-dioxo-5-pyrimidinyl)-L-phenylalanne

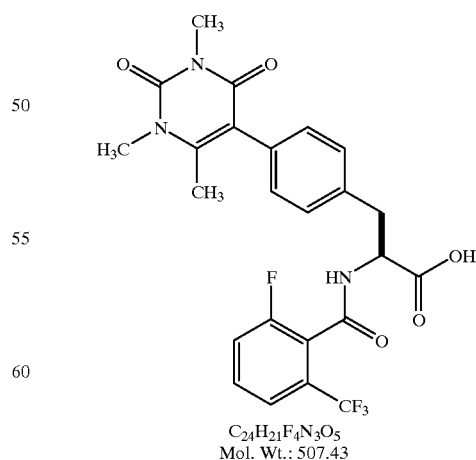

$C_{24}H_{21}F_4N_3O_5$
Mol. Wt.: 507.43

N-[(2-fluoro-6-(trifluoromethyl)phenyl)carbonyl]-4-(1,3,6-trimethyl-2,4-dioxo-5-pyrimidinyl)-L-phenylalanine was prepared from 4-(1,3,6-trimethyl-2,4-dioxo-5-pyrimidinyl)-L-phenylalanine methyl ester and 2-fluoro-6-(trifluoromethyl)benzoic acid using the general procedures described in example 7 and was obtained as a white solid: mp 218–220° C. ES-HRMS m/e calcd for $C_{25}H_{23}F_4N_3O_5$ (M+Na) 530.1310, found 530.1317.

Example 14

Preparation of N-[[2,6-di-(2-methylethyl)phenyl]carbonyl]-4-(1,3,6-trimethyl-2,4-dioxo-5-pyrimidinyl)-L-phenylalanine

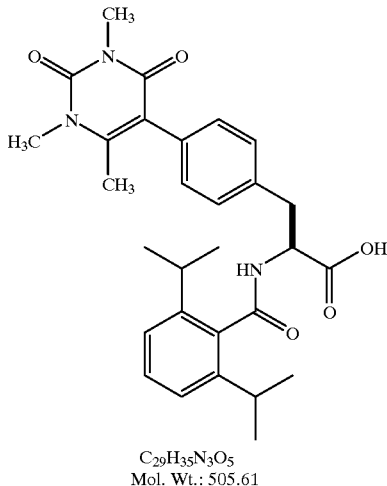

$C_{29}H_{35}N_3O_5$
Mol. Wt.: 505.61

N-[[2,6-di-(2-methylethyl)phenyl]carbonyl]-4-(1,3,6-trimethyl-2,4-dioxo-5-pyrinidinyl)-L-phenylalanine was prepared from 4-(1,3,6-trimethyl-2,4-dioxo-5-pyrimidinyl)-L-phenylalanine methyl ester and 2,6-di-(2-methylethyl) benzoic acid using the general procedures described in example 7 and was obtained as an amorphous white solid. ES-HRMS m/e calcd for $C_{29}H_{35}N_3O_5$ (M+Na) 530.1310, found 530.1317.

Example 15

Preparation of N-[(2-chloro-6-ethylphenyl)carbonyl]-4-(1,3,6-trimethyl-2,4-dioxo-5-pyrimidinyl)-L-phenylalanine a) Preparation of N-(2-chloro-6-fluorobenzylidine)butyl amine (Ro 50-5007/000, 30935-229)

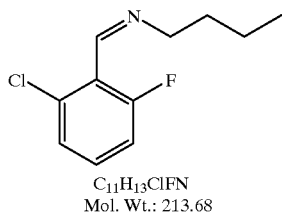

$C_{11}H_{13}ClFN$
Mol. Wt.: 213.68

To a suspension of 2-chloro-6-fluorobenzaldehyde (416 mmol, 66 g) in heptanes (200 mL) was added n-butylamine (460 mmol, 45.5 mL) at room temperature. After addition, an exothermic reaction as the solids dissolved completely. The solution was stirred for 3 h at room temperature, was transferred into a separatory funnel, was washed with brine solution (200 mL) and was dried over anhydrous magnesium sulfate. Filtration of the drying agent and concentration gave a yellow oil which was purified by distillation under high vacuum (bp 95–98° C./4.5 mm Hg) to obtain 86.31 g (97% yield) of N-(2-chloro-6-fluorobenzylidine)butyl amine as an yellow oil. EI-HRMS m/e calcd for $C_{11}H_{13}ClFN$ (M$^+$) 213.0720, found 213.0714.

b) Preparation of 2-chloro-6-ethylbenzaldehyde

$C_9H_9ClO$
Mol. Wt.: 168.62

To a solution of N-(2-chloro-6-fluorobenzylidine)butyl amine (15 mmol, 3.21 g) in THF (20 mL) was added dropwise a solution of ethylmagnesium bromide (30 mmol, 30 mL, 1 M) in THF by maintaining the temperature at 5–15° C. After addition, the reaction mixture was allowed to warm to 20° C. and was stirred for 5 h. Then, it was cooled to 0° C. (ice bath) and 20% HCl in water (50 mL) was added dropwise while maintaining the temperature below 15° C. with ice bath cooling. After addition, the mixture was allowed to warm to room temperature and was stirred for 15 h. Then, it was diluted with water (75 mL) and extracted with ethyl acetate (2×50 mL). The combined extracts were washed with brine solution (100 mL) and dried over anhydrous magnesium sulfate. Filtration of the drying agent and concentration gave 2.27 g (90% yield) of 2-chloro-6-ethylbenzaldehyde as an yellow oil. EI-HRMS m/e calcd for $C_9H_9ClO$ (M$^+$) 167.0264, found 167.0263.

c) Preparation of 2-chloro-6-ethylbenzoic acid

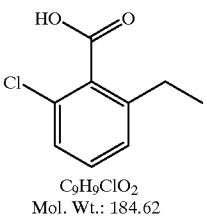

$C_9H_9ClO_2$
Mol. Wt.: 184.62

To a room temperature suspension of 2-chloro-6-ethylbenzaldehyde (13.5 mmol, 2.27 g) in acetonitrile (25 mL) was added a solution of monobasic sodium phosphate (3.4 mmol, 0.465 g) in water (7.5 mL) followed by hydrogen peroxide (1.8 mL, 30%). Then, a solution of sodium chlorite (23.7 mmol, 2.15 g) in water (20 mL) was added dropwise at 0° C. while maintaining the temperature below 3° C. After addition, the yellow suspension was stirred for 15 h at 0° C. to room temperature. At this time TLC analysis of the mixture indicated the absence of starting material. Then, a solution of sodium bisulfite (20.5 mmol, 2.8 g) in water (10 mL) was added dropwise at 0° C. until the yellow color disappeared (KI-paper positive). Cooling is essential to control the exothermic reaction. After 1 h, the solvent was removed under vacuum. The neutral impurities were extracted with diethyl ether (200 mL). Then, the basic aqueous solution was neutralized with 10% HCl to pH ~1. The precipitated white solid was collected by filtration and dried at in air to afford 2.415 g (97% yield) of 2-chloro-6-ethylbenzoic acid as an amorphous white solid. EI-HRMS m/e calcd for $C_9H_9ClO_2$ (M$^+$) 184.0291, found 184.0295.

d) Preparation of N-[(2-chloro-6-ethylphenyl)carbonyl]-4-(1,3,6-trimethyl-2,4-dioxo-5-pyrimidinyl)-L-phenylalanine methyl ester

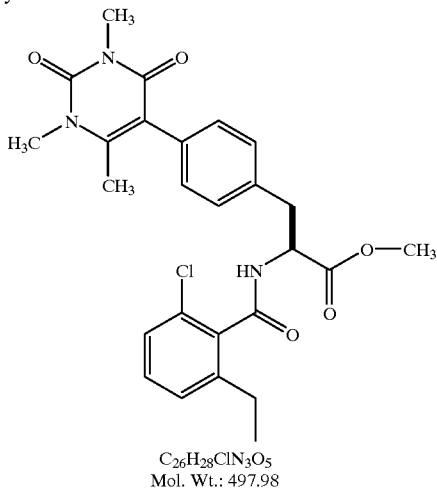

C$_{26}$H$_{28}$ClN$_3$O$_5$
Mol. Wt.: 497.98

To a suspension of 4-(1,3,6-trimethyl-2,4-dioxo-5-pyrimidinyl)-L-phenylalanine methyl ester hydrochloride salt (0.5 mmol, 184 mg), HBTU (0.7 mmol, 265 mg) and 2-chloro-6-ethylbenzoic acid (0.7 mmol, 129 mg) in DMF (2 mL) was added diisopropylethylamine (1.25 mmol, 0.22 mL) at room temperature. After 5 min, everything went into solution and the clear yellow solution was stirred for 15 h at room temperature. The resulting dark-brown solution was diluted with ethyl acetate (30 mL). The ethyl acetate layer was washed successively with 1N hydrochloric acid (2×30 mL), saturated sodium bicarbonate solution (30 mL), and brine solution (30 mL) and was dried over anhydrous magnesium sulfate. Filtration of the drying agent and concentration of the solvent gave the crude product which was purified by silica gel column chromatography using a Biotage (40m) column to afford 175 mg (70% yield) of N-[(2-chloro-6-ethylphenyl)carbonyl]-4-(1,3,6-trimethyl-2,4-dioxo-5-pyrimidinyl)-L-phenylalanine methyl ester as an amorphous white solid. ES-HRMS m/e calcd for C$_{26}$H$_{28}$ClN$_3$O$_5$ (M+Na) 520.1611, found 520.1613.

e) Preparation of N-[(2-chloro-6-ethylphenyl)carbonyl]-4-(1,3,6-trimethyl-2,4-dioxo-5-pyrimidinyl)-L-phenylalanine

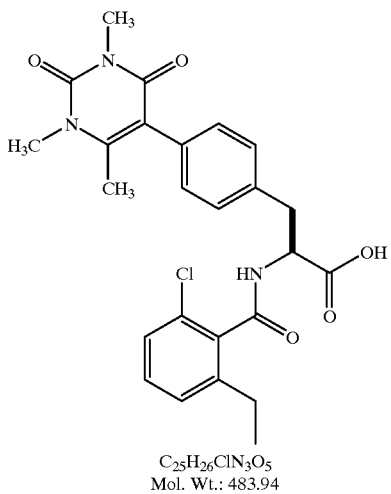

C$_{25}$H$_{26}$ClN$_3$O$_5$
Mol. Wt.: 483.94

To a suspension of N-[(2-chloro-6-ethylphenyl)carbonyl]-4-(1,3,6-trimethyl-2,4-dioxo-5-pyrimidinyl)-L-phenylalanine methyl ester (0.33 mmol, 164 mg) in ethanol (2 mL) was added aqueous 1.0 N sodium hydroxide (0.7 mL) at room temperature. The mixture was stirred for 3 h at room temperature. The ethanol was removed under reduced pressure and the residue was diluted with water (30 mL). The aqueous solution was washed with diethyl ether (30 mL) to remove any neutral impurities. The aqueous layer was acidified with 1.0 N HCl and the product was extracted into ethyl acetate (2×35 mL). The combined organic extracts were washed with brine solution (50 mL) and were dried over anhydrous magnesium sulfate. Filtration of the drying agent and concentration of the filtrate afforded 138 mg (87% yield) of N-[(2-chloro-6-ethylphenyl)carbonyl]-4-(1,3,6-trimethyl-2,4-dioxo-5-pyrimidinyl)-L-phenylalanine as a white solid: mp 187–190° C. ES-HRMS m/e calcd for C$_{25}$H$_{26}$ClN$_3$O$_5$ (M+Na) 506.1459, found 506.1455.

Example 16

Preparation of N-[(2-chloro-6-propylphenyl)carbonyl]-4-(1,3,6-trimethyl-2,4-dioxo-5-pyrimidinyl)-L-phenylalanine a. Preparation of 2-chloro-6-propylbenzoic acid.

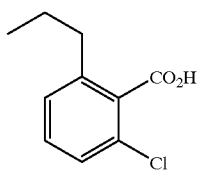

2-chloro-6-propylbenzoic acid was prepared from 2-fluoro-6-chlorobenzilidine)butylamine and propyl magnesium bromide using the general procedure described in example 15.

b. Preparation of N-[(2-chloro-6-propylphenyl)carbonyl]-4-(1,3,6-trimethyl-2,4-dioxo-5-pyrimidinyl)-L-phenylalanine

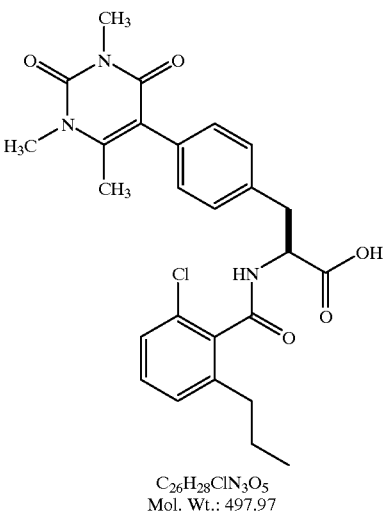

C$_{26}$H$_{28}$ClN$_3$O$_5$
Mol. Wt.: 497.97

N-[(2-chloro-6-propylphenyl)carbonyl]-4-(1,3,6-trimethyl-2,4-dioxo-5-pyrimidinyl)-L-phenylalanine was prepared from 4-(1,3,6-trimethyl-2,4-dioxo-5-pyrimidinyl)-L-phenylalanine methyl ester and 2-chloro-6-propylbenzoic acid using the general procedures described in example 15 and was obtained as a white solid: mp 225–227° C. ES-HRMS m/e calcd for $C_{26}H_{28}ClN_3O_5$ (M+Na) 520.1611, found 520.1615.

Example 17

Preparation of N-[[2-chloro-6-(2-methylethyl)phenyl]carbonyl]-4-(1,3,6-trimethyl-2,4-dioxo-5-pyrimidinyl)-L-phenylalanine a. Preparation of 2-chloro-6-(2-methylethyl)benzoic acid.

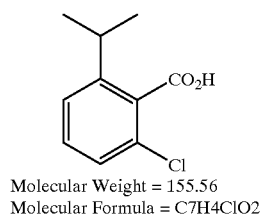

Molecular Weight = 155.56
Molecular Formula = C7H4ClO2

2-chloro-6-(2-methylethyl)benzoic acid was prepared from 2-fluoro-6-chlorobenzilidine)butylamine and isopropyl magnesium bromide using the general procedure described in example 15.

b. Preparation of N-[[2-chloro-6-(2-methylethyl)phenyl]carbonyl]-4-(1,3,6-trimethyl-2,4-dioxo-5-pyrimidinyl)-L-phenylalanine

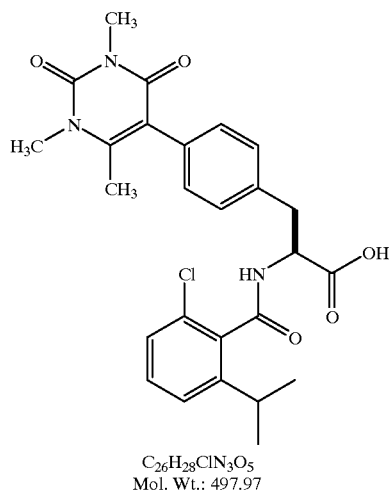

$C_{26}H_{28}ClN_3O_5$
Mol. Wt.: 497.97

N-[[2-chloro-6-(2-methylethyl)phenyl]carbonyl]-4-(1,3,6-rimethyl-2,4-dioxo-5-pyrimidinyl)-L-phenylalanine was prepared from 4-(1,3,6-trimethyl-2,4-dioxo-5-pyrimidinyl)-L-phenylalanine methyl ester and 2-chloro-6-(2-methylethyl)benzoic acid using the general procedures described in example 15 and was obtained as a white solid: mp 205–209° C. ES-HRMS m/e calcd for $C_{26}H_{28}ClN_3O_5$ (M+Na) 520.1611, found 520.1617.

Example 18

N-[(2,6-dichlorophenyl)carbonyl]-4-(1,3-diethyl-6-methyl-2,4-dioxo-5-pyrimidinyl)-L-phenylalanine a) Preparation of 5-iodo-1,3-diethyl-6-methyl uracil

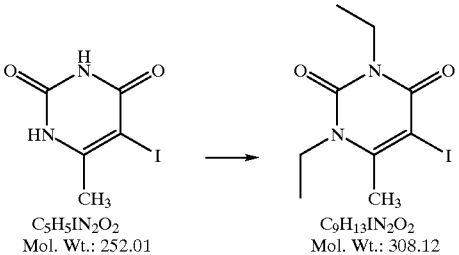

C5H5IN2O2
Mol. Wt.: 252.01

C9H13IN2O2
Mol. Wt.: 308.12

To a suspension of 5-iodo-6-methyl uracil (20.97 mmol, 5.45 g) and powdered potassium carbonate (60 mmol, 8.29 g) in DMF (188 mL) was added ethyl iodide (83.88 mmol, 6.7 mL). The reaction mixture was stirred for 15 h at room temperature and was poured into water (150 mL) and ethyl acetate (150 mL). The layers were separated and the aqueous layer was extracted with ethyl acetate (2×100 mL). The combined extracts were washed with brine solution (150 mL) and were dried over anhydrous magnesium sulfate. Filtration of the drying agent and concentration gave a crude solid which was triturated with dichloromethane/diethyl ether/hexanes (1:1:1) to afford 3.89 g (60% yield) of 5-iodo-1,3-diethyl-6-methyl uracil as a white crystalline solid: mp 159–161.5° C. EI-HRMS m/e calcd for $C_9H_{13}IN_2O_2$ (M$^+$) 308.0022, found 308.0018.

b) Preparation of N-[(1,1-dimethylethoxy)carbonyl]-4-(1,3-diethyl-6-methyl-2,4-dioxo-5-pyrimidinyl)-L-phenylalanine methyl ester

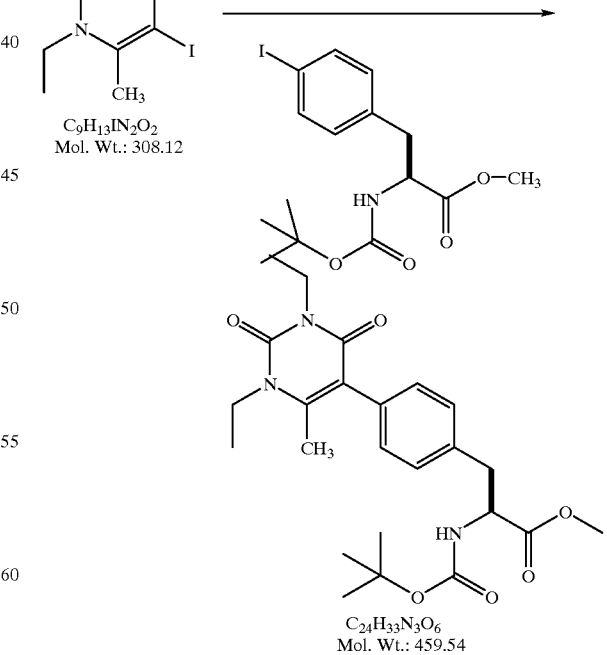

C9H13IN2O2
Mol. Wt.: 308.12

C24H33N3O6
Mol. Wt.: 459.54

To a suspension of zinc dust (33 mmol, 1.96 g) in THF (3 mL) was added 1,2-dibromoethane (3 mmol, 0.261 mL) at room temperature. This suspension was heated to 60–65° C. with a heat gun until evolution of ethylene gas ceased. The suspension was cooled to room temperature, trimethylchlorosilane (1.5 mmol, 0.19 mL) was added and the mixture was stirred for 15 min. A suspension of 5-iodo-1,3-diethyl-6-methyl uracil (11 mmol, 3.39 g) in DMA (6 mL) was warmed to obtain a clear solution and was added in one portion to the reaction mixture. After addition, the mixture was heated to 70° C. The internal temperature of the reaction mixture rose to 75° C. due to the exothermic reaction. The reaction mixture was maintained at 70° C. for 15 h at which time the TLC analysis of an aliquot of the reaction mixture, which was quenched with saturated ammonium chloride solution, indicated the absence of starting material. The reaction mixture was diluted with THF (6 mL) and the reaction mixture was cooled to room temperature. The excess zinc dust was allowed to settle.

The solution containing the above prepared zinc compound (11 mmol) was added to a solution of $Pd(dba)_2$ (0.14 mmol, 80 mg), trifurylphosphine (TFP) (0.52 mmol, 134 mg) and N-[(1,1-dimethylethoxy)carbonyl]-4-iodo-L-phenylalanine methyl ester (9 mmol, 3.65 g) in THF (6 mL) at room temperature and the light yellow mixture was stirred for 72 h at 50–55° C. The reaction mixture was poured into a saturated ammonium chloride solution (100 mL) and was extracted with ethyl acetate (3×75 mL). The combined extracts were washed with brine solution (150 mL) and dried over anhydrous magnesium sulfate. Filtration of the drying agent and concentration gave the crude product which was purified by silica gel column chromatography using a Biotage column (40m) to obtain 1.78 g (43% yield) of N-[(1,1-dimethylethoxy)carbonyl]-4-(1,3-diethyl-6-methyl-2,4-dioxo-5-pyrimidinyl)-L-phenylalanine methyl ester as an amorphous white solid. ES-HRMS m/e calcd for $C_{24}H_{33}N_3O_6$ (M+Na) 482.2262, found 482.2262.

c) Preparation of 4-(1,3-diethyl-6-methyl-2,4-dioxo-5-pyrimidinyl)-L-phenylalanine methyl ester hydrochloride salt

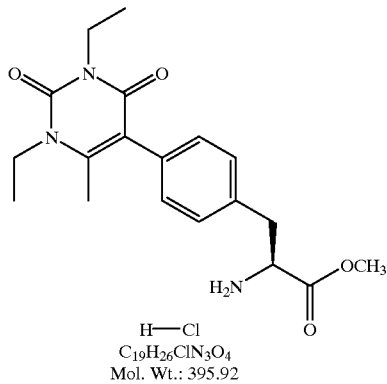

H—Cl
$C_{19}H_{26}ClN_3O_4$
Mol. Wt.: 395.92

To a solution of N-[(1,1-dimethylethoxy)carbonyl]-4-(1,3-diethyl-6-methyl-2,4-dioxo-5-pyrirnidinyl)-L-phenylalanine methyl ester (3.87 mmol, 1.78 g) in dioxane (10 mL) was added 4N hydrochloric acid in dioxane (20 mmol, 5 mL) at room temperature and the solution was stirred for 1 h. The solution was concentrated and was diluted with diethyl ether to form a white solid. The mother liquor was decanted and the residue was dried on a rotary evaporator and then under high vacuum to afford 0.72 g (47% yield) of 4-(1,3-diethyl-6-methyl-2,4-dioxo-5-pyrimidinyl)-L-phenylalanine methyl ester hydrochloride salt as an amorphous solid. ES-HRMS m/e calcd for $C_{19}H_{25}N_3O_4$ (M+Na) 382.1737, found 382.1736.

d) Preparation of N-[(2,6-dichlorophenyl)carbonyl]-4-(1,3-diethyl-6-methyl-2,4-dioxo-5-pyrimidinyl)-L-phenylalanine methyl ester

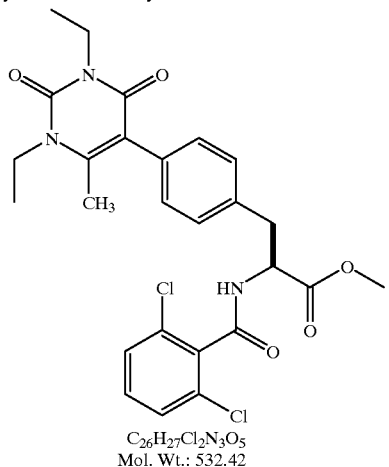

$C_{26}H_{27}Cl_2N_3O_5$
Mol. Wt.: 532.42

To a suspension of 4-(1,3-diethyl-6-methyl-2,4-dioxo-5-pyrimidinyl)-L-phenylalanine methyl ester hydrochloride salt (0.76 mmol, 0.3 g) and 2,6-dichlorobenzoyl chloride (0.84 mmol, 0.175 g) in dichloromethane (2 mL) was added diisopropylethylamine (3.03 mmol, 0.53 mL) at room temperature. After 5 min, everything went into solution and the clear yellow solution was stirred for 15 h at room temperature. The resulting brown solution was diluted with dichloromethane (25 mL). The dichloromethane layer was washed successively with 1N hydrochloric acid (2×25 mL), saturated sodium bicarbonate solution (25 mL), and brine solution (25 mL) and was dried over anhydrous magnesium sulfate. Filtration of the drying agent and concentration of the solvent gave the crude product which was purified by silica gel chromatography using a Biotage (40s) column to afford 0.40 g (99% yield) of N-[(2,6-dichlorophenyl)carbonyl]-4-(1,3-diethyl-6-methyl-2,4-dioxo-5-pyrimidinyl)-L-phenylalanine methyl ester as an amorphous white solid. ES-HRMS m/e calcd for $C_{26}H_{27}Cl_2N_3O_5$ (M+Na) 554.1221, found 554.1229.

e) Preparation of N-[(2,6-dichlorophenyl)carbonyl]-4-(1,3-diethyl-6-methyl-2,4-dioxo-5-pyrimidinyl)-L-phenylalanine

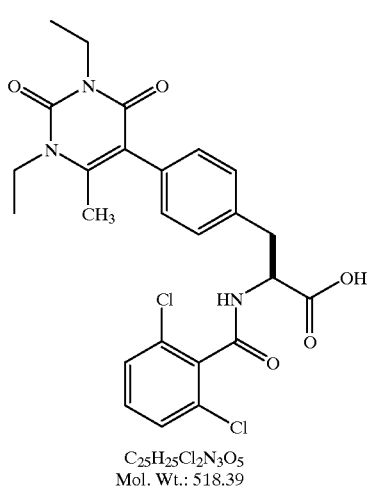

$C_{25}H_{25}Cl_2N_3O_5$
Mol. Wt.: 518.39

To a suspension of N-[(2,6-dichlorophenyl)carbonyl]-4-(1,3-diethyl-6-methyl-2,4-dioxo-5-pyrimidinyl)-L-phenylalanine methyl ester (0.77 mmol, 0.41 g) in ethanol (2 mL) was added aqueous 1.0 N sodium hydroxide (1.5 mL) at room temperature. The mixture was heated to 50° C. and the resulting clear solution was stirred for 2 h. Then, the ethanol was removed under reduced pressure and the residue was diluted with water (25 mL) and NaOH (2 mL, 1.0N) to dissolve the sodium salt. The aqueous solution was washed with diethyl ether (30 mL) to remove any neutral impurities. The aqueous layer was acidified with 1.0 N HCl and the product was extracted into ethyl acetate (2×25 mL). The combined organic extracts were washed with brine solution (50 mL) and were dried over anhydrous magnesium sulfate. Filtration of the drying agent and concentration of the filtrate afforded 320 mg (80% yield) of N-[(2,6-dichlorophenyl)carbonyl]-4-(1,3-diethyl-6-methyl-2,4-dioxo-5-pyrimidinyl)-L-phenylalanine as an amorphous white solid. ES-HRMS m/e calcd for $C_{25}H_{25}Cl_2N_3O_5$ (M+Na) 541.3921, found 541.3925.

Example 19

Preparation of N-[(2-chloro-6-methylphenyl)carbonyl]-4-(1,3-diethyl-6-methyl-2,4-dioxo-5-pyrimidinyl)-L-phenylalanine a) Preparation of N-[(2-chloro-6-methylphenyl)carbonyl]-4-(1,3-diethyl-6-methyl-2,4-dioxo-5-pyrimidinyl)-L-phenylalanine methyl ester

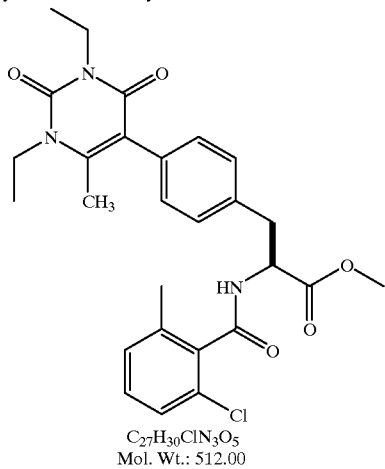

$C_{27}H_{30}ClN_3O_5$
Mol. Wt.: 512.00

To a suspension of 4-(1,3-diethyl-6-methyl-2,4-dioxo-5-pyrimidinyl)-L-phenylalanine methyl ester hydrochloride salt (0.758 mmol, 300 mg), HBTU (0.84 mmol, 318 mg) and 2-chloro-6-methylbenzoic acid (0.84 mmol, 142 mg) in DMF (2 mL) was added diisopropylethylamine (1.9 mmol, 0.33 mL) at room temperature. After 5 min, everything went into solution and the clear yellow solution was stirred for 48 h at room temperature. The resulting dark-brown solution was diluted with ethyl acetate (30 mL). The ethyl acetate layer was washed successively with 1N hydrochloric acid (2×30 mL), saturated sodium bicarbonate solution (30 mL), and brine solution (30 mL) and was dried over anhydrous magnesium sulfate. Filtration of the drying agent and concentration gave the crude product which was purified by silica gel chromatography using a Biotage (40m) column to afford 380 mg (98% yield) of N-[(2-chloro-6-methylphenyl)carbonyl]-4-(1,3-diethyl-6-methyl-2,4-dioxo-5-pyrimidinyl)-L-phenylalanine methyl ester as an amorphous white solid. ES-HRMS m/e calcd for $C_{27}H_{30}ClN_3O_5$ (M+Na) 535.1026, found 535.1024.

b) Preparation of N-[(2-chloro-6-methylphenyl)carbonyl]-4-(1,3-diethyl-6-methyl-2,4-dioxo-5-pyrimidinyl)-L-phenylalanine

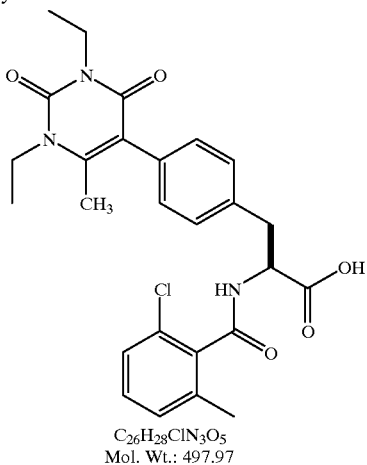

$C_{26}H_{28}ClN_3O_5$
Mol. Wt.: 497.97

To a suspension of N-[(2-chloro-6-methylphenyl)carbonyl]-4-(1,3-diethyl-6-methyl-2,4-dioxo-5-pyrimidinyl)-L-phenylalanine methyl ester (0.82 mmol, 420 mg) in ethanol (2 mL) was added aqueous 1.0 N sodium hydroxide (1.6 mL) at room temperature. The mixture was heated to 50° C. and the resulting clear solution was stirred for 2 h. The ethanol was removed under reduced pressure and the residue was diluted with water (25 mL) and NaOH (3 mL, 1.0N) to dissolve the sodium salt. The aqueous solution was washed with diethyl ether (30 mL) to remove any neutral impurities. The aqueous layer was acidified with 1.0 N HCl and the product was extracted into ethyl acetate (2×25mL). The combined organic extracts were washed with brine solution (50 mL) and were dried over anhydrous magnesium sulfate. Filtration of the drying agent and concentration of the filtrate afforded 277 mg (68% yield) of N-[(2-chloro-6-methylphenyl)carbonyl]-4-(1,3-diethyl-6-methyl-2,4-dioxo-5-pyrimidinyl)-L-phenylalanine as an amorphous white solid. ES-HRMS m/e calcd for $C_{26}H_{28}ClN_3O_5$ (M+Na) 520.1611, found 520.1616.

Example 20

Preparation of 4-(1,3-diethyl-6-methyl-2,4-dioxo-5-pyrimidinyl)-N-[[1-(2-methoxyethyl)cyclopentyl]carbonyl]-L-phenylalanine

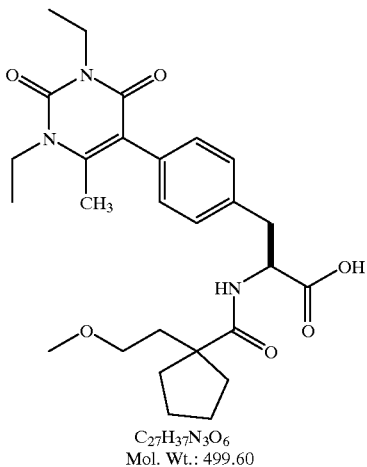

$C_{27}H_{37}N_3O_6$
Mol. Wt.: 499.60

4-(1,3-diethyl-6-methyl-2,4-dioxo-5-pyrimidinyl)-N-[[1-(2-methoxyethyl)cyclopentyl]carbonyl]-L-phenylalanine was prepared from 4-(1, 3-diethyl-6-methyl-2,4-dioxo-5-pyrimidinyl)-L-phenylalanine methyl ester and 1-(2-methoxyethyl)cyclopentane carboxylic acid using the general procedures described in example 19 and was obtained as an amorphous white solid. ES-HRMS m/e calcd for $C_{27}H_{37}N_3O_6$ (M+Na) 522.2575, found 522.2581.

Example 21

N-[1-(2,6-dichlorophenyl)carbonyl]-4-(1,3-dimethyl-2,4-dioxo-6-(trifluoromethyl)-5-pyrimidinyl)-L-phenylalanine a) Preparation of 3-methyl-6-(trifluoromethyl) uracil

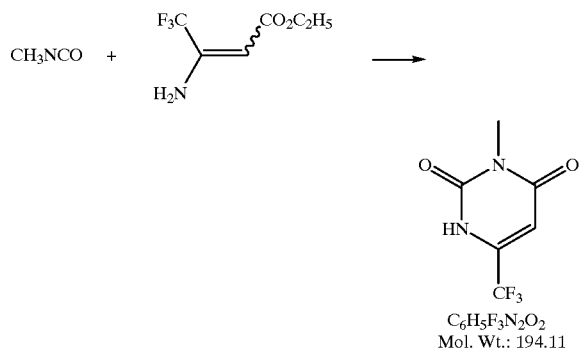

$C_6H_5F_3N_2O_2$
Mol. Wt.: 194.11

To a pre-mixed solution of sodium methoxide (55 mmol, 2.97 g) and ethyl 3-amino-4,4,4-trifluorocrotonate (55 mmol, 10.0 g) in DMSO (19 mL, dried over molecular sieves) was added methyl isocyanate (55 mmol, 3.2 g) in DMSO (2.5 mL) over 15 min at 20° C. The solution was stirred for 15 min and then another portion of sodium methoxide (27.5 mmol, 1.34 g) was added. After stirring for 15 min at 20° C., methyl isocyanate (14 mmol, 0.8 g) was added at this temperature. After a further 15 min, the reaction mixture was allowed to warm to room temperature and was stirred overnight. The resulting yellow suspension was poured into water (50 mL) to obtain a light yellow solution. The neutral impurities were extracted into diethyl ether (3×50 mL). The aqueous layer was acidified with concentrated hydrochloric acid to afford a white solid. The solids were collected by filtration and were washed with water. After air drying, 6.79 g (63% yield) of 3-methyl-6-(trifluoromethyl)uracil was obtained as a white solid: mp 235–237° C. EI-HRMS m/e calcd for $C_6H_5F_3N_2O_2$ (M+) 194.0303, found 194.0303.

b) Preparation of 1,3-dimethyl-6-(trifluoromethyl)uracil

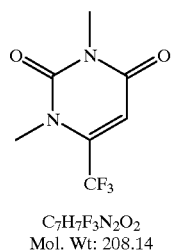

$C_7H_7F_3N_2O_2$
Mol. Wt: 208.14

To a suspension of 3-methyl-6-(trifluoromethyl)uracil (20.6 mmol, 4.0 g) and powdered potassium carbonate (41.2 mmol, 5.7 g) in DME (30 mL) was added methyl iodide (82.4 mmol, 5.13 mL). Then, the reaction mixture was refluxed for 4 h at which time the TLC analysis of the reaction mixture indicated the absence of starting material. The reaction mixture was cooled to room temperature and was diluted with water (50 mL). Then, the DME was removed under reduced pressure to afford a white suspension. The solids were collected by filtration and washed with water. After air drying, 3.55 g (83% yield) of 1,3-dimethyl-6-(trifluoromethyl)uracil was obtained as a white solid: mp 85–87° C. EI-HRMS m/e calcd for $C_7H_7F_3N_2O_2$ (M+) 208.0459, found 208.0460.

c) Preparation of 1,3-dimethyl-5-iodo-6-(trifluoromethyl) uracil

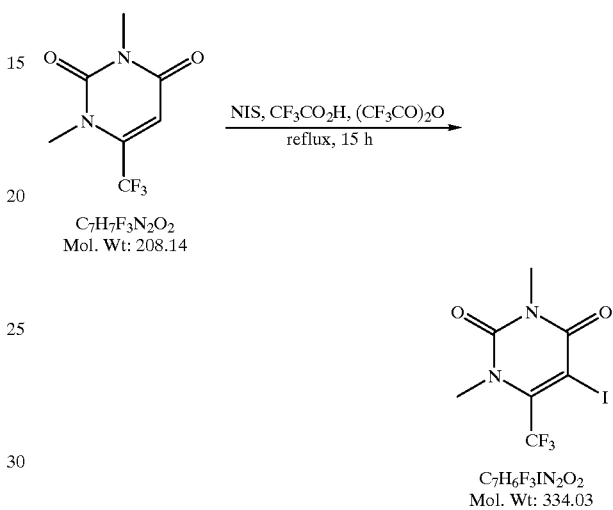

$C_7H_7F_3N_2O_2$
Mol. Wt: 208.14

$C_7H_6F_3IN_2O_2$
Mol. Wt: 334.03

A mixture of 1,3-dimethyl-6-(trifluoromethyl)uracil (16.91 mmol, 3.52 g), trifluoroacetic acid (20 mL) and trifluoroacetic anhydride (5 mL) was refluxed for 5 min. Then, NIS (16.91 mmol, 3.8 g) was added and the resulting mixture was stirred for 15 h at which time the TLC analysis of the reaction mixture indicated the presence of some starting material. Another portion of NIS (8.45 mmol, 1.9 g) was added and reflux was continued for another 5 h. The reaction mixture was cooled to room temperature and was poured slowly into a saturated potassium carbonate solution (100 mL). Then, sodium thiosulfite solution was added to remove the excess iodine color. The resulting solids were collected by filtration and washed with water. After air drying, 3.73 g (66% yield) of 1,3-dimethyl-5-iodo-6-(trifluoromethyl)uracil was obtained as a white solid: mp 149–151° C. EI-HRMS m/e calcd for $C_7H_6F_3IN_2O_2$ (M+) 333.9426, found 333.9436.

d) Preparation of N-[(1,1-dimethylethoxy)carbonyl]-4-(1,3-dimethyl-2,4-dioxo-6-(trifluoromethyl)-5-pyrimidinyl)-L-phenylalanine methyl ester

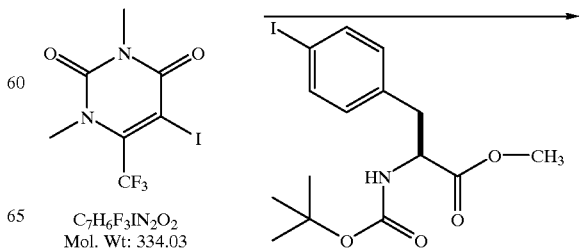

$C_7H_6F_3IN_2O_2$
Mol. Wt: 334.03

53

-continued

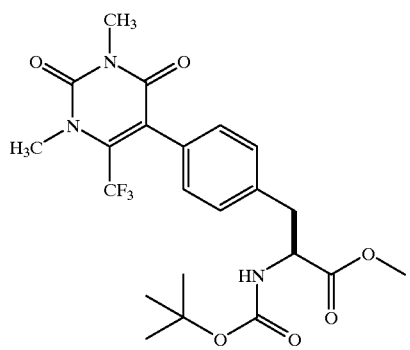

C$_{22}$H$_{26}$F$_3$N$_3$O$_6$
Mol. Wt: 485.45

To a suspension of zinc dust (33 mmol, 1.96 g) in THF (3 mL) was added 1,2-dibromoethane (3 mmol, 0.261 mL) at room temperature. This suspension was heated to 60–65° C. with a heat gun until evolution of ethylene gas ceased. The suspension was cooled to room temperature, trimethylchlorosilane (1.5 mmol, 0.19 mL) was added and the mixture was stirred for 15 min. A suspension of 1,3-dimethyl-5-iodo-6-(trifluoromethyl)uracil (10 mmol, 3.34 g) in DMA (8 mL) was warmed to obtain a clear solution and was added in one portion to the reaction mixture. After addition, the mixture was heated to 70° C. The internal temperature of the reaction mixture rose to 75 ° C. due to the exothermic reaction. The reaction mixture was stirred at 70° C. for approximately 3 h at which time TLC of an aliquot, which had been quenched with saturated ammonium chloride, indicated the absence of starting material. The reaction mixture was diluted with THF (5 mL), cooled to room temperature and excess zinc dust was allowed to settle.

The above solution of zinc compound (10 mmol) was added to a solution of Pd(dba)$_2$ (1.0 mmol, 520 mg), trifurylphosphine (TFP) (4.0 mmol, 0.93 g) and N-[(1,1-dimethylethoxy)carbonyl]-4-iodo-L-phenylalanine methyl ester (7 mmol, 2.84 g) in THF (10 mL) at room temperature and the light yellow mixture was stirred for 12 h at 45° C. The reaction mixture was poured into a saturated ammonium chloride solution (100 mL) and was extracted with ethyl acetate (3×75 mL). The combined extracts were washed with brine solution (150 mL) and were dried over anhydrous magnesium sulfate. Filtration of the drying agent and concentration gave the crude product which was purified by silica gel chromatography using a Biotage (40m) column to obtain 1.45 g (42% yield) of N-[(1,1-dimethylethoxy)carbonyl]-4-(1,3-dimethyl-2,4-dioxo-6-(trifluoromethyl)-5-pyrimidinyl)-L-phenylalanine methyl ester as an amorphous white solid. ES-HRMS m/e calcd for C$_{22}$H$_{26}$NF$_3$N$_3$O$_6$ (M+Na) 508.1666, found 508.1670.

54 e) Preparation of 4-(1,3-dimethyl-2,4-dioxo-6-(trifluoromethyl)-5-pyrimidinyl)-L-phenylalanine methyl ester hydrochloride salt

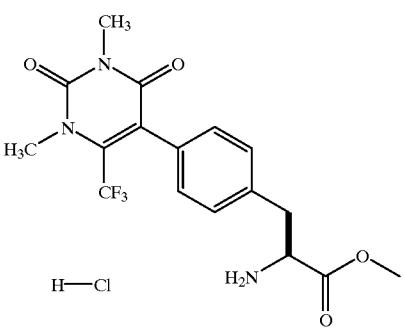

C$_{17}$H$_{19}$ClF$_3$N$_3$O$_4$
Mol. Wt: 421.80

The solid N-[(1,1-dimethylethoxy)carbonyl]-4-(1,3-diethyl-6)-2,4-dioxo-(trifluoromethyl)-5-pyrimidinyl)-L-phenylalanine methyl ester (2.92 mmol, 1.42 g) was treated with 4N hydrochloric acid in dioxane (28 mmol, 7 mL) at room temperature and the solution was stirred for 2 h. The reaction mixture was diluted with dichloromethane (5 mL) and was concentrated under reduced pressure on a rotary evaporator. The residue was diluted with diethyl ether to form a light brown solid. The solids were collected by filtration and washed with diethyl ether. After drying, 1.21 g (91% yield) of 4-(1,3-dimethyl-2,4-dioxo-6-(trifluoromethyl)-5-pyrimidinyl)-L-phenylalanine methyl ester hydrochloride salt was obtained as a light brown solid: mp 244–247° C. ES-HRMS m/e calcd for C$_{17}$H$_{18}$F$_3$N$_3$O$_4$ (M+H) 386.1322, found 386.1319.

f) Preparation of N-[(2,6-dichlorophenyl)carbonyl]-4-(1,3-dimethyl-2,4-dioxo-6-(trifluoromethyl)-5-pyrimidinyl)-L-phenylalanine methyl ester

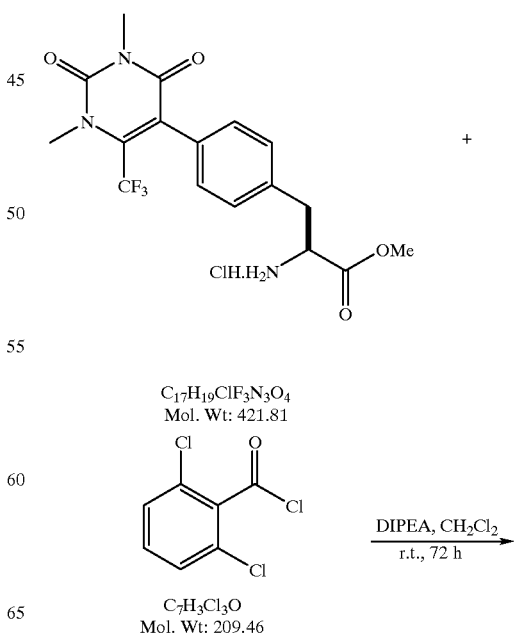

C$_{17}$H$_{19}$ClF$_3$N$_3$O$_4$
Mol. Wt: 421.81

C$_7$H$_3$Cl$_3$O
Mol. Wt: 209.46

DIPEA, CH$_2$Cl$_2$
r.t., 72 h

-continued

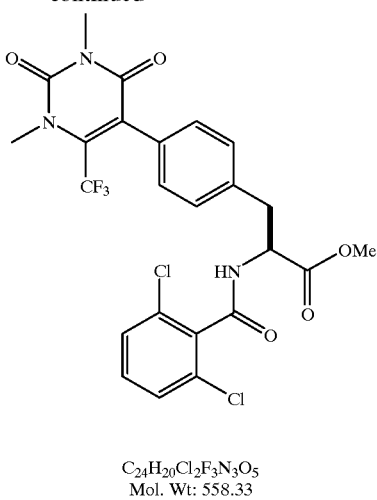

C24H20Cl2F3N3O5
Mol. Wt: 558.33

To a suspension of 4-(1,3-dimethyl-2,4-dioxo-6-(trifluoromethyl)-5-pyrimidinyl)-L-phenylalanine methyl ester hydrochloride salt (1.0 mmol, 421 mg) and 2,6-dichlorobenzoyl chloride (1.1 mmol, 0.235 g) in dichloromethane (3 mL) was added diisopropylethylamine (4.4 mmol, 0.622 mL) at room temperature. After 1 min, everything went into solution and the light brown solution was stirred for 72 h at room temperature. The resulting dark brown solution was diluted with dichloromethane (25 mL). The dichloromethane layer was washed successively with 1N hydrochloric acid (2×25 mL), saturated sodium bicarbonate solution (25 mL), and brine solution (25 mL) and was dried over anhydrous magnesium sulfate. Filtration of the drying agent and concentration of the solvent gave a crude product, which was purified by silica gel chromatography using a Biotage (40s) column to afford 0.541 g (97% yield) of N-[1-(2,6-dichlorophenyl)carbonyl]-4-(1,3-dimethyl-2,4-dioxo-6-(trifluoromethyl)-5-pyrimidinyl)-L-phenylalanine methyl ester as an amorphous white solid. ES-HRMS m/e calcd for $C_{24}H_{20}Cl_2F_3N_3O_5$ (M+Na) 580.0624, found 580.0629.

g) Preparation of N-[(2,6-dichlorophenyl)carbonyl]-4-(1,3-dimethyl-2,4-dioxo-6-(trifluoromethyl)-5-pyrimidinyl)-L-phenylalanine

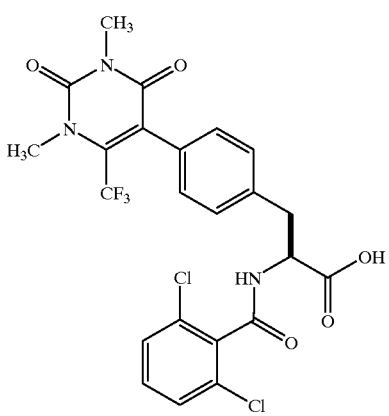

C23H18Cl2F3N3O5
Mol. Wt: 544.31

To a suspension of N-[1-(2,6-dichlorophenyl)carbonyl]4-(1,3-dimethyl-2,4-dioxo-6-(trifluoromethyl)-5-pyrimidinyl)-L-phenylalanine methyl ester (0.422 mmol, 0.236 g) in pyridine (15 mL) was added lithium iodide (4.22 mmol, 0.571 g) at room temperature. The mixture was heated to reflux for 15 h. The reaction mixture was cooled to room temperature, diluted with 1N hydrochloric acid and extracted with ethyl acetate (2×25 mL). The combined organic extracts were washed with brine solution (50 mL) and were dried over anhydrous magnesium sulfate. Filtration of the drying agent and concentration of the filtrate afforded 201 mg (87% yield) of N-[1-(2,6-dichlorophenyl)carbonyl]-4-(1,3-dimethyl-2,4-dioxo-6-(trifluoromethyl)-5-pyrimidinyl)-L-phenylalanine as a light yellow solid: mp 125–128° C. ES-HRMS m/e calcd for $C_{23}H_{18}Cl_2F_3N_3O_5$ (M+Na) 566.0469, found 566.0468.

Example 22

Preparation of N-[(2-chloro-6-methylphenyl)carbonyl]-4-[1,3-dimethyl-2,4-dioxo-6-(trifluoromethyl)-5-pyrimidinyl]-L-phenylalanine

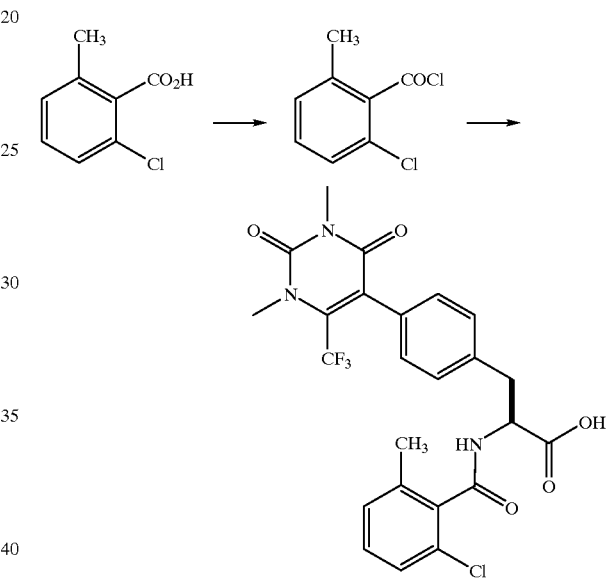

Molecular Weight = 523.89
Molecular Formula = C24H21ClF3N3O5

A solution of 2-chloro-6-methylbenzoic acid (190 mg, 1.14 mmol) in dichloromethane (7 mL) containing DMF (4 drops) was treated with oxalyl chloride (0.42 mL, 4.8 mmol) and the mixture was stirred for 2 h. The mixture was concentrated, azeotroping with toluene to remove traces of oxalyl chloride and the residue was used directly in the next step. A mixture of the above prepared acid chloride, 4-(1,3-dimethyl-2,4-dioxo-6-(trifluoromethyl)-5-pyrimidinyl)-L-phenylalanine methyl ester hydrochloride salt (423 mg, 1.003 mmol) in dichloromethane (5 mL) was treated with DIPEA (0.625 mL, 4.46 mmol) and the resulting light brown solution was stirred for 3 days. The mixture was concentrated, diluted with ethyl acetate, washed with 1 N HCl and brine solution and was dried over magnesium sulfate. Filtration and evaporation afforded a residue, which was purified by silica gel chromatography using a Biotage column (40s) to give N-[(2-chloro-6-methylphenyl)carbonyl]-4-[1,3-dimethy-2,4-dioxo-6-(trifluoromethyl)-5-pyrimidinyl]-L-phenylalanine methyl ester as a white foam (179 mg, 33%). ES-HRMS m/e calcd for $C_{25}H_{23}ClN_3O_5$ (M+Na) 560.1171, found 560.1172.

A solution of N-[(2-chloro-6-methylphenyl)carbonyl]-4-(1,3-dimethy-2,4-dioxo-6-(trifluoromethyl)-5-pyrimidinyl)-L-phenylalanine methyl ester (260 mg, 0.48 mmol), obtained as in the above experiment, and lithium iodide (6534 mg, 4.8 mmol) in pyridine (14 mL) was heated to reflux overnight. The mixture was diluted with 1 N HCl and extracted with ethyl acetate. The combined extracts were washed with brine solution and dried over magnesium sulfate, filtered and evaporated. The residue was triturated with ether, hexane and dichloromethane to give N-[(2-chloro-6-methylphenyl)carbonyl]-4-[1,3-dimethyl-2,4-dioxo-6-(trifluoromethyl)-5-pyrimidinyl]-L-phenylalanine (205 mg, 81%) as a white solid: mp 243–247° C. ES-HRMS m/e calcd for $C_{24}H_{21}ClF_3N_3O_5$ (M+Na) 546.1014, found 546.1013.

Example 23

Preparation of N-[[2-fluoro-6-(trifluoromethyl)phenyl]carbonyl]-4-(1,3-dimethy-2,4-dioxo-6-(trifluoromethyl)-5-pyrimidinyl)-L-phenylalanine

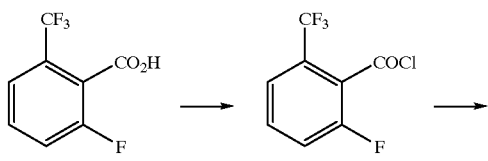

Molecular Weight = 226.56
Molecular Formula = C8H3ClF4O

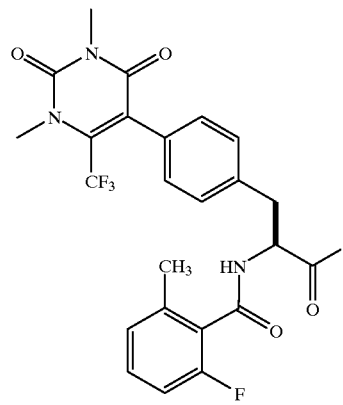

Molecular Weight = 559.44
Molecular Formula = C25H20F7N3O4

A solution of 2-fluoro-6-trifluoromethylbenzoic acid (125 mg, 0.60 mmol) (Aldrich 33080-9) in dichloromethane (3 mL) containing DMF (2 drops) was treated with oxalyl chloride (0.21 mL, 2.4 mmol) and the mixture was stirred for 2 h. The mixture was concentrated, azeotroping with toluene to remove traces of oxalyl chloride and the residue was used directly in the next step.

A mixture of the above prepared acid chloride, 4-(1,3-dimethyl-2,4-dioxo-6-(trifluoromethyl)-5-pyrimidinyl)-L-phenylalanine methyl ester hydrochloride salt (210 mg, 0.50 mmol) in dichloromethane (3 mL) was treated with DIPEA (0.336 mL, 2.4 mmol) and the resulting light brown solution was stirred for 3 days. The mixture was concentrated, diluted with ethyl acetate, washed with 1 N HCl and brine solution and was dried over magnesium sulfate. Filtration and evaporation afforded a residue, which was purified by silica gel chromatography using a Biotage column (40s) to give N-[[2-fluoro-6-(trifluoromethyl)phenyl]carbonyl]-4-(1,3-dimethy-2,4-dioxo-6-(trifluoromethyl)-5-pyrimidinyl)-L-phenylalanine methyl ester as a white foam (179 mg, 62%). ES-HRMS m/e calcd for $C_{25}H_{20}F_7N_3O_5$ (M+Na) 598.1183, found 598.1186.

A solution of N-[[2-fluoro-6-(trifluoromethyl)phenyl]carbonyl]-4-(1,3-dimethy-2,4-dioxo-6-(trifluoromethyl)-5-pyrimidinyl)-L-phenylalanine methyl ester (266 mg, 0.46 mmol), obtained as in the above experiment, and lithium iodide (624 mg, 4.6 mmol) in pyridine (14 mL) was heated to reflux overnight. The mixture was diluted with 1 N HCl and extracted with ethyl acetate. The combined extracts were washed with brine solution and dried over magnesium sulfate, filtered and evaporated. The residue was triturated with ether and dichloromethane to give N-[[2-fluoro-6-(trifluoromethyl)phenyl]carbonyl]-4-(1,3-dimethyl-2,4-dioxo-6-(trifluoromethyl)-5-pyrimidinyl)-L-phenylalanine (167 mg, 64%) as a white solid: mp 122–125° C. ES-HRMS m/e calcd for $C_{24}H_{18}F_7N_3O_5$ (M+Na) 584.1027, found 584.1028.

Example 24

N-[(2-chloro-6-methylphenyl)carbonyl]-4-(1,3-dimethyl-2,4-dioxo-5-pyrimidinyl)-3-methyl-L-phenylalanine a) Preparation of 4-[(1,1-dimethylethoxy)carbonyl]amino-3-methylbenzyl alcohol

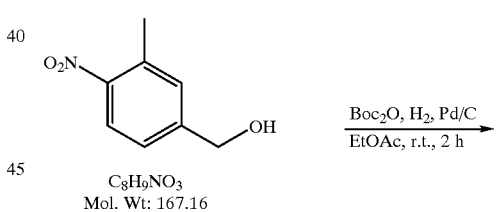

C8H9NO3
Mol. Wt: 167.16

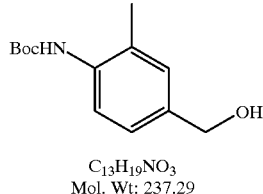

C13H19NO3
Mol. Wt: 237.29

A mixture of 4-nitro-3-methylbenzyl alcohol (56.53 mmol, 9.45 g), di-tert-butyl dicarbonate (63 mmol, 13.74 g) and palladium on charcoal (450 mg) in ethyl acetate (240 mL) was hydrogenated for 2 h at room temperature. Then, the reaction mixture was filtered through a pad of celite washing with ethyl acetate (50 mL). The filtrate was concentrated under vacuum to obtain 10.18 g (76% yield) of 4-[(1,1-dimethylethoxy)carbonyl]amino-3-methylbenzyl alcohol as a light yellow solid. EI-HRMS m/e calcd for $C_{13}H_{19}NO_3$ ($M^+$) 237.0126, found 237.0129.

b) Preparation of 4-[[(1,1-dimethylethoxy)carbonyl]amino]-3-methylbenzaldehyde

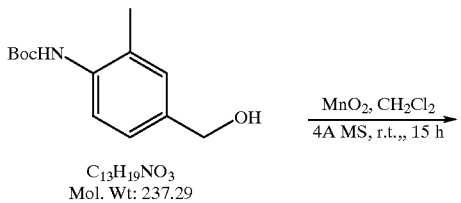

C₁₃H₁₉NO₃
Mol. Wt: 237.29

MnO₂, CH₂Cl₂
4A MS, r.t., 15 h

BocHN

CHO

C₁₃H₁₇NO₃
Mol. Wt: 235.28

To a solution of 4-[(1,1-dimethylethoxy)carbonyl]amino-3-methylbenzyl alcohol (42.9 mmol, 10.18 g) in dichloromethane (85 mL) was added manganese dioxide (138 mmol, 12 g) and 4A molecular sieves (6 g) at room temperature. The reaction mixture was stirred for 76 h at room temperature and was filtered through a pad of celite washing with dichloromethane. The filtrate was concentrated under reduced pressure and the residue was purified by silica gel chromatography using a Biotage (40m) column to obtain 7.82 g (77% yield) of 4-[[(1,1-dimethylethoxy)carbonyl]amino]-3-methylbenzaldehyde as a white solid: mp 109–111° C. EI-HRMS m/e calcd for C₁₃H₁₇NO₃ (M⁺) 235.1208, found 235.1207.

c) Preparation of N-(benzyloxycarbonyl)-4-[[(1,1-dimethylethoxy)carbonyl]amino]-3-methyldehydrophenylalanine methyl ester

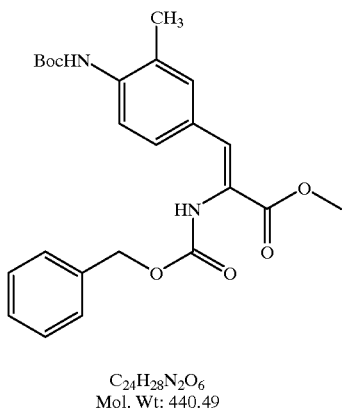

C₂₄H₂₈N₂O₆
Mol. Wt: 440.49

To a solution of N-(benzyloxycarbonyl)-a-phosphonoglycine triethyl ester (18 mmol, 5.96 g) (Aldrich Chemical Company) in dichloromethane (30 mL) was added tetramethylguanidine (18 mmol, 2.07 g) at room temperature. The reaction mixture was stirred for 1 h at room temperature and it was cooled to –30° C. Then, a solution of 4-[[(1,1-dimethylethoxy)carbonyl]amino]-3-methylbenzaldehyde (15 mmol, 3.52 g) in dichloromethane (12.5 mL) was added in one portion. After 30 min at this temperature, the reaction mixture was allowed to warm to room temperature and was stirred for 15 h. Then, the reaction mixture was diluted with diethyl ether (100 mL) and was washed successively with 0.5N hydrochloric acid (2×50 mL), saturated sodium bicarbonate solution (100 mL), brine solution (100 mL) and was dried over anhydrous magnesium sulfate. Filtration of the drying agent and concentration gave a crude product, which was purified by silica gel chromatography using a Biotage (40m) column to obtain 3.87 g (58% yield) of N-(benzyloxycarbonyl)-4-[[(1,1-dimethylethoxy)carbonyl]amino]-3-methyl-dehydrophenylalanine methyl ester as a white solid. EI-HRMS m/e calcd for C₂₄H₂₈N₂O₆ (M⁺) 440.1527, found 440.1524.

d) Preparation of N-(benzyloxycarbonyl)-4-[[(1,1-dimethylethoxy)carbonyl]amino]-3-methyl-L-phenylalanine methyl ester

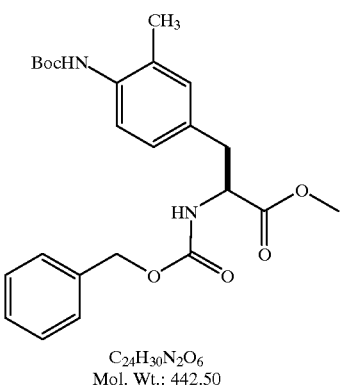

C₂₄H₃₀N₂O₆
Mol. Wt.: 442.50

A stream of argon was passed through a solution of N-(benzyloxycarbonyl)-4-[[(1,1-dimethylethoxy)carbonyl]amino]-3-methyl-dehydrophenylalanine methyl ester (8.08 mmol, 3.56 g) in methanol (25 mL) in a Parr pressure vessel overnight. Then, the catalyst, (+)-1,2-bis((2S,5S)-2,5-dimethylphospholano)benzene(cyclooctadiene)rhodium (I) trifluoromethanesulfonate [[Rh(COD)(S,S)-(me)DuPHOS]+TfO-] (~40 mg) was added under a stream of argon in a glove box. The solution was stirred under a hydrogen pressure (60 psi) at room temperature for 22 h. The resulting solution was concentrated and the crude product was purified by silica gel chromatography using a Biotage (40m) column to obtain 2 g (55% yield) of N-(benzyloxycarbonyl)-4-[[(1,1-dimethylethoxy)carbonyl]amino]-3-methyl-L-phenylalanine methyl ester as an amorphous white solid. EI-HRMS m/e calcd for C₂₄H₃₀N₂O₆ (M⁺) 442.1627, found 442.1629.

e) Preparation of N-(benzyloxycarbonyl)-4-amino-3-methyl-L-phenylalanine methyl ester hydrochloride salt

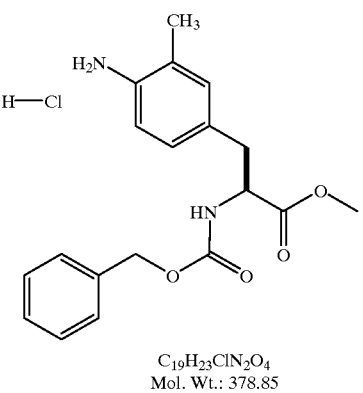

C₁₉H₂₃ClN₂O₄
Mol. Wt.: 378.85

To a solution of N-(benzyloxycarbonyl)-4-[(1,1-dimethylethoxy)carbonyl]amino-3-methyl-L-phenylalanine methyl ester (4.52 mmol, 2 g) in dioxane (12 mL) was added 4N hydrochloric acid in dioxane (48 mmol, 2 mL) at room temperature and the solution was stirred for approximately 2 h as a white precipitate was formed. The solids were diluted with diethyl ether, the mother liquor was decanted and the residue was dried first on a rotary evaporator and then under high vacuum to afford 1.487 g (87% yield) of N-(benzyloxycarbonyl)-4-amino-3-methyl-L-phenylalanine methyl ester hydrochloride salt as an amorphous yellow solid. FAB-HRMS m/e calcd for $C_{19}H_{22}N_2O_4$ (M+H) 343.0142, found 343.0144.

f) Preparation of N-(benzyloxycarbonyl)-4-iodo-3-methyl-L-phenylalanine methyl ester

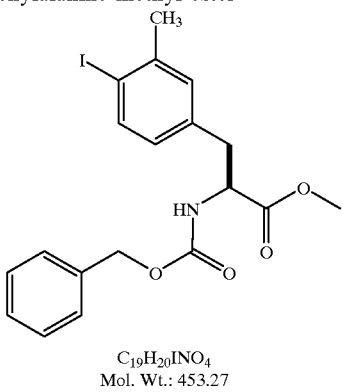

$C_{19}H_{20}INO_4$
Mol. Wt.: 453.27

A suspension of sulfuric acid (0.3 mL), water (36 mL) and N-(benzyloxycarbonyl)-4-amino-3-methyl-L-phenylalanine methyl ester hydrochloride salt (2.9 mmol, 1.1 g) was heated to obtain a clear solution. Then, it was cooled to −1° C. (ice-bath) and a solution of sodium nitrite (5.8 mmol, 400 mg) in water (8 mL) was added dropwise. The reaction mixture was stirred for 30 min, and a solution of potassium iodide (8.7 mmol, 1.5 g) in water (6 mL) was added to obtain a brown suspension. After stirring for 30 min, the reaction mixture was allowed to warm to room temperature and was stirred for 1 h. Then, the reaction mixture was diluted with water (100 mL) and was extracted with ethyl acetate (3×50 mL). The combined extracts were washed with saturated sodium bisulfite solution (100 mL) and brine solution (100 mL) and were dried over anhydrous magnesium sulfate. Filtration of the drying agent and concentration gave a crude product, which was purified by silica gel chromatography using a Biotage (40m) column to afford 0.84 g (64% yield) of N-(benzyloxycarbonyl)-4-iodo-3-methyl-L-phenylalanine methyl ester as an amorphous white solid. ES-HRMS m/e calcd for $C_{19}H_{20}INO_4$ (M+Na) 476.0329, found 476.0336.

g) Preparation of N-(benzyloxycarbonyl)-4-(1,3-dimethyl-2,4-dioxo-5-pyrimidinyl)-3-methyl-L-phenylalanine methyl ester

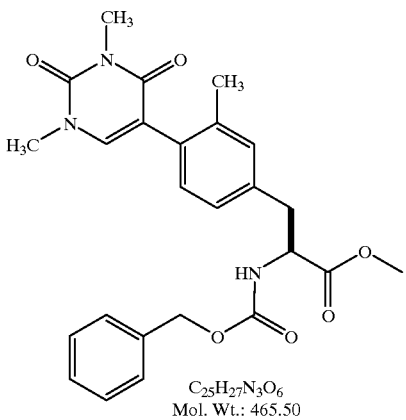

$C_{25}H_{27}N_3O_6$
Mol. Wt.: 465.50

To a suspension of zinc dust (15 mmol, 0.98 g) in THF (1.5 mL) was added 1,2-dibromoethane (1 mmol, 0.13 mL) at room temperature. This suspension was heated to 60–65° C. with a heat gun until evolution of ethylene gas ceased. Then, the suspension was cooled to room temperature and trimethylchiorosilane (0.5 mmol, 70 uL) was added and the mixture was stirred for 15 min. A suspension of 5-iodo-1,3-dimethyl uracil (2.5 mmol, 665 mg) in DMA (2 mL) was warmed to obtain a clear solution and was added in one portion to the reaction mixture. After addition, the mixture was heated to 70° C. The reaction mixture was stirred at 70° C. for approximately 3 h, at which time TLC of an aliquot, which had been quenched with saturated ammonium chloride, indicated the absence of starting material. The mixture was diluted with THF (2 mL), allowed to cool room temperature and the excess zinc dust was allowed to settle.

The above prepared solution of zinc compound (2.5 mmol) was added to a solution of $Pd(dba)_2$ (0.05 mmol, 27 mg), trifiirylphosphine (TFP) (0.2 mmol, 50 mg) and N-(benzyloxycarbonyl)-4-iodo-3-methyl-L-phenylalanine methyl ester (0.5 mmol, 227 mg) in THF (2 mL) at room temperature and the resulting light yellow mixture was stirred for 15 h at 45° C. The reaction mixture was then poured into a saturated ammnonium chloride solution and was extracted with ethyl acetate (3×30 mL). The combined extracts were washed with brine solution (50 mL) and dried over anhydrous magnesium sulfate. Filtration of the drying agent and concentration gave the crude product, which was purified by silica gel chromatography using a Biotage (40m) column to obtain 161 mg (69% yield) of N-(benzyloxycarbonyl)-4-(1,3-dimethyl-2,4-dioxo-5-pyrimidinyl)-3-methyl-L-phenylalanine methyl ester as an amorphous white solid. ES-HRMS m/e calcd for $C_{25}H_{27}N_3O_6$ (M+Na) 488.1792, found 488.1801.

h) Preparation of 4-(1,3-dimethyl-2,4-dioxo-5-pyrimidinyl)-3-methyl-L-phenylalanine methyl ester

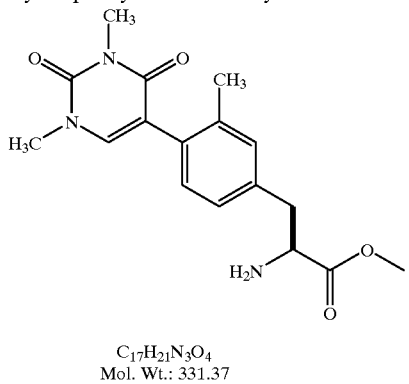

$C_{17}H_{21}N_3O_4$
Mol. Wt.: 331.37

A mixture of N-(benzyloxycarbonyl)-4-(1,3-dimethyl-2,4-dioxo-5-pyrimidinyl)-3-methyl-L-phenylalanine methyl ester (0.34 mmol, 159 mg), cyclohexene (1 mL) and 10% palladium on carbon (100 mg) in ethanol (3 mL) was heated to reflux for 20 min. Then, it was filtered through a pad of celite and the pad was washed with ethanol (10 mL). The combined filtrate was concentrated and the residue was dried under high vacuum to afford 96 mg (85% yield) of 4-(1,3-dimethyl-2,4-dioxo-5-pyrimidinyl)-3-methyl-L-phenylalanine methyl ester as a sticky yellow solid. ES-HRMS m/e calcd for $C_{17}H_{21}N_3O_4$ (M+Na) 354.1424, found 354.1424.

i) Preparation of N-[(2-chloro-6-methylphenyl)carbonyl]-4-(1,3-dimethyl-2,4-dioxo-5-pyrimidinyl)-3-methyl-L-phenylalanine methyl ester

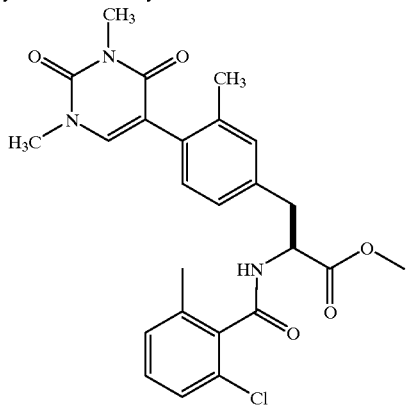

C$_{25}$H$_{26}$ClN$_3$O$_5$
Mol. Wt.: 483.94

To a suspension of 4-(1,3-dimethyl-2,4-dioxo-5-pyrimidinyl)-3-methyl-L-phenylalanine methyl ester (0.125 mmol, 46 mg), HBTU (0.125 mmol, 47.5 mg) and 2-chloro-6-methylbenzoic acid (0.137 mmol, 25 mg) in DMF (2 mL) was added diisopropylethylamine (0.312 mmol, 44 uL) at room temperature. After 5 min, everything went into solution and the clear yellow solution was stirred for 72 h at room temperature. The resulting dark-brown solution was diluted with ethyl acetate (30 mL). The ethyl acetate layer was washed successively with 1N hydrochloric acid (2×30 mL), saturated sodium bicarbonate solution (30 mL), and brine solution (30 mL) and was dried over anhydrous magnesium sulfate. Filtration of the drying agent and concentration of the solvent gave the crude product which was purified by silica gel chromatography using a Biotage (40s) column to afford 42 mg (70% yield) of N-[(2-chloro-6-methylphenyl)carbonyl]-4-(1,3-dimethyl-2,4-dioxo-5-pyrimidinyl)-3-methyl-L-phenylalanine methyl ester as a oily residue. ES-HRMS m/e calcd for C$_{25}$H$_{26}$ClN$_3$O$_5$ (M+Na) 506.1454, found 506.1459.

j) Preparation of N-[(2-chloro-6-methylphenyl)carbonyl]-4-(1,3-dimethyl-2,4-dioxo-5-pyrimidinyl)-3-methyl-L-phenylalanine

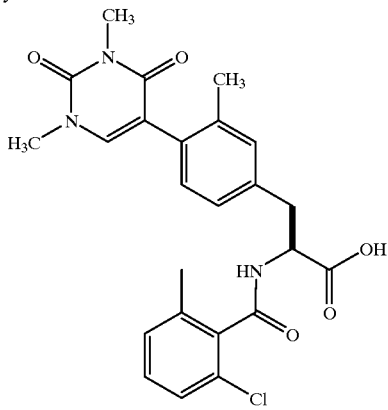

C$_{24}$H$_{24}$ClN$_3$O$_5$
Mol. Wt.: 469.92

To a suspension of N-[(2-chloro-6-methylphenyl)carbonyl]-4-(1,3-dimethyl-2,4-dioxo-5-pyrimidinyl)-3-methyl-L-phenylalanine methyl ester (0.083 mmol, 40 mg) in ethanol (1 mL) was added aqueous 1.0 N sodium hydroxide (0.2 mL) at room temperature. The mixture was stirred for 2 h at room temperature. Then, the ethanol was removed under reduced pressure and the residue was diluted with water (5 mL). The aqueous solution was washed with diethyl ether (20 mL) to remove any neutral impurities. The aqueous layer was acidified with 1.0 N HCl and the product was extracted into ethyl acetate (2×25 mL). The combined organic extracts were washed with brine solution (50 mL) and were dried over anhydrous magnesium sulfate. Filtration of the drying agent and concentration of the filtrate afforded 34 mg (87% yield) of N-[(2-chloro-6-methylphenyl)carbonyl]-4-(1,3-dimethyl-2,4-dioxo-5-pyrimidinyl)-3-methyl-L-phenylalanine as an amorphous white solid. ES-HRMS m/e calcd for C$_{24}$H$_{24}$ClN$_3$O$_5$ (M+Na) 492.1295, found 492.1301.

Example 25

Preparation of N-[(2,6-dichlorophenyl)carbonyl]-4-(1,3-dimethyl-2,4-dioxo-5-pyrimidinyl)-3-methyl-L-phenylalanine a) Preparation of N-[(2,6-dichlorophenyl)carbonyl]-4-(1,3-dimethyl-2,4-dioxo-5-pyrimidinyl)-3-methyl-L-phenylalanine methyl ester

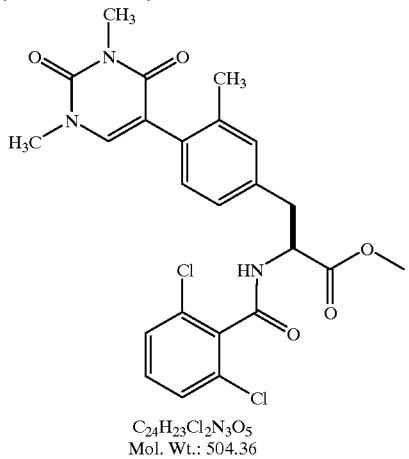

C$_{24}$H$_{23}$Cl$_2$N$_3$O$_5$
Mol. Wt.: 504.36

To a suspension of 4-(1,3-dimethyl-2,4-dioxo-5-pyrimidinyl)-3-methyl-L-phenylalanine methyl ester (0.128 mmol, 47 mg) and 2,6-dichlorobenzoyl chloride (0.153 mmol, 32 mg) in dichloromethane (1 mL) was added diisopropylethylamine (0.45 mmol, 77 uL) at room temperature. After 5 min, everything went into solution and the clear yellow solution was stirred for 15 h at room temperature. The resulting brown solution was diluted with dichloromethane (25 mL). The dichloromethane layer was washed successively with 1N hydrochloric acid (2×25 mL), saturated sodium bicarbonate solution (25 mL), and brine solution (25 mL) and was dried over anhydrous magnesium sulfate. Filtration of the drying agent and concentration gave the crude product which was purified by silica gel chromatography using a Biotage (40m) column to afford 52 mg (81% yield) of N-[(2,6-dichlorophenyl)carbonyl]-4-(1,3-dimethyl-2,4-dioxo-5-pyrimidinyl)-3-methyl-L- phenylalanine methyl ester as an amorphous white solid. ES-HRMS m/e calcd for C$_{24}$H$_{23}$Cl$_2$N$_3$O$_5$ (M+Na) 526.0907, found 526.0912.

b) Preparation of N-[(2,6-dichlorophenyl)carbonyl]-4-(1,3-dimethyl-2,4-dioxo-5-pyrimidinyl)-3-methyl-L-phenylalanine

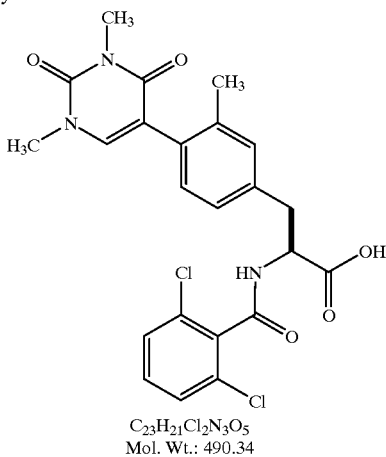

C₂₃H₂₁Cl₂N₃O₅
Mol. Wt.: 490.34

To a suspension of N-[(2,6-dichlorophenyl)carbonyl]-4-(1,3-dimethyl-2,4-dioxo-5-pyrimidinyl)-3-methyl-L-phenylalanine methyl ester (0.1 mmol, 59 mg) in ethanol (1 mL) was added aqueous 1.0 N sodium hydroxide (0.2 mL) at room temperature. The mixture was stirred for 2 h at room temperature. The ethanol was removed under reduced pressure and the residue was diluted with water (10 mL). The aqueous solution was washed with diethyl ether (20 mL) to remove any neutral impurities. The aqueous layer was acidified with 1.0 N HCl and the product was extracted into ethyl acetate (2×15 mL). The combined organic extracts were washed with brine solution (50 mL) and were dried over anhydrous magnesium sulfate. Filtration of the drying agent and concentration of the filtrate afforded 20 mg (41% yield) of N-[(2,6-dichlorophenyl)carbonyl]-4-(1,3-dimethyl-2,4-dioxo-5-pyrimidinyl)-3-methyl-L-phenylalanine as an amorphous white solid. ES-HRMS m/e calcd for $C_{23}H_{21}C_2N_3O_5$ (M+Na) 512.0752, found 512.0754.

Example 26

N-[(2,6-dichlorophenyl)carbonyl]-4-(1,3,6-trimethyl-2,4-dioxo-5-pyrimidinyl)-3-methyl-L-phenylalanine a) Preparation of N-(benzyloxycarbonyl)-4-(1,3,6-trimethyl-2,4-dioxo-5-pyrimidinyl)-3-methyl-L-phenylalanine methyl ester

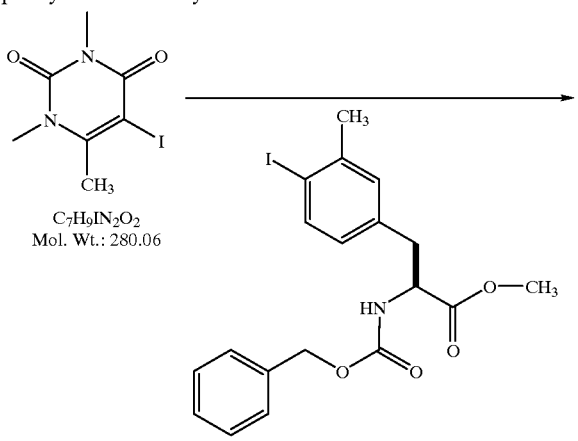

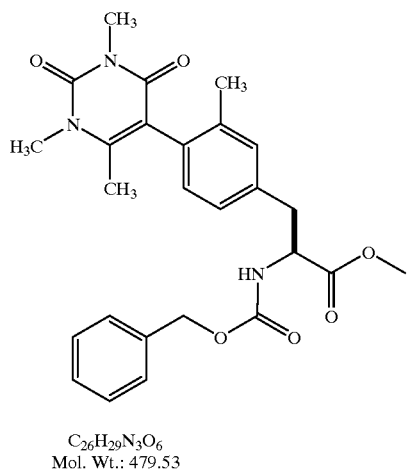

C₂₆H₂₉N₃O₆
Mol. Wt.: 479.53

To a suspension of zinc dust (15 mmol, 0.98 g) in THF (1.5 mL) was added 1,2-dibromoethane (1 mmol, 0.13 mL) at room temperature. This suspension was heated to 60–65° C. with a heat gun until evolution of ethylene gas ceased. Then, the suspension was cooled to room temperature and trimethylchlorosilane (0.5 mmol, 70 uL) was added and the mixture was stirred for 15 min. A suspension of 5-iodo-1,3,6-trimethyl uracil (2.5 mmol, 700 mg) in DMA (2 mL) was warmed to obtain a clear solution and was added in one portion to the reaction mixture. The reaction mixture was stirred at 70° C. for 3–4 h at which time TLC of an aliquot which, had been quenched with saturated ammonium chloride, indicated the absence of starting material. Then, the reaction mixture was diluted with THF (3 mL) and the excess zinc dust was allowed to settle. The above prepared solution containing the zinc compound (2.5 mmol) was added to a solution of Pd(dba)₂ (0.05 mmol, 27 mg), trifurylphosphine (TFP) (0.2 mmol, 50 mg) and N-(benzyloxycarbonyl)-4-iodo-3-methyl-L-phenylalanine methyl ester (0.5 mmol, 227 mg) in THF (2 mL) at room temperature and the light yellow mixture was stirred for 15 h at 45° C. Then, the reaction mixture was poured into a saturated ammonium chloride solution and was extracted with ethyl acetate (3×30 mL). The combined extracts were washed with brine solution (50 mL) and were dried over anhydrous magnesium sulfate. Filtration of the drying agent and concentration gave the crude product which was purified by silica gel chromatography using a Biotage (40m) column to obtain 71 mg (30% yield) of N-(benzyloxycarbonyl)-4-(1,3,6-trimethyl-2,4-dioxo-5-pyrimidinyl)- 3-methyl-L-phenylalanine methyl ester as an yellow oil. ES-HRMS m/e calcd for $C_{26}H_{29}N_3O_6$ (M+Na) 502.2173, found 502.2174.

b) Preparation of 4-(1,3,6-trimethyl-2,4-dioxo-5-pyrimidinyl)-3-methyl-L-phenylalanine methyl ester

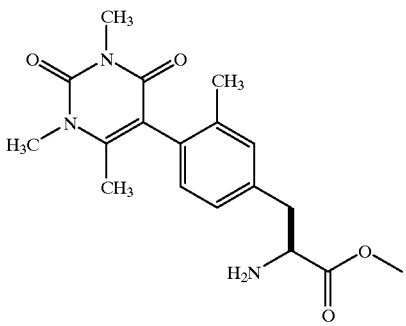

C₁₈H₂₃N₃O₄
Mol. Wt: 345.40

A mixture of N-(benzyloxycarbonyl)-4-(1,3,6-trimethyl-2,4-dioxo-5-pyrimidinyl)-3-methyl-L-phenylalanine methyl ester (0.145 mmol, 70 mg), cyclohexene (1 mL) and 10% palladium on carbon (100 mg) in ethanol (2 mL) was heated to reflux for 15 h. Then, it was filtered through a pad of celite and the pad was washed with ethanol (10 mL). The combined filtrate was concentrated under reduced pressure. The residue was dried under high vacuum to afford 36 mg (72% yield) of 4-(1,3,6-trimethyl-2,4-dioxo-5-pyrimidinyl)-3-methyl-L-phenylalanine methyl ester as a light yellow solid. ES-HRMS m/e calcd for $C_{18}H_{23}N_3O_4$ (M+Na) 368.1327, found 368.1321.

c) Preparation of N-[(2,6-dichlorophenyl)carbonyl]-4-(1,3,6-trimethyl-2,4-dioxo-5-pyrimidinyl)-3-methyl-L-phenylalanine methyl ester

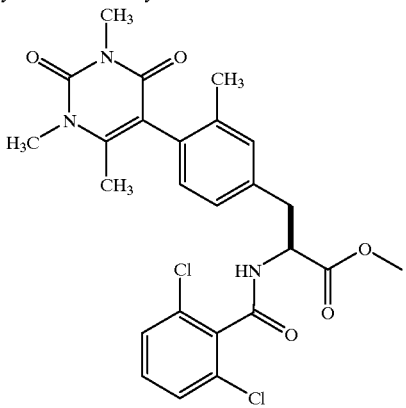

C₂₅H₂₅Cl₂N₃O₅
Mol. Wt: 518.39

To a suspension of 4-(1,3,6-trimethyl-2,4-dioxo-5-pyrimidinyl)-3-methyl-L-phenylalanine methyl ester (0.089 mmol, 34 mg) and 2,6-dichlorobenzoyl chloride (0.1 mmol, 21 mg) in dichloromethane (2 mL) was added diisopropylethylamine (0.4 mmol, 70 uL) at room temperature. After 5 min, everything went into solution and the clear yellow solution was stirred for 15 h at room temperature. The resulting brown solution was diluted with dichloromethane (25 mL). The dichloromethane layer was washed successively with 1N hydrochloric acid (2×25 mL), saturated sodium bicarbonate solution (25 mL), and brine solution (25 mL) and was dried over anhydrous magnesium sulfate. Filtration of the drying agent and concentration of the solvent gave the crude product which was purified by silica gel chromatography using a Biotage (40m) column to afford 22 mg (48% yield) of N-[(2,6-dichlorophenyl)carbonyl]-4-(1,3,6-trimethyl-2,4-dioxo-5-pyrimidinyl)-3-methyl-L-phenylalanine methyl ester as a viscous oil. ES-HRMS m/e calcd for $C_{25}H_{25}Cl_2N_3O_5$ (M+Na) 541.1065, found 541.1063.

d) Preparation of N-[(2,6-dichlorophenyl)carbonyl]-4-(1,3,6-trimethyl-2,4-dioxo-5-pyrimidinyl)-3-methyl-L-phenylalanine

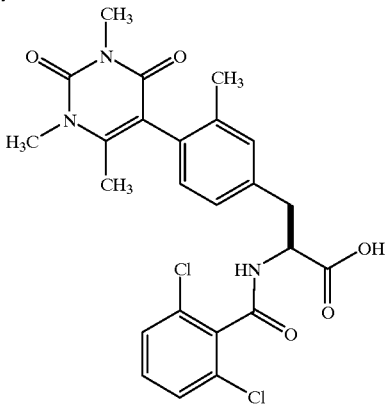

C₂₄H₂₃Cl₂N₃O₅
Mol. Wt: 504.36

To a suspension of N-[(2,6-dichlorophenyl)carbonyl]-4-(1,3,6-trimethyl-2,4-dioxo-5-pyrimidinyl)-3-methyl-L-phenylalanine methyl ester (0.04 mmol, 22 mg) in ethanol (2 mL) was added aqueous 1.0 N sodium hydroxide (0.5 mL) at room temperature. The mixture was stirred for 2 h at room temperature. The ethanol was removed under reduced pressure and the residue was diluted with water (10 mL). The aqueous solution was washed with diethyl ether (20 mL) to remove any neutral impurities. The aqueous layer was acidified with 1.0 N HCl and the product was extracted into ethyl acetate (2×15 mL). The combined organic extracts were washed with brine solution (50 mL) and were dried over anhydrous magnesium sulfate. Filtration of the drying agent and concentration of the filtrate afforded 20 mg (93% yield) of N-[(2,6-dichlorophenyl)carbonyl]-4-(1,3,6-trimethyl-2,4-dioxo-5-pyrimidinyl)-3-methyl-L-phenylalanine as an amorphous white solid. ES-HRMS m/e calcd for $C_{23}H_{21}Cl_2N_3O_5$ [(M-H)+2Na] 548.0725, found 548.0733.

Example 27

N-[(2,6-dichlorophenyl)carbonyl]-4-(1,3,6-trimethyl-2,4-dioxo-5-pyrimidinyl)-L-phenylalanine ethyl ester

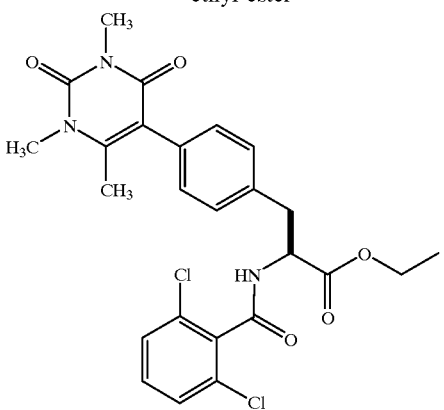

C₂₅H₂₅Cl₂N₃O₅
Mol. Wt: 518.39

To a suspension of N-[(2,6-dichlorophenyl)carbonyl]-4-(1,3,6-trimethyl-2,4-dioxo-5-pyrimidinyl)-L-phenylalanine (0.6 mmol, 300 mg) and sodium bicarbonate (3.6 mmol, 302 mg) in DMF (4 mL) was added iodoethane (3.6 mmol, 0.29 mL) at room temperature. The mixture was stirred for 72 h at room temperature. Then, the reaction mixture was poured into water (50 mL) and was extracted with ethyl acetate (3×20 mL). The combined extracts were washed with brine solution (60 mL) and were dried over anhydrous magnesium sulfate. Filtration of the drying agent and concentration of the filtrate gave the crude product which was purified by silica gel chromatography using a Biotage (40m) column to obtain 155 mg (50% yield) of N-[(2,6-dichlorophenyl)carbonyl]-4-(1,3,6-trimethyl-2,4-dioxo-5-pyrimidinyl)-L-phenylalanine ethyl ester as a crystalline white solid: mp 262–265° C. ES-HRMS m/e calcd for $C_{25}H_{25}Cl_2N_3O_5$ (M+Na) 540.1062, found 540.1049.

Example 28

Preparation of N-[(2,6-dichlorophenyl)carbonyl]-4-(1,3,6-trimethyl-2,4-dioxo-5-pyrimidinyl)-L-phenylalanine 2-[(N,N-diethyl)amino]ethyl ester

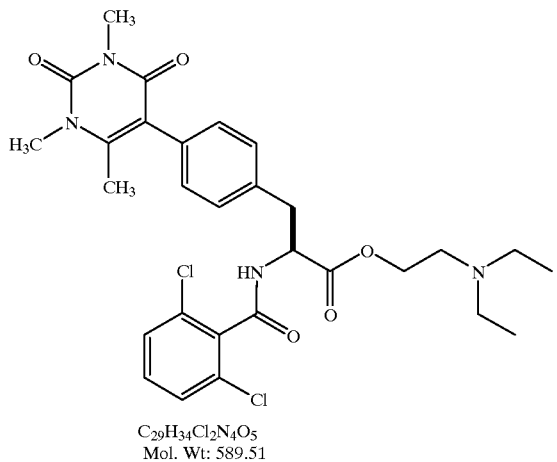

$C_{29}H_{34}Cl_2N_4O_5$
Mol. Wt: 589.51

A mixture of N-[(2,6-dichlorophenyl)carbonyl]-4-(1,3,6-trimethyl-2,4-dioxo-5-pyrimidinyl)-L-phenylalanine (320 mg, 0.65 mmol), 2-[(N,N-diethyl)amino]ethyl chloride hydrochloride (579 mg, 3.26 mmol) and potassium carbonate (451 mg, 3.27 mmol) in ethyl acetate (5 mL) and water (5 mL) was at room termperature overnight. The layers were separated and the aqueous layer was extracted with ethyl acetate. The combined extracts were washed with brine, dried over magnesium sulfate and concentrated to afford N-[(2,6-dichlorophenyl)carbonyl]-4-(1,3,6-trimethyl-2,4-dioxo-5-pyrimidinyl)-L-phenylalanine 2-[(N,N-diethyl)amino]ethyl ester (190 mg, 49%) as an amorphous white solid. ES-HRMS m/e calcd for $C_{29}H_{34}Cl_2N_4O_5$ (M+H) 589.1978, found 589.1980.

Acidification of the aqueous layer afforded recovered N-[(2,6-dichlorophenyl)carbonyl]-4-(1,3,6-trimethyl-2,4-dioxo-5-pyrimidinyl)-L-phenylalanine (167 mg).

Example 29

Preparation of N-[(2-chloro-6-methylphenyl)carbonyl]-4-(1,3,6-trimethyl-2,4-dioxo-5-pyrimidinyl)-L-phenylalanine 2-[(N,N-diethyl)amino]ethyl ester

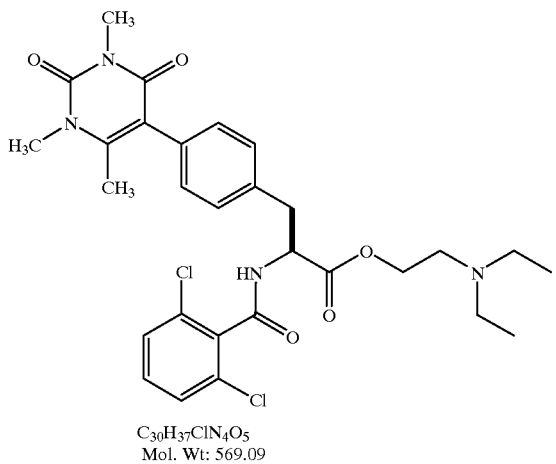

$C_{30}H_{37}ClN_4O_5$
Mol. Wt: 569.09

N-[(2-chloro-6-methylphenyl)carbonyl]-4-(1,3,6-trimethyl-2,4-dioxo-5-pyrimidinyl)-L-phenylalanine 2-[(N,N-diethyl)amino]ethyl ester was prepared from N-[(2-chloro-6-methylphenyl)carbonyl]-4-(1,3,6-trimethyl-2,4-dioxo-5-pyrimidinyl)-L-phenylalanine and 2-[(N,N-diethyl)aminoethyl chloride hydrochloride using the general procedure described in example 28 and was obtained as an amorphous white solid. ES-HRMS m/e calcd for $C_{30}H_{37}ClN_4O_5$ (M+H) 569.2525, found 569.2530.

Example 30

Preparation of N-[(2-chloro-6-methylphenyl)carbonyl]-4-(1,3,6-trimethyl-2,4-dioxo-5-pyrimidinyl)-L-phenylalanine ethyl ester

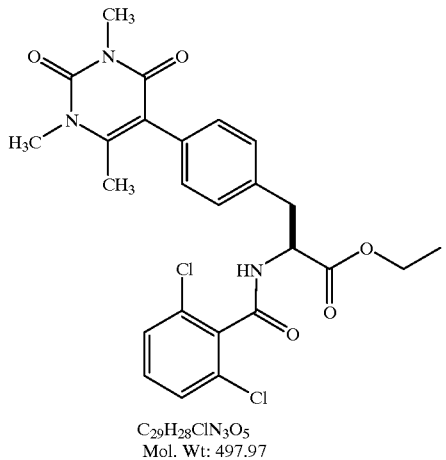

$C_{29}H_{28}ClN_3O_5$
Mol. Wt: 497.97

N-[(2-chloro-6-methylphenyl)carbonyl]-4-(1,3,6-trimethyl-2,4-dioxo-5-pyrimidinyl)-L-phenylalanine ethyl ester was prepared from N-[(2-chloro-6-methylphenyl)carbonyl]-4-(1,3,6-trimethyl-2,4-dioxo-5-pyrimidinyl)-L-phenylalanine and iodoethane using the general procedure described in example 27 and was obtained as an amorphous white solid. ES-HRMS m/e calcd for $C_{26}H_{28}ClN_3O_5$ (M+Na) 520.1610, found 520.1591.

Example 31

N-[(2,6-dichlorophenyl)carbonyl]-4-(1,3,6-trimethyl-2,4-dioxo-5-pyrimidinyl)-L-phenylalanine 2-(4-morpholino)ethyl ester a) Preparation of N-[(1,1-dimethylethoxy)carbonyl]-4-(1,3,6-trimethyl-2,4-dioxo-5-pyrimidinyl)-L-phenylalanine

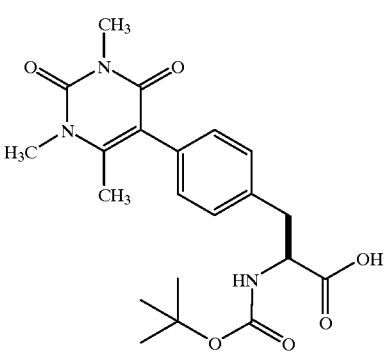

$C_{21}H_{27}N_3O_6$
Mol. Wt: 417.46

To a suspension of N-[(1,1-dimethylethoxy)carbonyl]-4-(1,3,6-trimethyl-2,4-dioxo-5-pyrimidinyl)-L-phenylalanine methyl ester (8.8 mmol, 3.79 g) in ethanol (20 mL) was added aqueous 1.0 N sodium hydroxide (17.57 mL) at room temperature. The mixture was stirred for 2 h at room temperature. Then, the mixture was diluted with water (50 ml) and the ethanol was removed under reduced pressure. The aqueous solution was washed with diethyl ether (100 mL) to remove any neutral impurities. The aqueous layer was acidified with 1.0 N HCl and the product was extracted into ethyl acetate (2×100 mL). The combined organic extracts were washed with brine solution (200 mL) and were dried over anhydrous magnesium sulfate. Filtration of the drying agent and concentration of the filtrate afforded 3.44 g (94% yield) of N-[(1,1-dimethylethoxy)carbonyl]-4-(1,3,6-trimethyl-2,4-dioxo-5-pyrimidinyl)-L-phenylalanine as a light brown foam solid. ES-HRMS m/e calcd for $C_{21}H_{27}N_3O_6$ (M+Na) 440.1792, found 440.1792.

b) Preparation of N-[(1,1-dimethylethoxy)carbonyl]-4-(1,3,6-trimethyl-2,4-dioxo-5-pyrimidinyl)-L-phenylalanine 2-(4-morpholino)ethyl ester

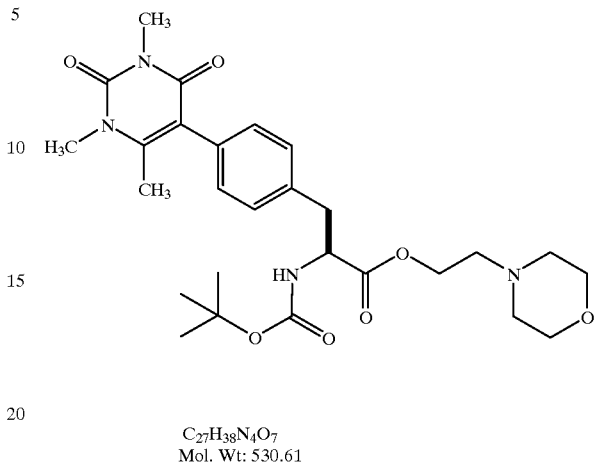

$C_{27}H_{38}N_4O_7$
Mol. Wt: 530.61

To a solution of N-[(1,1-dimethylethoxy)carbonyl]-4-(1,3,6-trimethyl-2,4-dioxo-5-pyrimidinyl)-L-phenylalanine (1.21 mmol, 505 mg) and 2-(4-morpholino)ethanol (2.42 mmol, 318 mg) in THF (8 mL) was added di-isopropylcarbodiimide (DIC) (1.82 mmol, 0.287 mL) and 4-dimethylaminopyridine (0.6 mmol, 74 mg) at room temperature. The resulting solution was stirred for 72 h. Then, the reaction mixture was poured into water (50 mL) and was extracted with ethyl acetate (3×50 mL). The combined extracts were washed with water (2×50 mL) and brine solution (100 mL) and were dried over anhydrous magnesium sulfate. Filtration of the drying agent and concentration of the filtrate gave the crude product which was purified by silica gel chromatography using a Biotage (40m) column to obtain 428 mg (67% yield) of N-[(1,1-dimethylethoxy)carbonyl]-4-(1,3,6-trimethyl-2,4-dioxo-5-pyrimidinyl)-L-phenylalanine 2-(4-morpholino)ethyl ester as an amorphous white solid. ES-HRMS m/e calcd for $C_{27}H_{38}N_4O_7$ (M+Na) 553.2633, found 553.2636.

c) Preparation of 4-(1,3,6-trimethyl-2,4-dioxo-5-pyrimidinyl)-L-phenylalanine 2-(4-morpholino)ethyl ester hydrochloride salt

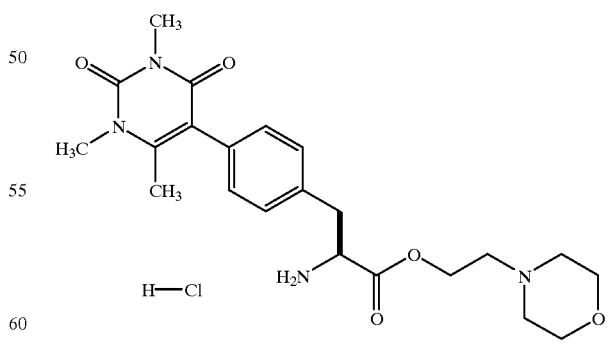

$C_{22}H_{31}ClN_4O_5$
Mol. Wt: 466.96

The solid N-[(1,1-dimethylethoxy)carbonyl]-4-(1,3,6-trimethyl-2,4-dioxo-5-pyrimidinyl)-L-phenylalanine 2(4-morpholino)ethyl ester (1.6 mmol, 0.85 g) was treated with 4N hydrochloric acid in dioxane (16.02 mmol, 4 mL) at room temperature and the solution was stirred for 3 h as a white precipitate formed. The solids were diluted with diethyl ether, the mother liquor was decanted and the residue was dried first on the rotary evaporator and then under high vacuum to afford 0.75 g (99% yield) of 4-(1,3,6-trimethyl-2,4-dioxo-5-pyrimidinyl)-L-phenylalanine 2-(4-morpholino)ethyl ester hydrochloride salt as an amorphous yellow solid. ES-HRMS m/e calcd for $C_{22}H_{30}N_4O_5$ (M+H) 431.2289, found 431.2292.

d) Preparation of N-[(2,6-dichlorophenyl)carbonyl]-4-(1,3,6-trimethyl-2,4-dioxo-5-pyrimidinyl)-L-phenylalanine 2-(4-morpholino)ethyl ester

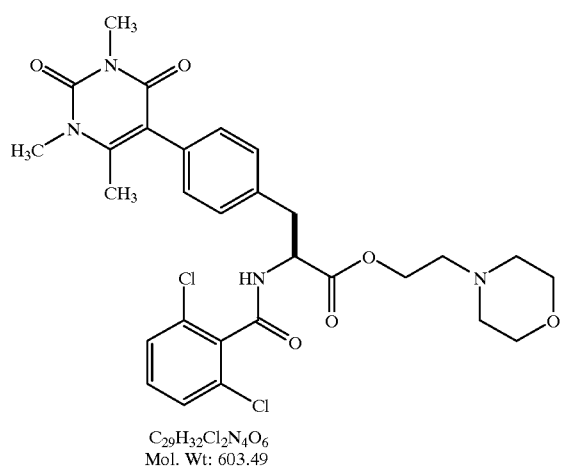

$C_{29}H_{32}Cl_2N_4O_6$
Mol. Wt: 603.49

To a suspension of 4-(1,3,6-trimethyl-2,4-dioxo-5-pyrimidinyl)-L-phenylalanine 2-(4-morpholino)ethyl ester hydrochloride salt (0.85 mmol, 399 mg) and 2,6-dichlorobenzoyl chloride (0.95 mmol, 0.201 g) in dichloromethane (4 mL) was added diisopropylethylamine (4.75 mmol, 0.66 mL) at room temperature. After 5 min, everything went into solution and the clear yellow solution was stirred for 48 h at room temperature. The resulting light brown solution was diluted with dichloromethane (50 mL). The dichloromethane layer was washed successively with 1N hydrochloric acid (2×50 mL), saturated sodium bicarbonate solution (50 mL), and brine solution (50 mL) and was dried over anhydrous magnesium sulfate. Filtration of the drying agent and concentration gave the crude product which was purified by silica gel chromatography using a Biotage (40m) column to afford 0.427 g (75% yield) of N-[(2,6-dichlorophenyl)carbonyl]-4-(1,3,6-trimethyl-2,4-dioxo-5-pyrimidinyl)-L-phenylalanine 2-(4-morpholino)ethyl ester as a white solid: mp 90–94° C. ES-HRMS m/e calcd for $C_{29}H_{32}Cl_2N_4O_6$ (M+H) 603.1772, found 603.1782.

Example 32

Preparation of N-[(2-chloro-6-methylphenyl)carbonyl]-4-(1,3,6-trimethyl-2,4-dioxo-5-pyrimidinyl)-L-phenylalanine 2-(4-morpholino)ethyl ester

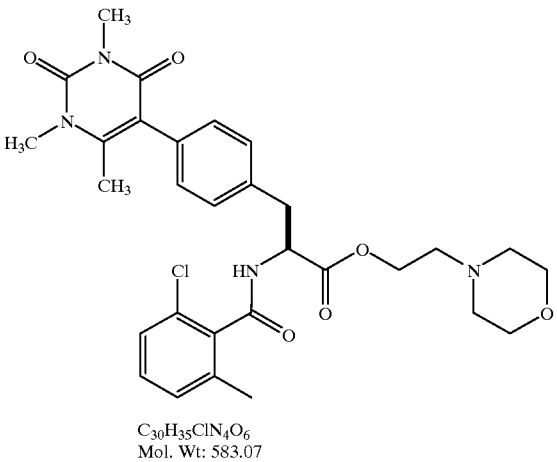

$C_{30}H_{35}ClN_4O_6$
Mol. Wt: 583.07

N-[(2-chloro-6-methylphenyl)carbonyl]-4-(1,3,6-trimethyl-2,4-dioxo-5-pyrimnidinyl)-L-phenylalanine 2-(4-morpholino)ethyl ester was prepared from 4-(1,3,6-trimethyl-2,4-dioxo-5-pyrimidinyl)-L-phenylalanine 2-(4-morpholino)ethyl ester and 2-chloro-6-methylbenzoyl chloride using the general procedures described in example 31 and was obtained as an amorphous white solid. ES-HRMS m/e calcd for $C_{30}H_{35}ClN_4O_6$ (M+H) 583.2318, found 583.2326.

Example 33

Preparation of N-[(2,6-dichlorophenyl)carbonyl]-4-(1,3,6-trimethyl-2,4-dioxo-5-pyrimidinyl)-L-phenylalanine 1-(acetoxy)ethyl ester a) Preparation of N-[(1,1-dimethylethoxy)carbonyl]-4-(1,3,6-trimethyl-2,4-dioxo-5-pyrimidinyl)-L-phenylalanine 1-(acetoxy)ethyl ester

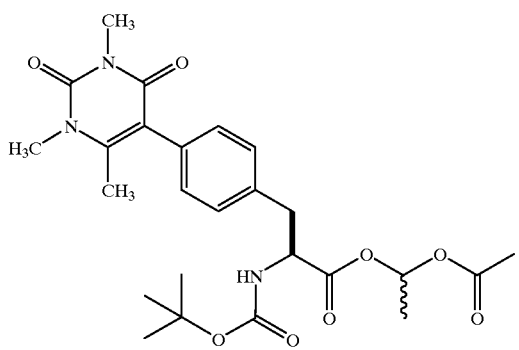

$C_{25}H_{33}N_3O_8$
Mol. Wt: 503.56

To a suspension of N-[(1,1-dimethylethoxy)carbonyl]-4-(1,3,6-trimethyl-2,4-dioxo-5-pyrimidinyl)-L-phenylalanine (1.006 mmol, 420 mg) and sodium bicarbonate (5.03 mmol, 422 mg) in DMF (8 mL) was added 1-chloroethyl acetate (5.03 mmol, 616 mg) at room temperature. The reaction mixture was stirred for 48 h. Then, it was poured into water (50 mL) and was extracted with ethyl acetate (3×50 mL). The combined extracts were washed with water (2×50 mL) and brine solution (100 mL) and were dried over anhydrous magnesium sulfate. Filtration of the drying agent and concentration of the filtrate gave the crude product which was purified by silica gel chromatography using a Biotage (40s) column to obtain 390 mg (77% yield) of N-[(1,1-dimethylethoxy)carbonyl]-4-(1,3,6-trimethyl-2,4-dioxo-5-pyrimidinyl)-L-phenylalanine 1-(acetoxy)ethyl ester as an amorphous white solid. ES-HRMS m/e calcd for $C_{25}H_{33}N_3O_8$ (M+Na) 526.2160, found 526.2143.

b) Preparation of 4-(1,3,6-trimethyl-2,4-dioxo-5-pyrimidinyl)-L-phenylalanine 1-(acetoxy)ethyl ester hydrochloride salt

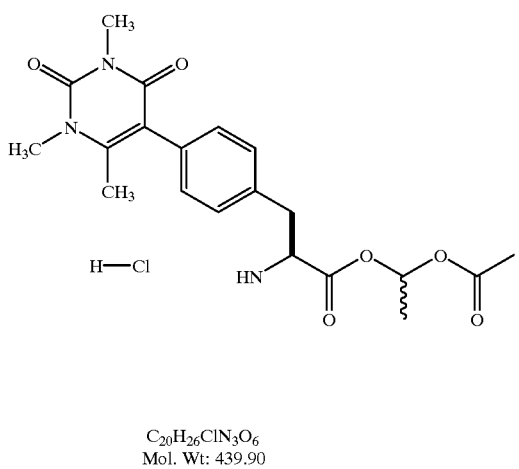

$C_{20}H_{26}ClN_3O_6$
Mol. Wt: 439.90

The solid N-[(1,1-dimethylethoxy)carbonyl]-4-(1,3,6-trimethyl-2,4-dioxo-5-pyrimidinyl)-L-phenylalanine 1-(acetoxy)ethyl ester (1.4 mmol, 0.705 g) was treated with 4N hydrochloric acid in dioxane (20 mmol, 5 mL) at room temperature and the solution was stirred for 2 h as a white precipitate was formed. The mixture was diluted with diethyl ether and dichloromethane and the solids were collected by filtration washing with diethyl ether. After air drying, 0.63 g (99% yield) of 4-(1,3,6-trimethyl-2,4-dioxo-5-pyrimidinyl)-L-phenylalanine 1-(acetoxy)ethyl ester hydrochloride was obtained as an amorphous gray solid. ES-HRMS m/e calcd for $C_{20}H_{26}N_3O_6$ (M+H) 404.1816, found 404.1818.

c) Preparation of N-[(2,6-dichlorophenyl)carbonyl]-4-(1,3,6-trimethyl-2,4-dioxo-5-pyrimidinyl)-L-phenylalanine 1-(acetoxy)ethyl ester

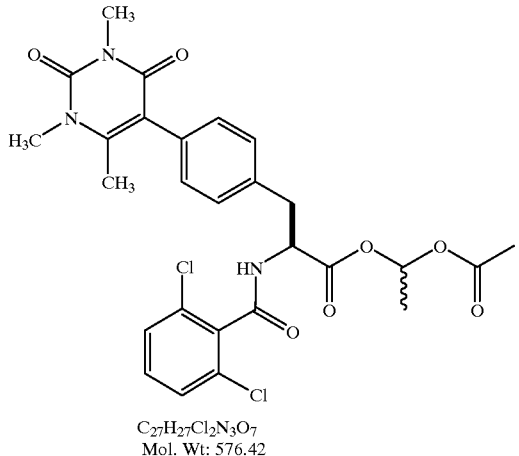

$C_{27}H_{27}Cl_2N_3O_7$
Mol. Wt: 576.42

To a suspension of 4-(1,3,6-trimethyl-2,4-dioxo-5-pyrimidinyl)-L-phenylalanine 1-(acetoxy)ethyl ester hydrochloride salt (0.723 mmol, 399 mg) and 2,6-dichlorobenzoyl chloride (0.8 mmol, 0.17 g) in dichloromethane (5 mL) was added diisopropylethylamine (3.2 mmol, 0.45 mL) at room temperature. After 5 min, everything went into solution and the clear yellow solution was stirred for 48 h at room temperature. The resulting light brown solution was diluted with dichloromethane (50 mL). The dichloromethane layer was washed successively with 1N hydrochloric acid (2×50 mL), saturated sodium bicarbonate solution (50 mL), and brine solution (50 mL) and was dried over anhydrous magnesium sulfate. Filtration of the drying agent and concentration of the solvent gave the crude product, which was purified by silica gel chromatography using a Biotage (40s) column to afford 0.312 g (67% yield) of N-[(2,6-dichlorophenyl)carbonyl]-4-( 1,3,6-trimethyl-2,4-dioxo-5-pyrimidinyl)-L-phenylalanine 1-(acetoxy)ethyl ester as a white solid: mp 168–170° C. ES-HRMS m/e calcd for $C_{27}H_{27}Cl_2N_3O_7$ (M+Na) 598.1118, found 598.1122.

Example 34
Preparation of N-[(2-chloro-6-methylphenyl)carbonyl]-4-(1,3,6-trimethyl-2,4-dioxo-5-pyrimidinyl)-L-phenylalanine 1-(acetoxy)ethyl ester

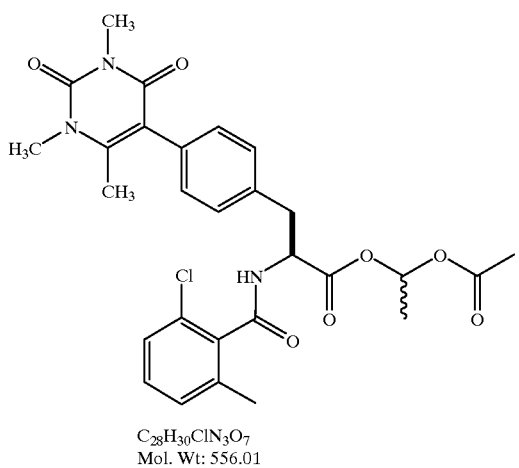

$C_{28}H_{30}ClN_3O_7$
Mol. Wt: 556.01

N-[(2-chloro-6-methylphenyl)carbonyl]-4-(1,3,6-trimethyl-2,4-dioxo-5-pyrimidinyl)-L-phenylalanine 1-(acetoxy)ethyl ester was prepared from 4-(1,3,6-trimethyl-2,4-dioxo-5-pyrimidinyl)-L-phenylalanine 1-(acetoxy)ethyl ester and 2-chloro-6-methylbenzoyl chloride using the general procedures described in example 33 and was obtained as a white solid: mp 84–88° C. ES-HRMS m/e calcd for $C_{28}H_{30}ClN_3O_7$ (M+Na) 578.1664, found 578.1665.

Example 35

Preparation of L-prolyl-4-(1,3,6-trimethyl-2,4-dioxo-5-pyrimidinyl)-L-phenylalanine a) Preparation of L-[(1,1-dimethylethoxy)carbonyl]-prolyl-4-(1,3,6-trimethyl-2,4-dioxo-5-pyrimidinyl)-L-phenylalanine methyl ester

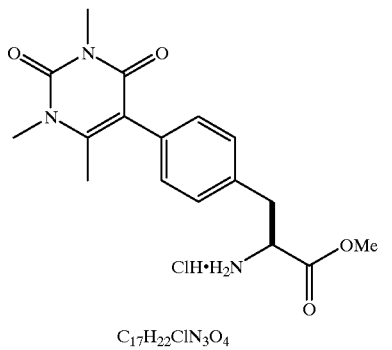

$C_{17}H_{22}ClN_3O_4$
Mol. Wt: 367.87

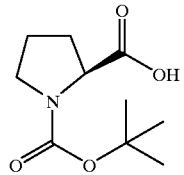

$C_{10}H_{17}NO_4$
Mol. Wt: 215.25

HBTU, DIPEA
DMF, r.t., 48 h

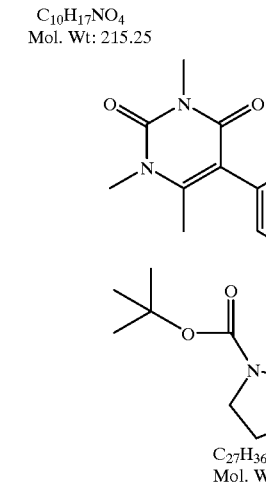

$C_{27}H_{36}N_4O_7$
Mol. Wt: 528.60

To a suspension of 4-(1,3,6-trimethyl-2,4-dioxo-5-pyrimidinyl)-L-phenylalanine methyl ester hydrochloride salt (7 mmol, 2.57 g), HBTU (8.75 mmol, 3.32 g) and L-[(1,1-dimethylethoxy)carbonyl]-proline (8.75 mmol, 1.88 g) in DMF (28 mL) was added diisopropylethylamine (21 mmol, 3.65 mL) at room temperature. After 2 min, everything went into solution and the yellow clear solution was stirred for 48 h at room temperature. The resulting dark-brown solution was diluted with ethyl acetate (100 mL). The ethyl acetate layer was washed successively with 1N hydrochloric acid (2×50 mL), saturated sodium bicarbonate solution (100 mL), and brine solution (100 mL) and was dried over anhydrous magnesium sulfate. Filtration of the drying agent and concentration of the solvent gave the crude product which was purified by silica gel column chromatography using a Biotage (40m) column to afford 2.5 g (67% yield) of L-[(1,1-dimethylethoxy)carbonyl]-prolyl-4-(1,3,6-trimethyl-2,4-dioxo-5-pyrimidinyl)-L-phenylalanine methyl ester as an amorphous white solid. ES-HRMS m/e calcd for $C_{27}H_{36}N_4O_7$ (M+Na) 551.2476, found 551.2476.

b) Preparation of L-[(1,1-dimethylethoxy)carbonyl]-prolyl-4-(1,3,6-trimethyl-2,4-dioxo-5-pyrimidinyl)-L-phenylalanine

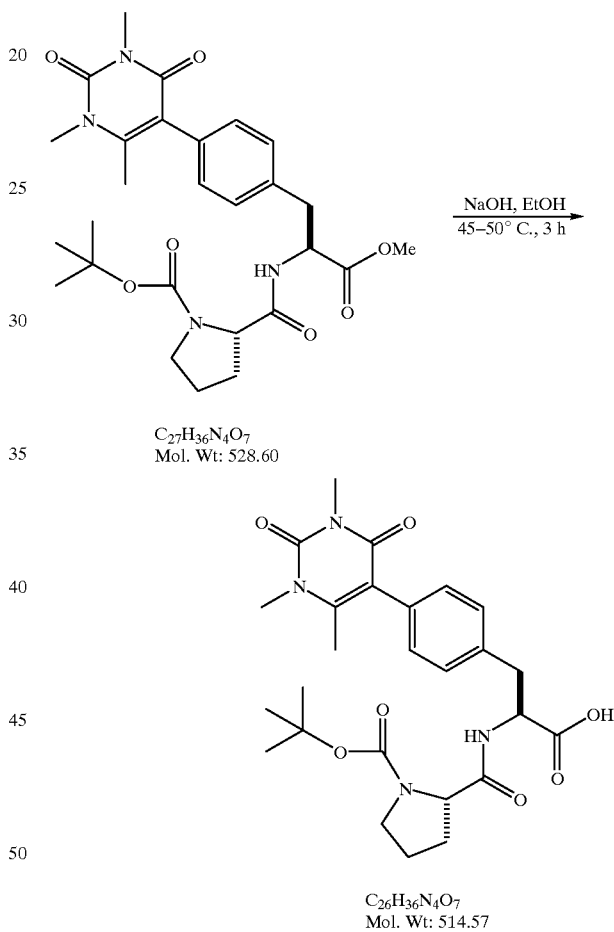

To a suspension of L-[(1,1-dimethylethoxy)carbonyl]-prolyl-4-(1,3,6-trimethyl-2,4-dioxo-5-pyrimidinyl)-L-phenylalanine methyl ester (1.51 mmol, 800 mg) in ethanol (8 mL) was added aqueous 1.0 N sodium hydroxide (5 mL) at room temperature. The mixture was heated to 45–50° C. and the resulting clear solution was stirred for 3 h. The ethanol was removed under reduced pressure and the residue was diluted with water (25 mL). The aqueous solution was washed with diethyl ether (50 mL) to remove any neutral impurities. The aqueous layer was acidified with 1.0 N HCl and the product was extracted into ethyl acetate (2×50 mL).

The combined organic extracts were washed with brine solution (50 mL) and were dried over anhydrous magnesium sulfate. Filtration of the drying agent and concentration of the filtrate afforded 640 mg (83% yield) of L-[(1,1-dimethylethoxy)carbonyl]-prolyl-4-(1,3,6-trimethyl-2,4-dioxo-5-pyrimidinyl)-L-phenylalanine as an amorphous white solid. ES-HRMS m/e calcd for $C_{26}H_{34}N_4O_7$ (M+Na) 537.2320, found 537.2321.

c) Preparation of L-prolyl-4-(1,3,6-trimethyl-2,4-dioxo-5-pyrimidinyl)-L-phenylalanine

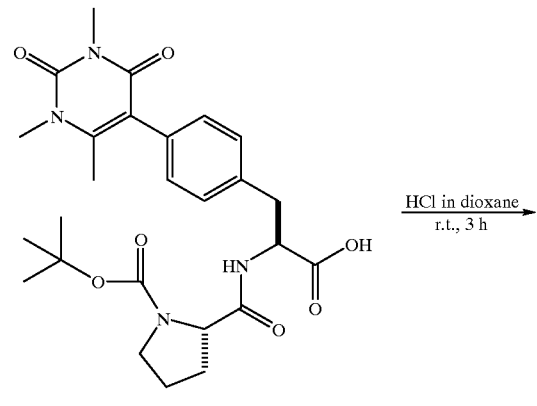

The solid L-[(1,1-dimethylethoxy)carbonyl]-prolyl-4-(1,3,6-trimethyl-2,4-dioxo-5-pyrimidinyl)-L-phenylalanine (0.89 mmol, 462 mg) was treated with 4N hydrochloric acid in dioxane (16 mmol, 4 mL) at room temperature and the solution was stirred for 3 h. Then, the solvent was removed under vacuum and the residue was dried under high vacuum to afford a crude residue which was triturated with dichloromethane, diethyl ether and acetonitrile to obtain 395 mg (99% yield) of L-prolyl-4-(1,3,6-trimethyl-2,4-dioxo-5-pyrimidinyl)-L-phenylalanine hydrochloride salt as an amorphous light yellow solid. ES-HRMS m/e calcd for $C_{21}H_{26}N_4O_5$ (M+H) 415.1976, found 415.1976.

Example 36

N-[(2,6-difluorophenyl)carbonyl]-4-(1,3,6-trimethyl-2,4-dioxo-5-pyrimidinyl)-L-phenylalanine ethyl ester

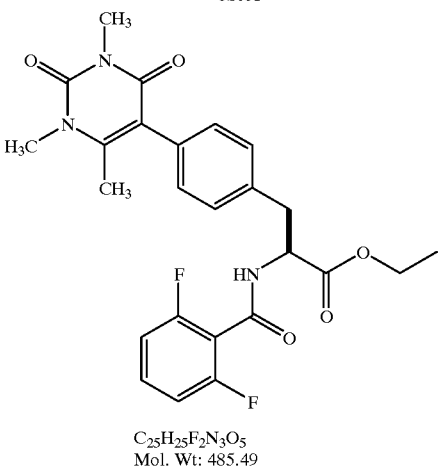

To a suspension of N-[(2,6-difluorophenyl)carbonyl]-4-(1,3,6-trimethyl-2,4-dioxo-5-pyrimidinyl)-L-phenylalanine (0.743 mmol, 340 mg) and sodium bicarbonate (5.94 mmol, 499 mg) in DMF (3.8 mL) was added iodoethane (5.94 mmol, 0.475 mL) at room temperature. The mixture was stirred for 48 h at room temperature. Then, the reaction mixture was poured into water (100 mL) and was extracted with ethyl acetate (3×25 mL). The combined extracts were washed with brine solution (80 mL) and were dried over anhydrous sodium sulfate. Filtration of the drying agent and concentration of the filtrate gave the crude product which was purified by silica gel chromatography using a Biotage (40s) column to obtain 335 mg (93% yield) of N-[(2,6-difluorophenyl)carbonyl]-4-(1,3,6-trimethyl-2,4-dioxo-5-pyrimidinyl)-L-phenylalanine ethyl ester as a crystalline white solid: mp 218–219° C. ES-HRMS m/e calcd for $C_{25}H_{25}F_2N_3O_5$ (M+Na) 508.1654, found 508.1660.

Example 37

Preparation of N-[(2,6-difluorophenyl)carbonyl]-4-(1,3,6-trimethyl-2,4-dioxo-5-pyrimidinyl)-L-phenylalanine 2-[(N,N-diethyl)amino]ethyl ester

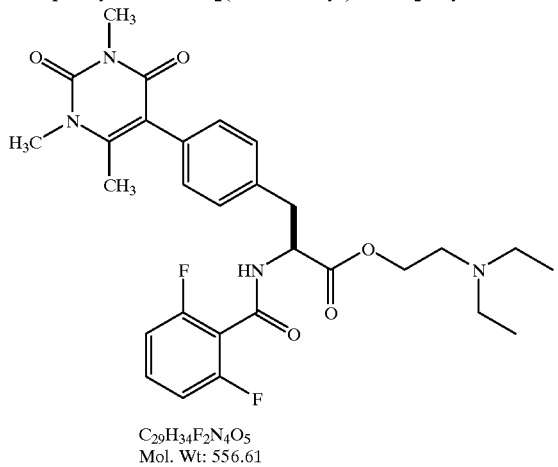

A mixture of N-[(2,6-difluorophenyl)carbonyl]-4-(1,3,6-trimethyl-2,4-dioxo-5-pyrimidinyl)-L-phenylaianine (1.0 mmol, 460 mg), 2-[(N,N-diethyl)aminolethyl chloride hydrochloride (8.05 mmol, 1.43 g) and potassium carbonate (8.05 mmol, 1.11 g) in ethyl acetate (5 mL) and water (5 mL) was stirred at room termperature overnight. The layers were separated and the aqueous layer was extracted with ethyl acetate (2×40 mL). The combined extracts were washed with brine (50 mL) and dried over anhydrous sodium sulfate. Filtration of the drying agent and concentration of the filtrate gave the crude product which was purified by silica gel chromatography using a Biotage (40m) column to obtain 426 mg (76% yield) of N-[(2,6-difluorophenyl)carbonyl]-4-(1,3,6-trimethyl-2,4-dioxo-5-pyrimidinyl)-L-phenylalanine 2-[(N,N-diethyl)amino]ethyl ester as an amorphous white solid. ES-HRMS m/e calcd for $C_{29}H_{34}F_2N_4O_5$ (M+H) 557.2570, found 557.2575.

Example 38

N-[(2,6-difluorophenyl)carbonyl]-4-(1,3,6-trimethyl-2,4-dioxo-5-pyrimidinyl)-L-phenylalanine 1-(acetoxy)ethyl ester

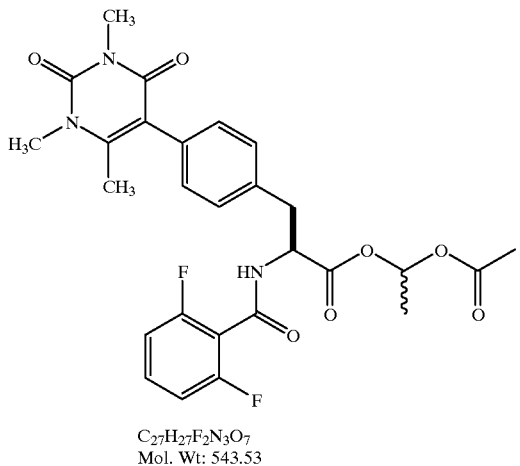

$C_{27}H_{27}F_2N_3O_7$
Mol. Wt: 543.53

To a suspension of N-[(2,6-difluorophenyl)carbonyl]-4-(1,3,6-trimethyl-2,4-dioxo-5-pyrimidinyl)-L-phenylalanine (0.743 mmol, 340 mg) and sodium bicarbonate (5.94 mmol, 499 mg) in DMF (3.0 mL) was added 1-chloroethyl acetate (5.94 mmol, 0.73 g) at room temperature. The mixture was stirred for 48 h at room temperature. Then, the reaction mixture was poured into water (50 mL) and was extracted with ethyl acetate (3×25 mL). The combined extracts were washed with brine solution (80 mL) and were dried over anhydrous sodium sulfate. Filtration of the drying agent and concentration of the filtrate gave the crude product which was purified by silica gel chromatography using a Biotage (40m) column to obtain 265 mg (66% yield) of N-[(2,6-difluorophenyl)carbonyl]-4-(1,3,6-trimethyl-2,4-dioxo-5-pyrimidinyl)-L-phenylalanine 1-(acetoxy)ethyl ester as an amorphous white solid. ES-HRMS m/e calcd for $C_{27}H_{27}F_2N_3O_7$ (M+Na) 566.1709, found 566.1710.

BIOASSAY EXAMPLES

Example A
VLA-4/VCAM-1 Screening Assay

VLA-4 antagonist activity, defined as ability to compete for binding to immobilized VCAM-1, was quantitated using a solid-phase, dual antibody ELISA. VLA-4 (α4β1 integrin) bound to VCAM-1 was detected by a complex of anti-integrin β1 antibody: HRP-conjugated anti-mouse IgG: chromogenic substrate (K-Blue). Initially, this entailed coating 96 well plates (Nunc Maxisorp) with recombinant human VCAM-1 (0.4 μg in 100 μl PBS), sealing each plate and then allowing the plates to stand at 4° C. for ~18 hr. The VCAM-coated plates were subsequently blocked with 250 μl of 1% BSA/0.02% NaN₃ to reduce non-specific binding. On the day of assay, all plates were washed twice with VCAM Assay Buffer (200 μl/well of 50 mM Tris-HCl, 100 mM NaCl, 1 mM $MnCl_2$, 0.05% Tween 20; pH 7.4). Test compounds were dissolved in 100% DMSO and then diluted 1:20 in VCAM Assay Buffer supplemented with 1 mg/mL BSA (i.e., final DMSO=5%). A series of 1:4 dilutions were performed to achieve a concentration range of 0.005 nM–1.563 μM for each test compound. 100 μl per well of each dilution was added to the VCAM-coated plates, followed by 10 μl of Ramos cell-derived VLA-4. These plates were sequentially mixed on a platform shaker for 1 min, incubated for 2 hr at 37° C., and then washed four times with 200 μl/well VCAM Assay Buffer. 100 μl of mouse anti-human integrin β1 antibody was added to each well (0.6 μg/mL in VCAM Assay Buffer+1 mg/mL BSA) and allowed to incubate for 1 hr at 37° C. At the conclusion of this incubation period, all plates were washed four times with VCAM Assay Buffer (200 μl/well). A corresponding second antibody, HRP-conjugated goat anti-mouse IgG (100 μl per well @ 1:800 dilution in VCAM Assay Buffer+1 mg/mL BSA), was then added to each well, followed by a 1 hr incubation at room temperature and concluded by three washes (200 μl/well) with VCAM Assay Buffer. Color development was initiated by addition of 100 μl K-Blue per well (15 min incubation, room temp) and terminated by addition of 100 μl Red Stop Buffer per well. All plates were then read in a UV/Vis spectrophotometer at 650 nM. Results were calculated as % inhibition of total binding (i.e., VLA-4+VCAM-1 in the absence of test compound). The results are provided in the following Table I (A=$IC_{50}$<1 nM, B=$IC_{50}$<10 nM):

TABLE I

| Compound of Example | Activity in VCAM/VLA-4 ELISA Assay |
|---|---|
| 2 | A |
| 3 | B |
| 4 | A |
| 5 | A |

Example B
Ramos (VLA-4)/VCAM-1 Cell-Based Screening Assay Protocol

MATERIALS

Soluble recombinant human VCAM-1 (mixture of 5- and 7-Ig domain) was purified from CHO cell culture media by inmmunoaffinity chromatography and maintained in a solution containing 0.1 M Tris-glycine (pH 7.5), 0.1 M NaCl, 5 mM EDTA, 1 mM PMSF, 0.02% 0.02% NaN₃ and 10 μg/mL leupeptin. Calcein-AM was purchased from Molecular Probes Inc.

METHODS

VLA-4 (α4β1 integrin) antagonist activity, defined as ability to compete with cell-surface VLA-4 for binding to immobilized VCAM-1, was quantitated using a Ramos-VCAM-1 cell adhesion assay. Ramos cells bearing cell-surface VLA-4, were labeled with a fluorescent dye (Calcein-AM) and allowed to bind VCAM-1 in the presence or absence of test compounds. A reduction in fluorescence intensity associated with adherent cells (% inhibition) reflected competitive inhibition of VLA-4 mediated cell adhesion by the test compound.

Initially, this entailed coating 96 well plates (Nunc Maxisorp) with recombinant human VCAM-1 (100 ng in 100 µl PBS), sealing each plate and allowing the plates to stand at 4° C. for ≈18 hr. The VCAM-coated plates were subsequently washed twice with 0.05% Tween-20 in PBS, and then blocked for 1 hr (room temperature) with 200 µl of Blocking Buffer (1% BSA/0.02% thimerosal) to reduce non-specific binding. Following the incubation with Blocking Buffer, plates were inverted, blotted and the remaining buffer aspirated. Each plate was then washed with 300 µl PBS, inverted and the remaining PBS aspirated.

Test compounds were dissolved in 100% DMSO and then diluted 1:25 in VCAM Cell Adhesion Assay Buffer (4 mM $CaCl_2$, 4 mM $MgCl_2$ in 50 mM TRIS-HCl, pH 7.5) (final DMSO=4%). A series of eight 1:4 dilutions were performed for each compound (general concentration range of 1 nM–12,500 nM). 100 µl/well of each dilution was added to the VCAM-coated plates, followed by 100 µl of Ramos cells (200,000 cells/well in 1% BSA/PBS). Plates containing test compounds and Ramos cells were allowed to incubate for 45 min at room temperature, after which 165 µl/well PBS was added. Plates were inverted to remove non-adherent cells, blotted and 300 µl/well PBS added. Plates were again inverted, blotted and the remaining buffer gently aspirated. 100 µl Lysis Buffer (0.1% SDS in 50 mM TRIS-HCl, pH 8.5) was added to each well and agitated for 2 min on a rotary shaking platform. The plates were then read for fluorescence intensity on a Cytofluor 2300 (Millipore) fluorecence measurement system (excitation=485 nm, emission=530 nm). The results are shown in the following Table II, where (A=$IC_{50}$<100 nM, B=$IC_{50}$<10000 nM):

TABLE II

| Compound of Example | Activity in VCAM/VLA-4 Ramos Cell Assay |
|---|---|
| 2 | A |
| 3 | A |
| 4 | A |
| 5 | B |
| 6 | A |
| 7 | A |
| 8 | A |
| 9 | A |
| 10 | A |
| 11 | A |
| 12 | A |
| 13 | A |
| 14 | B |
| 15 | A |
| 16 | A |
| 17 | A |
| 18 | A |
| 19 | A |
| 20 | A |
| 21 | A |
| 22 | A |
| 23 | A |
| 24 | B |
| 25 | A |
| 26 | B |
| 27 | B |
| 28 | A |
| 29 | A |
| 30 | B |

TABLE II-continued

| Compound of Example | Activity in VCAM/VLA-4 Ramos Cell Assay |
|---|---|
| 31 | B |
| 32 | B |
| 33 | B |
| 34 | B |
| 35 | A |

Example C

Alpha4-Beta7 Assay Protocol

Two weeks to one day prior to the assay, Nunc high-binding F96 Maxisorp immuno plates, #442404 or #439454, were coated with 25 ng/well (0.25 µg/ml) MadCAM in a volume of 100 µl/well. The plates were covered with sealer and wrapped in saran wrap followed by incubation in the refrigerator for at least 24 hours. The coating buffer employed was: 10 mM carbonate/bicarbonate buffer made up from: 0.8 g/L sodium carbonate and 1.55 g/L sodium bicarbonate adjusted to pH 9.6 with 1 N HCl. Assay buffers consisted of the following:

Wash Buffer: 0.05% Tween 20 in PBS
Blocking Buffer: 1% Nonfat Dry Milk in PBS
Labeling Buffer: PBS
Cell Buffer: RPMI 1640 medium (no additives)
Binding Buffer: 1.5 mM $CaCl_2$
   0.5 mM $MnCl_2$
   50 mM TRIS-HCl; add NaOH dropwise to pH 7.5
     Bring to volume in $H_2O$
     Adjust to pH 7.5
   Dilution Buffer: 4% DMSO in Binding Buffer Plates were washed 2× with wash buffer and then blocked at room temperature for at least 1 hour with Blocking Buffer. Sealed plates were sometimes blocked overnight in the refrigerator. Plates were then washed with PBS and hand blotted dry. Remaining liquid was aspirated from the wells.

Sufficient RPMI 8866 cells were removed from stock for assay ($2 \times 10^6$ cells/ml×10 ml/plate×number of plates) and placed in a centrifuge tube. The tubes were filled to volume with PBS and were spun at 200×G for 8 minutes. The buffer was poured off and the cells were resuspended to $10 \times 10^6$/ml in PBS and a stock solution of calcein in DMSO (5mg/mL) was added at 51 µl/ml of cell suspension. The suspension was incubated for 30 minutes at 37° C. in dark. The cells were then washed with PBS. The PBS was poured off and the cells resuspended in cell buffer at a concentration of $2 \times 10^6$ cells/mL for plating in the assay.

Stock solution of test compounds at 25× first dilution desired in 100% DMSO were prepared. First dilutions for the standard, as well as test compounds, were 1:25 into straight Binding Buffer, while the remaining serial dilutions were into Dilution Buffer (Binding Buffer/4% DMSO). Stock concentrations and dilutions of compounds for screening were determined by anticipated activity.

For the assay, 129 µl Binding Buffer was plated into first row of wells and 100 µl Dilution Buffer was plated into remaining wells. A 5.44 µl aliquot of each compound was pipetted into appropriate, labeled wells, in triplicate. The compounds were next diluted down the plate (34 µl+100 µl=>4-fold dilution). For controls, 100 µl of Dilution Buffer 100 µl Cell Buffer were plated into the nonspecific background wells (no cells, no compound) and 100 µl Dilution Buffer+100 µl cells were plated into the total binding wells (no compound=100% binding). Labeled cells at $2 \times 10^6$ cells/ ml, 100 μl/well (=2×10⁵ cells/well) were added to each well containing compound. The plates were sealed and incubated in the dark for 45 minutes at room temperature. Following incubation, unbound cells were removed by adding 150 μl PBS/well. The plates were inverted, blotted onto paper towels and washed by gently adding 200 μl PBS to wells and blotting again. Remaining buffer was carefully aspirated from the wells. A final 100 μl PBS was added to each well.

The plates were then read for fluorescence intensity on a Cytofluor 2300 (Millipore) fluorecence measurement system (excitation=485 nm, emission=530 nm). $IC_{50}$s of each compound were determined by linear regression analysis. The results are shown in the following table:

TABLE III

| Compound of Example | Activity in MadCAM/RPMI Cell Assay (A = $IC_{50}$ <100 nM, B = $IC_{50}$ <10000 nM, C = $IC_{50}$ <5,000 nM) |
|---|---|
| 6 | A |
| 7 | A |
| 8 | A |
| 9 | A |
| 10 | B |
| 11 | C |
| 12 | A |
| 13 | B |
| 14 | C |
| 15 | B |
| 16 | B |
| 17 | B |
| 18 | A |
| 19 | B |
| 20 | B |
| 21 | B |
| 22 | B |
| 23 | B |
| 24 | B |
| 25 | B |
| 26 | B |
| 27 | B |

What is claimed is:

1. A compound of the formula I:

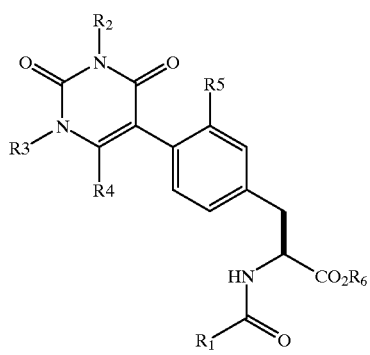

wherein
$R_1$ is a group of the formula Y-1

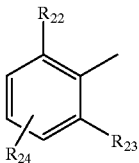

Y-1 wherein
$R_{22}$ and $R_{23}$ are independently hydrogen, lower alkyl, lower alkoxy, cycloalkyl, aryl, arylalkyl, nitro, cyano, lower alkylthio, lower alkylsulfinyl, lower alkyl sulfonyl, lower alkanoyl, halogen, or perfluorolower alkyl and at least one of $R_{22}$ and $R_{23}$ is other than hydrogen; and $R_{24}$ is hydrogen, lower alkyl, lower alkoxy, aryl, nitro, cyano, lower alkyl sulfonyl, or halogen; or $R_1$ is a group of the formula Y-2, which is a five or six membered heteroaromatic ring bonded via a carbon atom to the amide carbonyl wherein said ring contains one, two or three heteroatoms selected from the group consisting of N, O and S and one or two atoms of said ring are independently substituted by lower alkyl, cycloalkyl, halogen, cyano, perfluoroalkyl, or aryl and at least one of said substituted atoms is adjacent to the carbon atom bonded to the amide carbonyl; or $R_1$ is a group of formula Y-3 which is a 3–7 membered ring of the formula:

Y-3 wherein
$R_{25}$ is lower alkyl, unsubstituted or fluorine substituted lower alkenyl, or a group of formula $R_{26}$—$(CH_2)_e$—, $R_{26}$ is aryl, heteroaryl, azido, cyano, hydroxy, lower alkoxy, lower alkoxycarbonyl, lower alkanoyl, lower alkylthio, lower alkyl sulfonyl, lower alkyl sulfinyl, perfluoro lower alkanoyl, nitro, or $R_{26}$ is a group of formula —$NR_{28}R_{29}$, wherein $R_{28}$ is hydrogen or lower alkyl, $R_{29}$ is hydrogen, lower alkyl, lower alkoxycarbonyl, lower alkanoyl, aroyl, perfluoro lower alkanoylamino, lower alkyl sulfonyl, lower alkylaminocarbonyl, arylaminocarbonyl; or $R_{28}$ and $R_{29}$, taken together with the attached nitrogen atom, form a 4, 5 or 6-membered saturated heterocyclic ring optionally containing one additional heteroatom selected from O, S, and N—$R_{40}$,
Q is —$(CH_2)_fO$—, —$(CH_2)_fS$—, —$(CH_2)_fN(R_{27})$—, —$(CH_2)_f$—,
$R_{27}$ is H, lower alkyl, aryl, lower alkanoyl, aroyl or lower alkoxycarbonyl,
$R_{40}$ is H, lower alkyl, aryl, lower alkanoyl, aroyl or lower alkoxycarbonyl the carbon atoms in the ring are unsubstituted or substituted by lower alkyl or halogen,
e is an integer from 0 to 4, and
f is an integer from 0 to 3;
$R_2$ is hydrogen, lower alkyl, substituted lower alkyl, arylalkyl, or aryl;

R$_3$ is hydrogen, lower alkyl, substituted lower alkyl, arylalkyl, or aryl;

R$_4$ is hydrogen, lower alkyl, perfluoro lower alkyl, or aryl;

R$_5$ is hydrogen, lower alkyl, chloro, or lower alkoxy;

R$_6$ is hydrogen, lower alkyl, lower alkyl carbonyloxy lower alkyl, substituted lower alkyl, or R$_6$ is a group of formula P-3:

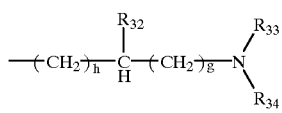

P-3 wherein

R$_{32}$ is hydrogen or lower alkyl; R$_{33}$ is hydrogen, lower alkyl, aryl;

R$_{34}$ is hydrogen or lower alkyl; h is an integer from 0 to 2; g is an integer from 0 to 2; the sum of h and g is 1 to 3; or or R$_6$ is a group of formula P-4:

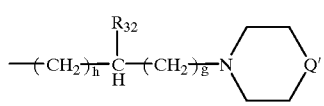

P-4 wherein

R$_{32}$, g, and h are as previously defined; Q' is O, S, —(CH$_2$)$_j$—, or a group of the formula N—R$_{35}$; wherein R$_{35}$ is hydrogen, lower alkyl, lower alkanoyl, lower alkoxycarbonyl; j is 0, 1 or 2; or its pharmaceutically acceptable salts.

2. A compound of claim 1 of the formula I:

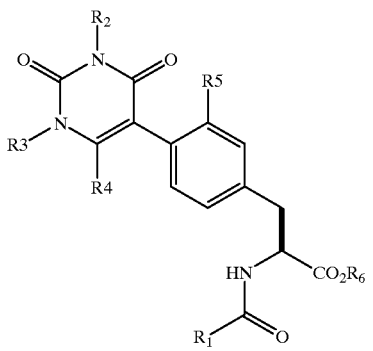

wherein

R$_1$ is a group of the formula Y-1

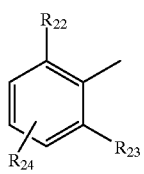

Y-1 wherein

R$_{22}$ and R$_{23}$ are independently hydrogen, lower alkyl, lower alkoxy, cycloalkyl, aryl, arylalkyl, nitro, cyano, lower alkylthio, lower alkylsulfinyl, lower alkyl sulfonyl, lower alkanoyl, halogen, or perfluorolower alkyl and at least one of R$_{22}$ and R$_{23}$ is other than hydrogen; and R$_{24}$ is hydrogen, lower alkyl, lower alkoxy, aryl, nitro, cyano, lower alkyl sulfonyl, or halogen; or R$_1$ is a group of the formula Y-2, which is a five or six membered heteroaromatic ring bonded via a carbon atom to the amide carbonyl wherein said ring contains one, two or three heteroatoms selected from the group consisting of N, O and S and one or two atoms of said ring are independently substituted by lower alkyl, cycloalkyl, halogen, cyano, perfluoroalkyl, or aryl and at least one of said substituted atoms is adjacent to the carbon atom bonded to the amide carbonyl; or R$_1$ is a group of formula Y-3 which is a 3–7 membered ring of the formula:

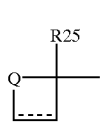

Y-3 wherein

R$_{25}$ is lower alkyl, unsubstituted or fluorine substituted lower alkenyl, or a group of formula R$_{26}$—(CH$_2$)$_e$—, R$_{26}$ is aryl, heteroaryl, azido, cyano, hydroxy, lower alkoxy, lower alkoxycarbonyl, lower alkanoyl, lower alkylthio, lower alkyl sulfonyl, lower alkyl sulfinyl, perfluoro lower alkanoyl, nitro, or R$_{26}$ is a group of formula —NR$_{28}$R$_{29}$, wherein R$_{28}$ is hydrogen or lower alkyl, R$_{29}$ is hydrogen, lower alkyl, lower alkoxycarbonyl, lower alkanoyl, aroyl, perfluoro lower alkanoylamino, lower alkyl sulfonyl, lower alkylaminocarbonyl, arylaminocarbonyl; or R$_{28}$ and R$_{29}$, taken together with the attached nitrogen atom, form a 4, 5 or 6-membered saturated heterocyclic ring optionally containing one additional heteroatom selected from O, S, and N—R$_{40}$, Q is —(CH$_2$)$_f$O—, —(CH$_2$)$_f$S—, —(CH$_2$)$_f$N(R$_{27}$)—, —(CH$_2$)$_f$—, R$_{27}$ is H, lower alkyl, aryl, lower alkanoyl, aroyl or lower alkoxycarbonyl, R$_{40}$ is H, lower alkyl, aryl, lower alkanoyl, aroyl or lower alkoxycarbonyl the carbon atoms in the ring are unsubstituted or substituted by lower alkyl or halogen, e is an integer from 0 to 4, and f is an integer from 0 to 3;

R$_2$ is hydrogen, lower alkyl, substituted lower alkyl or aryl;

R$_3$ is hydrogen, lower alkyl, substituted lower alkyl, or aryl;

R$_4$ is hydrogen, lower alkyl, perfluoro lower alkyl, or aryl;

R$_5$ is hydrogen, lower alkyl, chloro, or lower alkoxy;

R$_6$ is hydrogen, lower alkyl, lower alkyl carbonyloxy lower alkyl, substituted lower alkyl, or $R_6$ is a group of formula P-3:

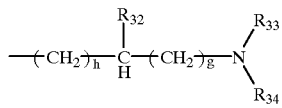

wherein $R_{32}$ is hydrogen or lower alkyl; $R_{33}$ is hydrogen, lower alkyl, aryl; $R_{34}$ is hydrogen or lower alkyl; h is an integer from 0 to 2; g is an integer from 0 to 2; the sum of h and g is 1 to 3; or or $R_6$ is a group of formula P-4:

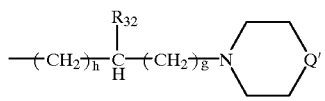

wherein $R_{32}$, g, and h are as previously defined; Q' is O, S, $—(CH_2)_j—$, or a group of the formula $N—R_{35}$; wherein $R_{35}$ is hydrogen, lower alkyl, lower alkanoyl, lower alkoxycarbonyl; j is 0, 1 or 2; or its pharmaceutically acceptable salts.

3. A compound of claim 2, wherein $R_4$ is hydrogen, lower alkyl, or perfluoro lower alkyl.

4. A compound of claim 2 wherein $R_1$ is a group of the formula Y-1

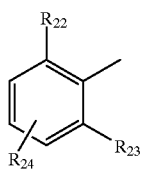

wherein $R_{22}$ and $R_{23}$ are independently lower alkyl or halogen; and $R_{24}$ is hydrogen.

5. A compound of claim 2 wherein $R_1$ is a group of the formula Y-1

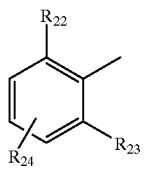

wherein $R_{22}$ and $R_{23}$ are independently hydrogen or halogen; and $R_{24}$ is lower alkoxy.

6. A compound of claim 2 wherein $R_1$ is a group of formula Y-3 which is a 3–7 membered ring of the formula:

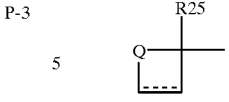

wherein $R_{25}$ is a group of formula $R_{26}—(CH_2)_e—$, wherein $R_{26}$ is lower alkoxy, Q is $—(CH_2)_f—$, e is an integer from 0 to 4, and f is an integer from 0 to 3.

7. A compound of claim 2 of the formula I:

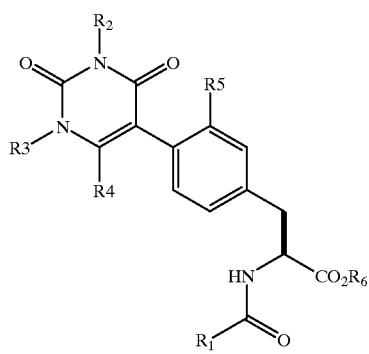

wherein $R_1$ is a group of the formula Y-1

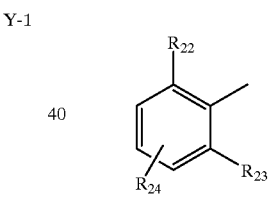

wherein $R_{22}$ and $R_{23}$ are independently hydrogen, lower alkyl, lower alkoxy, cycloalkyl, aryl, arylalkyl, nitro, cyano, lower alkylthio, lower alkylsulfinyl, lower alkyl sulfonyl, lower alkanoyl, halogen, or perfluorolower alkyl and at least one of $R_{22}$ and $R_{23}$ is other than hydrogen; and $R_{24}$ is hydrogen, lower alkyl, lower alkoxy, aryl, nitro, cyano, lower alkyl sulfonyl, or halogen; or $R_1$ is a five or six membered heteroaromatic ring bonded via a carbon atom to the amide carbonyl wherein said ring contains one, two or three heteroatoms selected from the group consisting of N, O and S and one or two atoms of said ring are independently substituted by lower alkyl, cycloalkyl, halogen, cyano, perfluoroalkyl, or aryl and at least one of said substituted atoms is adjacent to the carbon atom bonded to the amide carbonyl; or $R_1$ is a group of formula Y-3 which is a 3–7 membered ring of the formula:

Y-3

wherein

R$_{25}$ is lower alkyl, unsubstituted or fluorine substituted lower alkenyl, or a group of formula R$_2$—(CH$_2$)$_e$—, R$_{26}$ is aryl, heteroaryl, azido, cyano, hydroxy, lower alkoxy, lower alkoxycarbonyl, lower alkanoyl, lower alkylthio, lower alkyl sulfonyl, lower alkyl sulfinyl, perfluoro lower alkanoyl, nitro, or R$_{26}$ is a group of formula —NR$_{28}$R$_{29}$, wherein R$_{28}$ is hydrogen or lower alkyl, R$_{29}$ is hydrogen, lower alkyl, lower alkoxycarbonyl, lower alkanoyl, aroyl, perfluoro lower alkanoylamino, lower alkyl sulfonyl, lower alkylaminocarbonyl, arylaminocarbonyl; or R$_{28}$ and R$_{29}$, taken together with the attached nitrogen atom, form a 4, 5 or 6-membered saturated heterocyclic ring optionally containing one additional heteroatom selected from O, S, and N—R$_{40}$, Q is —(CH$_2$)$_f$O—, —(CH$_2$)$_f$S—, —(CH$_2$)$_f$N(R$_{27}$)—, —(CH$_2$)$_f$—, R$_{27}$ is H, lower alkyl aryl, lower alkanoyl, aroyl or lower alkoxycarbonyl, R$_{40}$ is H, lower alkyl, aryl, lower alkanoyl, aroyl or lower alkoxycarbonyl the carbon atoms in the ring are unsubstituted or substituted by lower alkyl or halogen, e is an integer from 0 to 4, and f is an integer from 0 to 3;

R$_2$ is lower alkyl;

R$_3$ is lower alkyl;

R$_4$ is hydrogen, perfluoro lower alkyl, or lower alkyl;

R$_5$ is hydrogen or lower alkyl; and

R$_6$ is hydrogen, lower alkyl, lower alkyl carbonyloxy lower alkyl, or R$_6$ is a group of formula P-3:

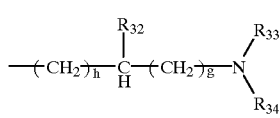

P-3 wherein

R$_{32}$ is hydrogen or lower alkyl; R$_{33}$ is hydrogen, lower alkyl, aryl;

R$_{34}$ is hydrogen or lower alkyl; h is an integer from 0 to 2; g is an integer from 0 to 2; the sum of h and g is 1 to 3; or or R$_6$ is a group of formula P-4:

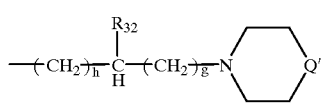

P-4 wherein

R$_{32}$, g, and h are as previously defined; Q' is O, S, —(CH$_2$)$_j$—, or a group of the formula N—R$_{35}$; wherein R$_{35}$s is hydrogen, lower alkyl, lower alkanoyl, lower alkoxycarbonyl; j is 0, 1 or 2.

8. A compound of claim 7 wherein R$_1$ is a group of the formula Y-1

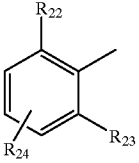

Y-1 wherein

R$_{22}$ and R$_{23}$ are independently perfluoro lower alkyl, lower alkyl, or halogen; and R$_{24}$ is hydrogen.

9. A compound of claim 8 wherein R$^2$ and R$^3$ are lower alkyl; R$^4$ is hydrogen or lower alkyl, and R$_5$ and R$_6$ are hydrogen.

10. A compound of claim 9 which is N-[(2,6-dichlorophenyl)carbonyl]-4-(1,3,6-trimethyl-2,4-dioxo-5-pyrimidinyl)-L-phenylalanine.

11. A compound of claim 9 which is N-[(2-bromo-6-methylphenyl)carbonyl]-4-(1,3,6-trimethyl-2,4-dioxo-5-pyrimidinyl)-L-phenylalanine.

12. A compound of claim 9 which is N-[(2-chloro-6-methylphenyl)carbonyl]-4-(1,3,6-trimethyl-2,4-dioxo-5-pyrimidinyl)-L-phenylalanine.

13. A compound of claim 9 which is N-[(2-ethyl-6-methylphenyl)carbonyl]-4-(1,3,6-timethyl-2,4-dioxo-5-pyrimidinyl)-L-phenylalanine.

14. A compound of claim 9 which is N-[[2-(2-methylethyl)-6-methylphenyl]carbonyl]-4-(1,3,6-trimethyl-2,4-dioxo-5-pyrimidinyl)-L-phenylalanine.

15. A compound of claim 9 which is N-[(2,6-difluorophenyl)carbonyl]-4-(1,3,6-trimethyl-2,4-dioxo-5-pyrimidinyl)-L-phenylalanine.

16. A compound of claim 9 which is N-[[2-fluoro-6-(trifluoromethyl)phenyl]carbonyl]-4-(1,3,6-trimethyl-2,4-dioxo-5-pyrimidinyl)-L-phenylalanine.

17. A compound of claim 9 which is N-[[2,6-di-(2-methylethyl)phenyl]carbonyl]-4-(1,3,6-trimethyl-2,4-dioxo-5-pyrimidinyl)-L-phenylalanine.

18. A compound of claim 9 which is N-[(2-chloro-6-ethylphenyl)carbonyl]-4-(1,3,6-trimethyl-2,4-dioxo-5-pyrimidinyl)-L-phenylalanine.

19. A compound of claim 9 which is N-[(2-chloro-6-propylphenyl)carbonyl]-4-(1,3,6-trimethyl-2,4-dioxo-5-pyrimidinyl)-L-phenylalanine.

20. A compound of claim 9 which is N-[[2-chloro-6-(2-methylethyl)phenyl]carbonyl]-4-(1,3,6-trimethyl-2,4-dioxo-5-pyrimidinyl)-L-phenylalanine.

21. A compound of claim 9 which is N-[(2,6-dichlorophenyl)carbonyl]-4-(1,3-diethyl-6-methyl-2,4-dioxo-5-pyrimidinyl)-L-phenylalanine.

22. A compound of claim 9 which is N-[(2-chloro-6-methylphenyl)carbonyl]-4-(1,3-diethyl-6-methyl-2,4-dioxo-5-pyrimidinyl)-L-phenylalanine.

23. A compound of claim 9 which is N-[(2-chloro-6-methylphenyl)carbonyl]-4-(1,3-dimethyl-2,4-dioxo-5-pyrimidinyl)-L-phenylalanine.

24. A compound of claim 9 which is N-[(2-bromo-6-methylphenyl)carbonyl]-4-(1,3-dimethyl-2,4-dioxo-5-pyrimidinyl)-L-phenylalanine.

25. A compound of claim 9 which is N-[(2-bromo-5-methoxyphenyl)carbonyl]-4-[1,3-dimethyl-2,4-dioxo-5-pyrimidinyl]-L-phenylalanine.

26. A compound of claim 8 wherein R$^2$ and R$^3$ are lower alkyl; R$^4$ is hydrogen or lower alkyl, R$_5$ is hydrogen, and R$_6$ is hydrogen, lower alkyl carbonyloxy lower alkyl, lower alkyl, or R₆ is a group of formula P-3:

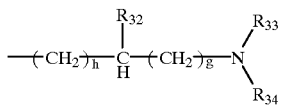

P-3 wherein
R₃₂ is hydrogen or lower alkyl; R₃₃ is hydrogen, lower alkyl, aryl; R₃₄ is hydrogen or lower alkyl; h is an integer from 0 to 2; g is an integer from 0 to 2; the sum of h and g is 1 to 3; or
R₆ is a group of formula P-4:

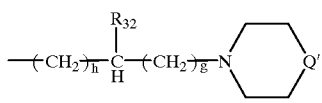

P-4 wherein
R₃₂, g, and h are as previously defined; Q' is O, S, —(CH₂)ⱼ—, or a group of the formula N-R₃₅; wherein R₃₅ is hydrogen.

27. A compound of claim 26 wherein R₆ is lower alkyl.

28. A compound of claim 27 which is N-[(2,6-difluorophenyl)carbonyl]-4-(1,3,6-trimethyl-2,4-dioxo-5-pyrimidinyl)-L-phenylalanine ethyl ester.

29. A compound of claim 27 which is N-[(2,6-dichlorophenyl)carbonyl]-4-(1,3,6-trimethyl-2,4-dioxo-5-pyrimidinyl)-L-phenylalanine ethyl ester.

30. A compound of claim 27 which is N-[(2-chloro-6-methylphenyl)carbonyl]-4-(1,3,6-trimethyl-2,4-dioxo-5-pyrimidinyl)-L-phenylalanine ethyl ester.

31. A compound of claim 26 wherein R₆ is lower alkyl carbonyloxy lower alkyl.

32. A compound of claim 31 which is N-[(2,6-difluorophenyl)carbonyl]-4-(1,3,6-trimethyl-2,4-dioxo-5-pyrimidinyl)-L-phenylalanine 1-(acetoxy)ethyl ester.

33. A compound of claim 31 which is N-[(2,6-dichlorophenyl)carbonyl]-4-(1,3,6-trimethyl-2,4-dioxo-5-pyrimidinyl)-L-phenylalanine 1-(acetoxy)ethyl ester.

34. A compound of claim 31 which is N-[(2-chloro-6-methylphenyl)carbonyl]-4-(1,3,6-trimethyl-2,4-dioxo-5-pyrimidinyl)-L-phenylalanine 1-(acetoxy)ethyl ester.

35. A compound of claim 26 wherein R₆ is a group of the formula P-3 wherein R³² is hydrogen; R³³ and R³⁴ are lower alkyl; h is 1; and g is 0.

36. A compound of claim 35 which is N-[(2,6-difluorophenyl)carbonyl]-4-(1,3,6-trimethyl-2,4-dioxo-5-pyrimidinyl)-L-phenylalanine 2-[(N,N-diethyl)amino]ethyl ester.

37. A compound of claim 35 which is N-[(2,6-dichlorophenyl)carbonyl]-4-(1,3,6-trimethyl-2,4-dioxo-5-pyrimidinyl)-L-phenylalanine 2-[(N,N-diethyl)amino]ethyl ester.

38. A compound of claim 35 which is N-[(2-chloro-6-methylphenyl)carbonyl]-4-(1,3,6-trimethyl-2,4-dioxo-5-pyrimidinyl)-L-phenylalanine 2-[(N,N-diethyl)amino]ethyl ester.

39. A compound of claim 26 wherein R⁶ is a group of the formula P-4 wherein R³² is hydrogen; h is 1; g is 0; and Q' is O.

40. A compound of claim 39 which is N-[(2,6-dichlorophenyl)carbonyl]-4-(1,3,6-trimethyl-2,4-dioxo-5-pyrimidinyl)-L-phenylalanine 2-(4-morpholino)ethyl ester.

41. A compound of claim 39 which is N-[(2-chloro-6-methylphenyl)carbonyl]-4-(1,3,6-trimethyl-2,4-dioxo-5-pyrimidinyl)-L-phenylalanine 2-(4-morpholino)ethyl ester.

42. A compound of claim 8 wherein R² and R³ are lower alkyl; R⁴ is perfluoro lower alkyl, and R⁵ and R⁶ are hydrogen.

43. A compound of claim 42 which is N-[1-(2,6-dichlorophenyl)carbonyl]-4-(1,3-dimethyl-2,4-dioxo-6-(trifluoromethyl)-5-pyrimidinyl)-L-phenylalanine.

44. A compound of claim 42 which is N-[(2-chloro-6-methylphenyl)carbonyl]-4-[1,3-dimethyl-2,4-dioxo-6-(trifluoromethyl)-5-pyrimidinyl]-L-phenylalanine.

45. A compound of claim 42 which is N-[[2-fluoro-6-(trifluoromethyl)phenyl]carbonyl]-4-(1,3-dimethy-2,4-dioxo-6-(trifluoromethyl)-5-pyrimidinyl)-L-phenylalanine.

46. A compound of claim 8 wherein R² and R³ are lower alkyl; R⁴ is hydrogen; R⁵ is lower alkyl, and R⁶ is hydrogen.

47. A compound of claim 46 which is N-[(2-chloro-6-methylphenyl)carbonyl]-4-(1,3-dimethyl-2,4-dioxo-5-pyrimidinyl)-3-methyl-L-phenylalanine.

48. A compound of claim 46 which is N-[(2,6-dichlorophenyl)carbonyl]-4-(1,3-dimethyl-2,4-dioxo-5-pyrimidinyl)-3-methyl-L-phenylalanine.

49. A compound of claim 46 which is N-[(2,6-dichlorophenyl)carbonyl]-4-(1,3,6-trimethyl-2,4-dioxo-5-pyrimidinyl)-3-methyl-L-phenylalanine.

50. A compound of claim 7 wherein R₁ is a group of formula Y-3 which is a 3–7 membered ring of the formula:

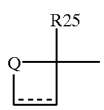

Y-3 wherein
R₂₅ is a group of formula R₂₆—(CH₂)ₑ—, wherein R₂₆ is lower alkoxy, Q is —(CH₂)ƒ—, e is an integer from 0 to 4, and f is an integer from 0 to 3.

51. A compound of claim 50 wherein R² and R³ are lower alkyl, R⁴ is hydrogen or lower alkyl; and R⁵ and R⁶ are hydrogen.

52. A compound of claim 51 which is 4-(1,3-dimethyl-2,4-dioxo-5-pyrimidinyl)]-N-[[1-(2-methoxyethyl)cyclopentyl]carbonyl]-L-phenylalanine.

53. A compound of claim 51 which is N-[[1-(2-methoxyethyl)cyclopentyl]carbonyl]-4-(1,3,6-trimethyl-2,4-dioxo-5-pyrimidinyl)-L-phenylalanine.

54. A compound of claim 51 which is 4-(1,3-diethyl-6-methyl-2,4-dioxo-5-pyrimidinyl)-N-[[1-(2-methoxyethyl)cyclopentyl]carbonyl]-L-phenylalanine.

55. A compound of claim 7 wherein R₂ and R₃ are lower alkyl; and R₄, R₅ and R₆ are hydrogen.

56. A compound of claim 55 wherein R₁ is a group of the formula Y-1.

57. A compound of claim 56 wherein R₁ is a group of the formula Y-1 wherein R₂₂ and R₂₃ are independently lower alkyl or halogen; and R₂₄ is hydrogen.

58. A compound of claim 56 wherein R₁ is a group of the formula Y-1 wherein R₂₂ and R₂₃ are independently hydrogen or halogen; and R₂₄ is lower alkoxy.

59. A compound of claim 55 wherein R₁ is a five or six membered heteroaromatic ring bonded via a carbon atom to the amide carbonyl wherein said ring contains one, two or three heteroatoms selected from the group consisting of N, O and S and one or two atoms of said ring are independently substituted by lower alkyl, cycloalkyl, halogen, cyano, perfluoroalkyl, or aryl and at least one of said substituted atoms is adjacent to the carbon atom bonded to the amide carbonyl.

60. A compound of claim 55 wherein $R_1$ is a group of formula Y-3.

61. A compound of claim 60 wherein $R_1$ is a group of formula Y-3 wherein $R_{25}$ is a group of formula $R_{26}$—$(CH_2)_e$—, wherein $R_{26}$ is lower alkoxy, Q is —$(CH_2)_f$—, e is an integer from 0 to 4, and f is an integer from 0 to 3.

* * * * *

UNITED STATES PATENT AND TRADEMARK OFFICE
CERTIFICATE OF CORRECTION

PATENT NO. : 6,380,387 B1
DATED : April 30, 2002
INVENTOR(S) : Sidduri et al.

It is certified that error appears in the above-identified patent and that said Letters Patent is hereby corrected as shown below:

Column 91,
Line 66, replace "$R_{35}^{S}$" with -- $R_{35}$ --.

Signed and Sealed this

Nineteenth Day of November, 2002

Attest:

JAMES E. ROGAN
Attesting Officer          Director of the United States Patent and Trademark Office